US012715920B2

(12) United States Patent
Koerber et al.

(10) Patent No.: US 12,715,920 B2
(45) Date of Patent: Aug. 25, 2026

(54) CD8 BINDING AGENTS AND USES THEREOF

(71) Applicant: GENENTECH, INC., South San Francisco, CA (US)

(72) Inventors: James Thomas Koerber, South San Francisco, CA (US); Alejandra Beatrice Urpi Urrutia, South San Francisco, CA (US); Simon-Peter Williams, South San Francisco, CA (US); Christopher Williamson Davies, South San Francisco, CA (US); Shravan Kumar Sriraman, South San Francisco, CA (US); Herman Singh Gill, South San Francisco, CA (US); James Richard Kiefer, Jr., South San Francisco, CA (US)

(73) Assignee: GENENTECH, INC., South San Francisco, CA (US)

(*) Notice: Subject to any disclaimer, the term of this patent is extended or adjusted under 35 U.S.C. 154(b) by 1105 days.

(21) Appl. No.: 17/640,499

(22) PCT Filed: Sep. 3, 2020

(86) PCT No.: PCT/US2020/049110
§ 371 (c)(1),
(2) Date: Jul. 27, 2022

(87) PCT Pub. No.: WO2021/046159
PCT Pub. Date: Mar. 11, 2021

(65) Prior Publication Data

US 2023/0192853 A1 Jun. 22, 2023

Related U.S. Application Data

(60) Provisional application No. 62/895,865, filed on Sep. 4, 2019.

(51) Int. Cl.

| | |
|---|---|
| ***C07K 16/28*** | (2006.01) |
| ***A61K 51/10*** | (2006.01) |
| ***G01N 33/575*** | (2026.01) |

(52) U.S. Cl.
CPC ...... *C07K 16/2815* (2013.01); *A61K 51/1027* (2013.01); *A61K 51/1093* (2013.01); *G01N 33/5759* (2026.01); *C07K 2317/22* (2013.01); *C07K 2317/24* (2013.01); *C07K 2317/569* (2013.01); *C07K 2317/74* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 4,943,533 | A | 7/1990 | Mendelsohn et al. |
| 5,208,020 | A | 5/1993 | Chari et al. |
| 5,212,290 | A | 5/1993 | Vogelstein et al. |
| 5,457,105 | A | 10/1995 | Barker |
| 5,475,001 | A | 12/1995 | Barker |
| 5,545,806 | A | 8/1996 | Lonberg et al. |
| 5,545,807 | A | 8/1996 | Surani et al. |
| 5,569,825 | A | 10/1996 | Lonberg et al. |
| 5,616,582 | A | 4/1997 | Barker |
| 5,625,126 | A | 4/1997 | Lonberg et al. |
| 5,633,425 | A | 5/1997 | Lonberg et al. |
| 5,648,237 | A | 7/1997 | Carter |
| 5,654,307 | A | 8/1997 | Bridges et al. |
| 5,661,016 | A | 8/1997 | Lonberg et al. |
| 5,679,683 | A | 10/1997 | Bridges et al. |
| 5,747,498 | A | 5/1998 | Schnur et al. |
| 5,760,041 | A | 6/1998 | Wissner et al. |
| 5,770,599 | A | 6/1998 | Gibson |
| 5,789,199 | A | 8/1998 | Joly et al. |
| 5,804,396 | A | 9/1998 | Plowman |
| 5,840,523 | A | 11/1998 | Simmons et al. |
| 5,866,572 | A | 2/1999 | Barker et al. |
| 5,891,996 | A | 4/1999 | Rio et al. |

(Continued)

FOREIGN PATENT DOCUMENTS

| | | |
|---|---|---|
| EP | 0659439 A2 | 6/1995 |
| WO | 9110741 A1 | 7/1991 |

(Continued)

OTHER PUBLICATIONS

Webster "Reagent" accessed from mirriam-webster.com on Nov. 19, 2025 (Year: 2025).*

(Continued)

*Primary Examiner* — Adam Weidner

(74) *Attorney, Agent, or Firm* — Lathrop GPM LLP; Malaika O.D. Tyson; Jason Kuchar

(57) ABSTRACT

Provided are CD8 binding agents comprising a VHH domain that specifically binds human CD8. Also provided are nucleic acids encoding such CD8 binding agents, vectors comprising such nucleic acids, host cells comprising same, and methods of making such CD8 binding agents. Also provided are CD8 binding agents having the VHH domain conjugated to a detectable label. Provided are methods of using such CD8 binding agents to detect CD8+ T cells, monitor disease progress, and monitor treatment progress in a subject having cancer, autoimmune disease or condition, transplant rejection or graft-versus-host disease.

23 Claims, 13 Drawing Sheets

Specification includes a Sequence Listing.

(56) References Cited

U.S. PATENT DOCUMENTS

| | | | |
|---|---|---|---|
| 5,959,177 | A | 9/1999 | Hein et al. |
| 6,002,008 | A | 12/1999 | Wissner et al. |
| 6,015,695 | A | 1/2000 | Casterman et al. |
| 6,040,498 | A | 3/2000 | Stomp et al. |
| 6,084,095 | A | 7/2000 | Bridges et al. |
| 6,140,332 | A | 10/2000 | Traxler et al. |
| 6,171,586 | B1 | 1/2001 | Lam et al. |
| 6,235,883 | B1 | 5/2001 | Jakobovits et al. |
| 6,265,410 | B1 | 7/2001 | Bridges et al. |
| 6,267,958 | B1 | 7/2001 | Andya et al. |
| 6,344,455 | B1 | 2/2002 | Bridges et al. |
| 6,344,459 | B1 | 2/2002 | Bridges et al. |
| 6,391,874 | B1 | 5/2002 | Cockerill et al. |
| 6,399,602 | B1 | 6/2002 | Barker et al. |
| 6,417,429 | B1 | 7/2002 | Hein et al. |
| 6,420,548 | B1 | 7/2002 | Vézina et al. |
| 6,455,534 | B2 | 9/2002 | Bridges et al. |
| 6,521,620 | B1 | 2/2003 | Bridges et al. |
| 6,596,726 | B1 | 7/2003 | Bridges et al. |
| 6,602,863 | B1 | 8/2003 | Bridges et al. |
| 6,713,484 | B2 | 3/2004 | Bridges et al. |
| 7,125,978 | B1 | 10/2006 | Vézina et al. |
| 12,473,338 | B2 * | 11/2025 | Kley ...................... C07K 14/56 |
| 2005/0260186 | A1 | 11/2005 | Bookbinder et al. |
| 2006/0104968 | A1 | 5/2006 | Bookbinder et al. |
| 2016/0363593 | A1 * | 12/2016 | Sebastiao ......... G01N 33/57415 |

FOREIGN PATENT DOCUMENTS

| | | | |
|---|---|---|---|
| WO | 9630347 | A1 | 10/1996 |
| WO | 9633735 | A1 | 10/1996 |
| WO | 9633978 | A1 | 10/1996 |
| WO | 9633980 | A1 | 10/1996 |
| WO | 9634096 | A1 | 10/1996 |
| WO | 9640210 | A1 | 12/1996 |
| WO | 9738983 | A1 | 10/1997 |
| WO | 9814451 | A1 | 4/1998 |
| WO | 9824893 | A2 | 6/1998 |
| WO | 9843960 | A1 | 10/1998 |
| WO | 9850038 | A1 | 11/1998 |
| WO | 9850433 | A2 | 11/1998 |
| WO | 9906378 | A1 | 2/1999 |
| WO | 9906396 | A1 | 2/1999 |
| WO | 9909016 | A1 | 2/1999 |
| WO | 9924037 | A1 | 5/1999 |
| WO | 2006044908 | A2 | 4/2006 |
| WO | 2019032661 | A1 | 2/2019 |

OTHER PUBLICATIONS

Kussie "A Single Engineered Amino Acid Substitution Changes Antibody Fine Specificity" J immunol 152(1):146-52 (Year: 1994).*

Mueller et al., "Spliceosomal Peptide P140 for Immunotherapy of Systemic Lupus Erythematosus", American College of Rheumatology, Arthritis & Rheumatism, vol. 58, No. 12, Dec. 2008, pp. 3873-3883.

Mariuzza et al., "The Structural Basis of Antigen-Antibody Recognition," Departement d'Immunologie, Institut Pasteur, Biophys. Chem. 1987. 16: 139-159.

Patent Office of the Russian Federation, "Office Action", issued in connection with Russian Patent Application No. 2022106415, dated Apr. 11, 2024, 7 pages.

Deng et al., "The Emerging Epigenetic Role of CD8+T Cells in Autoimmune Diseases: A Systematic Review," frontiers in Immunology, Apr. 18, 2019, 15 pages.

Harper, et al., "CD8 T-cell recognition of acquired alloantigen promotes acute allograft rejection," CrossMark, Sep. 3, 2015, 6 pages.

Korotkov, "Significance of T-Helpers, CD4+ Effector T-cells," Transpantology and Artificial Organs, 2017, vol. 19, No. S, with translation, 4 pages.

Office Action received in Russian Application No. 2022106415/10 dated Jan. 23, 2023, with translation, 11 pages.

Search Report received Russian Application No. 2022106415/10 dated Jan. 23, 2023, with translation, 4 pages.

Rashidian, et al., "Predicting the response to CTLA-4 blockade by longitudinal noninvasive monitoring of CD8 cells," JEM Brief Definitive Report, The Rockefeller University Press, J. Exp. Med. 2017 vol. 214, No. 8, [no date], 13 pages.

Search Report received in International Application No. PCT/US2020/049110 dated Dec. 7, 2020, 4 pages.

Written Opinion received in International Application No. PCT/US2020/049110 dated Dec. 7, 2020, 6 pages.

Office Action and Search Report received in Chinese Application No. 202080076879.1 dated May 24, 2023, with translation, 11 pages.

Korean Office Action for Korean Patent Application No. 10-2022-7010647 mailed Nov. 11, 2025, 19 pages.

Australian Government—IP Australia, Office Action for Application No. 2020341458, dated Apr. 7, 2026.

* cited by examiner

```
rhesus_CD8a   MRNQAPGRPKGATSPPPLPTGSRAPPVAPELRAEPRPGERVMAPPVTALL 50   SEQ ID NO: 15
cyno_CD8a     MRNQAPGRPKGATSPPPLPTGSRAPPVAPELRAEPRPGERVMAPPVTALL 50   SEQ ID NO: 14
human_CD8a                                             MALPVTALL 9    SEQ ID NO: 13

rhesus_CD8a   LPLVLLLHAARPNQFRVSPLGRTWNLGETVELKCQVLLSNPTSGCSWLFQ 100  SEQ ID NO: 15
cyno_CD8a     LPLVLLLHAARPNQFRVSPLGRTWNLGETVELKCQVLLSNPTSGCSWLFQ 100  SEQ ID NO: 14
human_CD8a    LPLALLLHAARPSQFRVSPLDRTWNLGETVELKCQVLLSNPTSGCSWLFQ 59   SEQ ID NO: 13

rhesus_CD8a   PRGTAARPTFLLYLSQNKPKAAEGLDTQRFSGKRLGDTFVLTLRDFRQEN 150  SEQ ID NO: 15
cyno_CD8a     PRGTAARPTFLLYLSQNKPKAAEGLDTQRFSGKRLGDTFVLTLRDFRQEN 150  SEQ ID NO: 14
human_CD8a    PRGAAASPTFLLYLSQNKPKAAEGLDTQRFSGKRLGDTFVLTLSDFRREN 109  SEQ ID NO: 13

rhesus_CD8a   EGYYFCSALSNSIMYFSHFVPVFLPAKPTTTPAPRSPTPAPTTASQPLSL 200  SEQ ID NO: 15
cyno_CD8a     EGYYFCSALSNSIMYFSHFVPVFLPAKPTTTPAPRPPTPAPTTASQPLSL 200  SEQ ID NO: 14
human_CD8a    EGYYFCSALSNSIMYFSHFVPVFLPAKPTTTPAPRPPTPAPTIASQPLSL 159  SEQ ID NO: 13

rhesus_CD8a   RPEACRPAAGGSVNTRGLDFACDIYIWAPLAGACGVLLLSLVITLYCNHR 250  SEQ ID NO: 15
cyno_CD8a     RPEACRPAAGGSVNTRGLDFACDIYIWAPLAGACGVLLLSLVITLYCNHR 250  SEQ ID NO: 14
human_CD8a    RPEACRPAAGGAVHTRGLDFACDIYIWAPLAGTCGVLLLSLVITLYCNHR 209  SEQ ID NO: 13

rhesus_CD8a   NRRRVCKCPRPVVKSGGKPSLSDRYV 276  SEQ ID NO: 15
cyno_CD8a     NRRRVCKCPRPVVKSGGKPSLSDRYV 276  SEQ ID NO: 14
human_CD8a    NRRRVCKCPRPVVKSGDKPSLSARY  234  SEQ ID NO: 13
```

FIG. 2

%CD8+ HPBALL Cells

PET Uptake Mean (%ID/g)

CD8 BINDING AGENTS AND USES THEREOF

CROSS REFERENCE TO RELATED APPLICATIONS

This application claims priority benefit of U.S. Provisional Application No. 62/895,865 filed Sep. 4, 2019, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392049240SEQLIST.txt, date recorded: Aug. 19, 2020, size: 14 KB).

FIELD

The present application relates to CD8 binding agents based on anti-CD8 VHH domains and methods of using such CD8 binding agents for imaging $CD8^+$ T-cells in vivo.

BACKGROUND

Characterization of the number, types, and spatial distribution of immune cells in tumor tissues can provide crucial information regarding cancer diagnosis, prognosis, therapy selection, and response to therapy. Specifically, $CD8^+$ cytotoxic lymphocytes have been consistently reported as having diagnostic and prognostic significance in various cancers. Current methods of detecting $CD8^+$ cells entail the isolation of cells from the peripheral blood or a tissue of interest. Such sampling methods are prone to error and do not provide dynamic information that reflects the number, localization, and movement of $CD8^+$ cells in vivo. One exemplary noninvasive method for detecting immune cells in vivo is positron emission tomography (PET) using radiolabeled tracers. However, the use of such tracers is limited by radioisotope half-life and cell division, which leads to probe dilution in vivo. Accordingly, there remains a need in the art for methods and reagents for monitoring changes in the quantity and temporal distribution of $CD8^+$ cells in vivo.

BRIEF SUMMARY

Provided herein is a CD8 binding agent comprising a variable domain of the heavy chain of a heavy chain antibody (VHH domain), wherein the CD8 binding agent specifically binds a human CD8 with a $K_D$ of about 1 nM or less. In some embodiments, the CD8 binding agent specifically binds a human CD8 with a $K_D$ of about 500 pM or less, about 250 pM or less, or about 100 pM or less. In some embodiments, the CD8 binding agent specifically binds a human CD8 with a $K_D$ of about 132 pm, or about 50 pM. In some embodiments, the CD8 binding agent binds human CD8 with a $k_{off}$ of about 0.002/s or less, or about 0.001/s or less. In some embodiments, the CD8 binding agent binds human CD8 with a $k_{off}$ of about 0.0018/s, or about 0.00085/s. In some embodiments, the CD8 binding agent binds cynomolgus CD8 with a $K_D$ of about 1 nM or less. In some embodiments, the CD8 binding agent binds cynomolgus CD8 with a $K_D$ of about 500 pM or less, about 250 pM or less, or about 150 pM or less. In some embodiments, the CD8 binding agent binds cynomolgus CD8 with a $K_D$ of about 344 pM or about 137 pM. In some embodiments, the CD8 binding agent binds cynomolgus CD8 with a $k_{off}$ of about 0.004/s or less, or about 0.002/s or less. In some embodiments, the CD8 binding agent binds cynomolgus CD8 with a $k_{off}$ of about 0.0037/s, or about 0.0019/s. In some embodiments, the CD8 binding agent has a CD8-binding half-life (e.g., in an in vitro binding assay) of at least about 30 minutes, such as at least about 1 hour, 2 hours or more. In some embodiments, the CD8 binding agent specifically binds a rhesus monkey CD8 with a $K_D$ of about 1 nM or less. In some embodiments, the CD8 binding agent does not bind mouse or rat CD8.

In some embodiments according to (or as applied to) any of the embodiments above, the CD8 binding agent does not stimulate or inhibit the activation of $CD8^+$ T cells. In some embodiments, the CD8 binding agent does not induce $CD8^+$ T cell proliferation. In some embodiments, the CD8 binding agent does not bind $CD4^+$ T cells.

In some embodiments according to (or as applied to) any of the embodiments above, the VHH domain is a camelid VHH, such as a llama WM. In some embodiments, the VHH domain is chimeric. In some embodiments, the VHH is humanized. In some embodiments, the VHH is affinity matured.

In some embodiments according to (or as applied to) any of the embodiments above, the VHH domain specifically binds a human CD8a epitope comprising Arg25, Lys42, Gln44, Val45, Leu46, Leu47, Ser48, Pro50, Thr51, Ser52, Gln75, Arg93, Leu94, Gly95, Asp96, and Thr97, wherein the amino acid numbering is according to SEQ ID NO: 13. In some embodiments, the amino acid residues in the human CD8α epitope are within about 4.5 Å from one or more amino acid residues of the VHH domain in a crystal structure of the CD8 binding agent or the VHH domain bound to the human CD8α.

In some embodiments according to (or as applied to) any of the embodiments above, the VHH domain comprises a complementarity determining region (CDR) 1 comprising an amino acid sequence of SEQ ID NO: 6 or 7; a CDR2 comprising an amino acid sequence of SEQ ID NO: 8 or 9; and a CDR3 comprising an amino acid sequence of any one of SEQ ID NOs: 10-12.

In some embodiments according to (or as applied to) any of the embodiments above, the VHH domain comprises a CDR1 comprising the amino acid sequence of SEQ ID NO: 6, a CDR2 comprising the amino acid sequence of SEQ ID NO: 8, and a CDR3 comprising the amino acid sequence of SEQ ID NO: 10. In some embodiments according to (or as applied to) any of the embodiments above, the VHH domain comprises a CDR1 comprising the amino acid sequence of SEQ ID NO: 6, a CDR2 comprising the amino acid sequence of SEQ ID NO: 9, and a CDR3 comprising the amino acid sequence of SEQ ID NO: 11. In some embodiments according to (or as applied to) any of the embodiments above, the VHH domain comprises a CDR1 comprising the amino acid sequence of SEQ ID NO: 7, a CDR2 comprising the amino acid sequence of SEQ ID NO: 9, and a CDR3 comprising the amino acid sequence of SEQ ID NO: 11. In some embodiments according to (or as applied to) any of the embodiments above, the VHH domain comprises a CDR1 comprising the amino acid sequence of SEQ ID NO: 6, a CDR2 comprising the amino acid sequence of SEQ ID NO: 9, and a CDR3 comprising the amino acid sequence of SEQ ID NO: 12.

In some embodiments according to (or as applied to) any of the embodiments above, wherein the VHH domain comprises L49A, wherein the numbering is according to Kabat numbering. In some embodiments, the CD8 binding agent can be purified using Protein A affinity chromatography.

In some embodiments according to (or as applied to) any of the embodiments above, the VHH domain comprises one or more amino acid modifications selected from the group consisting of V89T substitution, T110Q substitution, S112Q substitution and addition of A at position 114 (referred herein after as "A114 addition"), wherein the numbering is according to Kabat numbering. In some embodiments, the VHH domain comprises V89T substitution, T110Q substitution, S112Q substitution and A114 addition, wherein the numbering is according to Kabat numbering. In some embodiments, the CD8 binding agent does not bind preexisting anti-VHH antibodies in a subject receiving the CD8 binding agent.

In some embodiments according to (or as applied to) any of the embodiments above, the VHH domain comprises the amino acid sequence of SEQ ID NO: 1. In some embodiments according to (or as applied to) any of the embodiments above, the VHH domain comprises the amino acid sequence of SEQ ID NO: 2. In some embodiments according to (or as applied to) any of the embodiments above, the VHH domain comprises the amino acid sequence of SEQ ID NO: 3. In some embodiments according to (or as applied to) any of the embodiments above, the VHH domain comprises the amino acid sequence of SEQ ID NO: 4.

Also provided herein is an isolated nucleic acid encoding the CD8 binding agent according to (or as applied to) any of the embodiments above. In some embodiments, provided is an expression vector comprising the nucleic acid according to (or as applied to) any of the embodiments above. In some embodiments, provided is a host cell comprising the nucleic acid or the expression vector according to (or as applied to) any of the embodiments above. In some embodiments, the host cell is a eukaryotic cell, such as a mammalian cell, for example, CHO cell or Expi293 cell. In some embodiments, the host cell is a prokaryotic cell, such as an *E. coli* cell.

Further provided herein is a method of making the CD8 binding agent according to (or as applied to) any of the embodiments above, the method comprising: a) culturing the host cell according to (or as applied to) any of the embodiments above under conditions where the agent is produced; and b) recovering the CD8 binding agent produced by the host cell.

In some embodiments according to (or as applied to) any of the embodiments above, the CD8 binding agent comprises a label. A CD8 binding agent comprising a label is referred herein as a "labeled CD8 binding agent".

In some embodiments, there is provided a method of preparing a labeled CD8 binding agent, comprising conjugating a chelating moiety to the VHH domain of a CD8 binding agent according to (or as applied to) any of the embodiments above to provide a conjugate, and contacting the conjugate with an aluminum fluoride complex comprising $^{18}F$ to provide the labeled CD8 binding agent, wherein the chelating moiety is a compound of Formula (I):

(I)

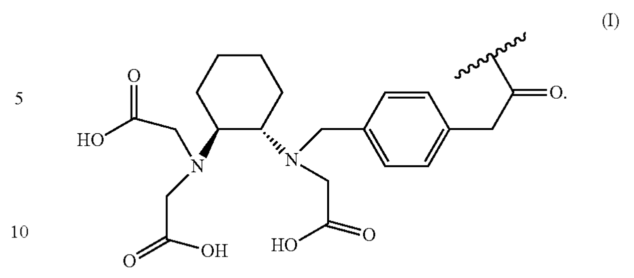

In some embodiments, the conjugate is contacted with the aluminum fluoride complex in the presence of one or more anti-oxidant compounds, such as methionine and/or N-acetyl-tryptophan.

Provided herein is a labeled CD8 binding agent comprising an anti-CD8 VHH domain according to (or as applied to) any of the embodiments above conjugated to a label. In some embodiments, the label is a fluorescent dye, a radionuclide, or an enzyme. In some embodiments according to (or as applied to) any of the embodiments above, the label is a radionuclide. In some embodiments, the radionuclide is $^{18}F$, $^{89}Zr$, $^{99m}Tc$, $^{67}Ga$, $^{68}Ga$, $^{64}Cu$, $^{52}Mn$, $^{111}In$, or $^{124}I$. In some embodiments, the VHH domain is conjugated to a label via a chelating moiety. In some embodiments, the chelating moiety is covalently linked to the VHH domain via a lysine residue. In some embodiments, the label forms a complex with a metal, wherein the complex is chelated by the chelating moiety. In some embodiments, the label is $^{18}F$ and the metal is aluminum. In some embodiments, the chelating moiety is a compound of Formula (I).

Provided herein is a labeled CD8 binding agent comprising an anti-CD8 VHH domain comprising a CDR1 comprising the amino acid sequence of SEQ ID NO: 7, a CDR2 comprising the amino acid sequence of SEQ ID NO: 9, and a CDR3 comprising the amino acid sequence of SEQ ID NO: 11, wherein the VHH domain is conjugated to a radionuclide (e.g., $^{18}F$) via a chelating moiety. In some embodiments, the chelating moiety is a compound of Formula (I), and the radionuclide is $^{18}F$ complexed with aluminum. In some embodiments, the VHH domain comprises the amino acid sequence of SEQ ID NO: 3.

Provided herein is a labeled CD8 binding agent comprising an anti-CD8 VHH domain comprising a CDR1 comprising the amino acid sequence of SEQ ID NO: 6, a CDR2 comprising the amino acid sequence of SEQ ID NO: 9, and a CDR3 comprising the amino acid sequence of SEQ ID NO: 12, wherein the VHH domain is conjugated to a radionuclide (e.g., $^{18}F$) via a chelating moiety. In some embodiments, the chelating moiety is a compound of Formula (I), and the radionuclide is $^{18}F$ complexed with aluminum. In some embodiments, the VHH domain comprises the amino acid sequence of SEQ ID NO: 4.

Also provided herein is a pharmaceutical composition comprising a CD8 binding agent (including a labeled CD8 binding agent) according to (or as applied to) any of the embodiments above, and a pharmaceutically acceptable carrier.

Further provided herein are use of a CD8 binding agent (including a labeled CD8 binding agent) according to (or as applied to) any of the embodiments above for treatment or diagnosis of a disease or condition in a subject, and use of a CD8 binding agent (including a labeled CD8 binding agent) according to (or as applied to) any of the embodiments above in the preparation of a medicament for treatment or diagnosis of a disease or condition in a subject.

Further provided herein is a pharmaceutical formulation comprising a CD8 binding agent (including a labeled CD8 binding agent) according to (or as applied to) any of the embodiments above and one or more anti-oxidant compounds. In some embodiments, the one or more anti-oxidant compounds are methionine and/or N-acetyl tryptophan. In some embodiments, the pharmaceutical formulation comprises methionine and N-acetyl tryptophan. In some embodiments, the pharmaceutical formulation further comprises histidine and sucrose.

Provided herein is a method of detecting $CD8^+$ cells in a subject, the method comprising: a) administering a labeled CD8 binding agent according to (or as applied to) any of the embodiments above, to the subject; and b) detecting binding of the labeled CD8 binding agent to $CD8^+$ cells in the subject, wherein the detection of the binding indicates the presence of $CD8^+$ cells. In some embodiments, detecting binding of the labeled CD8 binding agent to $CD8^+$ cells in the subject comprises imaging $CD8^+$ cells in the subject. In some embodiments, imaging $CD8^+$ cells in the subject comprises performing a positron emission tomography (PET) scan or positron emission tomography/computed tomography (PET/CT) scan on the subject. In some embodiments, the $CD8^+$ cells are $CD8^+$ T cells. In some embodiments, the $CD8^+$ cells are CD8+ tumor cells. In some embodiments, the detecting is carried out within about 1 day or less (e.g., within about 6 hours, 4 hours, 2 hours, 90 minutes, 1 hour, 30 minutes or less) after the administering. In some embodiments, the method is repeated for one or more times, such as about 1 to 4 times per year. In some embodiments, the method is repeated after about 1 day after the prior administration of the CD8 binding agent. In some embodiments, the method is repeated for more than 1 year. In some embodiment, the method has a sensitivity of about 1 nM to about 30 nM. In some embodiments, the subject is a human or a non-human primate. In some embodiments, the subject is a cynomolgus monkey or a rhesus monkey. In some embodiments, the subject is human. In some embodiments, the subject has cancer. In some embodiments, the subject has an autoimmune disease or condition, transplant rejection, or graft-versus-host disease.

Provided herein is a method of predicting responsiveness of a subject having cancer to an immunotherapeutic agent, a cell therapy, or a cancer vaccine, the method comprising: a) administering the labeled CD8 binding agent according to (or as applied to) any of the embodiments above to the subject and; b) detecting binding of the labeled CD8 binding agent to $CD8^+$ T cells in a tumor tissue in the subject, wherein the detection of the binding indicates that the subject is likely to respond to the immunotherapeutic agent, the cell therapy, or the cancer vaccine. In some embodiments, detecting binding of the labeled CD8 binding agent to $CD8^+$ cells in the subject comprises imaging $CD8^+$ cells in the subject. In some embodiments, imaging $CD8^+$ cells in the subject comprises performing a positron emission tomography (PET) scan or positron emission tomography/computed tomography (PET/CT) scan on the subject. In some embodiments, the method further comprises the step of: (c) administering a therapeutically effective amount of the immunotherapeutic agent, the cell therapy, or the cancer vaccine to the subject in whom the binding has been detected. In some embodiments, the detecting is carried out within about 1 day or less (e.g., within about 6 hours, 4 hours, 2 hours, 90 minutes, 1 hour, 30 minutes or less) after the administering. In some embodiments, the method is repeated for one or more times, such as about 1 to 4 times per year. In some embodiments, the method is repeated after at least 1 day after the prior administration of the CD8 binding agent. In some embodiments, the method is repeated for more than 1 year.

Also provided herein is a method of monitoring disease progression in a subject having cancer, the method comprising: a) administering the labeled CD8 binding agent according to (or as applied to) any of the embodiments above to the subject, and b) detecting binding of the labeled CD8 binding agent to $CD8^+$ T cells in a tumor tissue in the subject at a first time point and a second time point. In some embodiments, detecting binding of the labeled CD8 binding agent to $CD8^+$ cells in the subject comprises imaging $CD8^+$ cells in the subject. In some embodiments, imaging $CD8^+$ cells in the subject comprises performing a positron emission tomography (PET) scan or positron emission tomography/computed tomography (PET/CT) scan on the subject. In some embodiments, the method further comprises the step of: (c) administering a therapeutically effective amount of an immunotherapeutic agent, a cell therapy, or a cancer vaccine to the subject wherein a level of $CD8^+$ T cells in the tumor tissue at the second time point is higher than the level of $CD8^+$ T cells in the tumor tissue at the first time point. In some embodiments, the detecting is carried out within about 1 day or less (e.g., within about 6 hours, 4 hours, 2 hours, 90 minutes, 1 hour, 30 minutes or less) after the administering. In some embodiments, the method is repeated for one or more times, such as about 1 to 4 times per year. In some embodiments, the method is repeated after at least 1 day after the prior administration of the CD8 binding agent. In some embodiments, the subject is monitored for more than 1 year.

Provided herein is a method of monitoring treatment progress in a subject having cancer who has or is receiving an immunotherapeutic agent, a cell therapy, or a cancer vaccine, the method comprising: i) administering the labeled CD8 binding agent according to (or as applied to) any of the embodiments above to the subject in conjunction with the immunotherapeutic agent, the cell therapy, or the cancer vaccine, and ii) detecting binding of the labeled CD8 binding agent to $CD8^+$ T cells in a tumor tissue at a first time point and a second time point. In some embodiments, detecting binding of the labeled CD8 binding agent to $CD8^+$ cells in the subject comprises imaging $CD8^+$ cells in the subject. In some embodiments, imaging $CD8^+$ cells in the subject comprises performing a positron emission tomography (PET) scan or positron emission tomography/computed tomography (PET/CT) scan on the subject. In some embodiments, the labeled CD8 binding agent is administered before the immunotherapeutic agent, the cell therapy, or the cancer vaccine, wherein the first time point is after the administration of the labeled CD8 binding agent and prior to the administration of the immunotherapeutic agent, the cell therapy, or the cancer vaccine, and wherein the second time point is after the administration of the immunotherapeutic agent, the cell therapy, or the cancer vaccine. In some embodiments, the immunotherapeutic agent, the cell therapy, or the cancer vaccine is administered before the labeled CD8 binding agent, wherein the first time point is after the administration of the immunotherapeutic agent, the cell therapy, or the cancer vaccine and after the administration of the labeled CD8 binding agent, and wherein the second time point is after the first time point. In some embodiments, the detecting is carried out within about 1 day or less (e.g., within about 6 hours, 4 hours, 2 hours, 90 minutes, 1 hour, 30 minutes or less) after the administering.

In some embodiments, the method is repeated for one or more times, such as about 1 to 4 times per year. In some embodiments, the method is repeated after at least 1 day after the prior administration of the CD8 binding agent. In some embodiments, the subject is monitored for more than 1 year.

In some embodiments according to (or as applied to) any of the methods of predicting or methods of monitoring above, the immunotherapeutic agent is administered to the subject. In some embodiments, the immunotherapeutic agent is an anti-PDL1 antibody, an anti-PD1 antibody, an anti-TIGIT antibody, a TIGIT antagonist, an anti-CSF-1R antibody, an anti-CSF-1R antagonist, an anti-CEA antibody, an anti-CEA antagonist, an anti-CTLA4 antibody, a CTLA4 antagonist, an anti-OX40 antibody, or an OX40 agonist. In some embodiments, the immunotherapeutic agent is an anti-PD-L1 antibody. In some embodiments, the anti-PD-L1 antibody is administered in combination with one or more therapeutic agents. In some embodiments, the one or more therapeutic agents is TARCEVA® (erlotinib), ZELBORAF® (vemurafenib), GAZYVA® (obinutuzumab), AVASTIN® (bevacizumab), COTELLIC® (cobimetinib), ZELBORAF® (vemurafenib) and COTELLIC® (cobimetinib), ALECENSA® (alectinib), KADCYLA® (ado-trastuzumab emtansine), HERCEPTIN® (trastuzumab), PERJETA® (pertuzumab), polatuzumab, IFN-alpha, an anti-CD40 agent, an anti-OX40 antibody, an OX40 agonist, an anti-CSF-1R antibody, an anti-CEA antibody, an IDO inhibitor, or an anti-TIGIT antibody. In some embodiments, the immunotherapeutic agent is a cytokine. In some embodiments, the cytokine is IL2, an engineered IL2, IL15, or an engineered IL15. In some embodiments, the immunotherapeutic agent is a bispecific antigen-binding molecule that specifically binds CD3. In some embodiments, the bispecific antigen-binding molecule is an antibody or an antigen-binding fragment thereof. In some embodiments, the immunotherapeutic agent is a bispecific antigen-binding molecule that specifically binds CD16. In some embodiments, the bispecific antigen-binding molecule is an antibody or an antigen-binding fragment thereof. In some embodiments, the bispecific antigen-binding molecule specifically binds CD16A. In some embodiments, the immunotherapeutic agent is a dendritic cell modulator, such as dendritic cell activator or dendritic cell growth factor.

In some embodiments according to (or as applied to) any of the methods of predicting or methods of monitoring above, the cancer vaccine is administered to the subject. In some embodiments, the cancer vaccine is a Personalized Cancer Vaccine (PCV).

In some embodiments according to (or as applied to) any of the methods of predicting or methods of monitoring above, the cell therapy is administered to the subject. In some embodiments, the cell therapy is a CAR-T. In some embodiments, the cell therapy is neoantigen-specific T cells.

Provided herein is a method of predicting responsiveness of a subject having an autoimmune disease or condition, transplant rejection, or graft-versus-host disease to an immunotherapeutic agent, the method comprising: a) administering the labeled CD8 binding agent according to (or as applied to) any of the embodiments above to the subject and; b) detecting binding of the labeled CD8 binding agent to $CD8^+$ T cells in a diseased tissue in the subject, wherein the detection of the binding indicates that the subject is likely to respond to the immunotherapeutic agent. In some embodiments, detecting binding of the labeled CD8 binding agent to $CD8^+$ cells in the subject comprises imaging $CD8^+$ cells in the subject. In some embodiments, imaging $CD8^+$ cells in the subject comprises performing a positron emission tomography (PET) scan or positron emission tomography/computed tomography (PET/CT) scan on the subject. In some embodiments, the method further comprises the step of: (c) administering a therapeutically effective amount of an immunotherapeutic agent to the subject in whom the binding has been detected. In some embodiments, the detecting is carried out within about 1 day or less (e.g., within about 6 hours, 4 hours, 2 hours, 90 minutes, 1 hour, 30 minutes or less) after the administering. In some embodiments, the method is repeated for one or more times, such as about 1 to 4 times per year. In some embodiments, the method is repeated after at least 1 day after the prior administration of the CD8 binding agent. In some embodiments, the method is repeated for more than 1 year.

Also provided herein is a method of monitoring disease progression in a subject having an autoimmune disease or condition, transplant rejection, or graft-versus-host disease, the method comprising: a) administering the labeled CD8 binding agent according to (or as applied to) any of the embodiments above to the subject, and b) detecting binding of the labeled CD8 binding agent to $CD8^+$ T cells in a diseased tissue in the subject at a first time point and a second time point, wherein an increase in $CD8^+$ T cells from the first time point and the second time point is an indication that the autoimmune disease or condition, transplant rejection, or graft-versus-host disease has progressed. In some embodiments, detecting binding of the labeled CD8 binding agent to $CD8^+$ cells in the subject comprises imaging $CD8^+$ cells in the subject. In some embodiments, imaging $CD8^+$ cells in the subject comprises performing a positron emission tomography (PET) scan or positron emission tomography/computed tomography (PET/CT) scan on the subject. In some embodiments, the method further comprises the step of: (c) administering a therapeutically effective amount of an immunotherapeutic agent to the subject wherein a level of $CD8^+$ T cells in the diseased tissue at the second time point is lower than the level of $CD8^+$ T cells in the diseased tissue at the first time point. In some embodiments, the detecting is carried out within about 1 day or less (e.g., within about 6 hours, 4 hours, 2 hours, 90 minutes, 1 hour, 30 minutes or less) after the administering. In some embodiments, the method is repeated for one or more times, such as about 1 to 4 times per year. In some embodiments, the method is repeated after at least 1 day after the prior administration of the CD8 binding agent. In some embodiments, the subject is monitored for more than 1 year.

Provided herein is a method of monitoring treatment progress in a subject having an autoimmune disease or condition, transplant rejection, or graft-versus-host disease who has or is receiving an immunotherapeutic agent, the method comprising: i) administering the labeled CD8 binding agent according to (or as applied to) any of the embodiments above to the subject in conjunction with the immunotherapeutic agent, and ii) detecting binding of the labeled CD8 binding agent to $CD8^+$ T cells in a diseased tissue at a first time point and a second time point. In some embodiments, detecting binding of the labeled CD8 binding agent to $CD8^+$ cells in the subject comprises imaging $CD8^+$ cells in the subject. In some embodiments, imaging $CD8^+$ cells in the subject comprises performing a positron emission tomography (PET) scan or positron emission tomography/computed tomography (PET/CT) scan on the subject. In some embodiments, the labeled CD8 binding agent is administered before the immunotherapeutic agent, wherein the first time point is after the administration of the labeled CD8 binding agent and prior to the administration of the immunotherapeutic agent, and wherein the second time point is after the administration of the immunotherapeutic agent. In some embodiments, the immunotherapeutic agent is administered before the labeled CD8 binding agent, wherein the first time point is after the administration of the immunotherapeutic agent and after the administration of the labeled CD8 binding agent, and wherein the second time point is after the first time point. In some embodiments, the detecting is carried out within about 1 day or less (e.g., within about 6 hours, 4 hours, 2 hours, 90 minutes, 1 hour, 30 minutes or less) after the administering. In some embodiments, the method is repeated for one or more times, such as about 1 to 4 times per year. In some embodiments, the method is repeated after at least 1 day after the prior administration of the CD8 binding agent. In some embodiments, the subject is monitored for more than 1 year.

Provided herein is a method of identifying gut microbial strains associated with responsiveness to treatment with an immunotherapeutic agent, the method comprising: a) obtaining gut microbiome samples from a population of subjects having cancer, which population comprises subjects who are responsive to treatment with the immunotherapeutic agent and subjects who are not responsive to treatment with the immunotherapeutic agent; b) analyzing the gut microbiome samples of the subjects who are responsive to the treatment and the gut microbiome samples of the subjects who are not responsive to the treatment; and c) identifying gut microbial strains associated with the subjects who are responsive to the treatment; wherein responsiveness is determined by detecting binding of the labeled CD8 binding agent according to (or as applied to) any of the embodiments above to $CD8^+$ T cells in a tumor tissue in the subjects, and wherein the detection of the binding indicates that the subjects are responsive to the immunotherapeutic agent. In some embodiments, the method further comprises preparing a microbiome-based drug comprising gut microbial strains associated with responsiveness to the immunotherapeutic agent. In some embodiments, the immunotherapeutic agent is an anti-PD-1 antibody. In some embodiments, the immunotherapeutic agent is an anti-PD-L1 antibody, such as atezolizumab.

Further provided herein are kits and articles of manufacture comprising the CD8 binding agent according to (or as applied to) any of the embodiments above, such as labeled CD8 binding agent. In some embodiments, the kit or article of manufacture comprises an instruction for use of the CD8 binding agent according to any of the methods described above.

BRIEF DESCRIPTION OF THE DRAWINGS

FIG. 2 provides an alignment of the amino acid sequences of human CD8a (SEQ ID NO: 13), cynomolgus CD8a (SEQ ID NO: 14), and rhesus CD8a (SEQ ID NO: 15).

DETAILED DESCRIPTION

Figure 1:
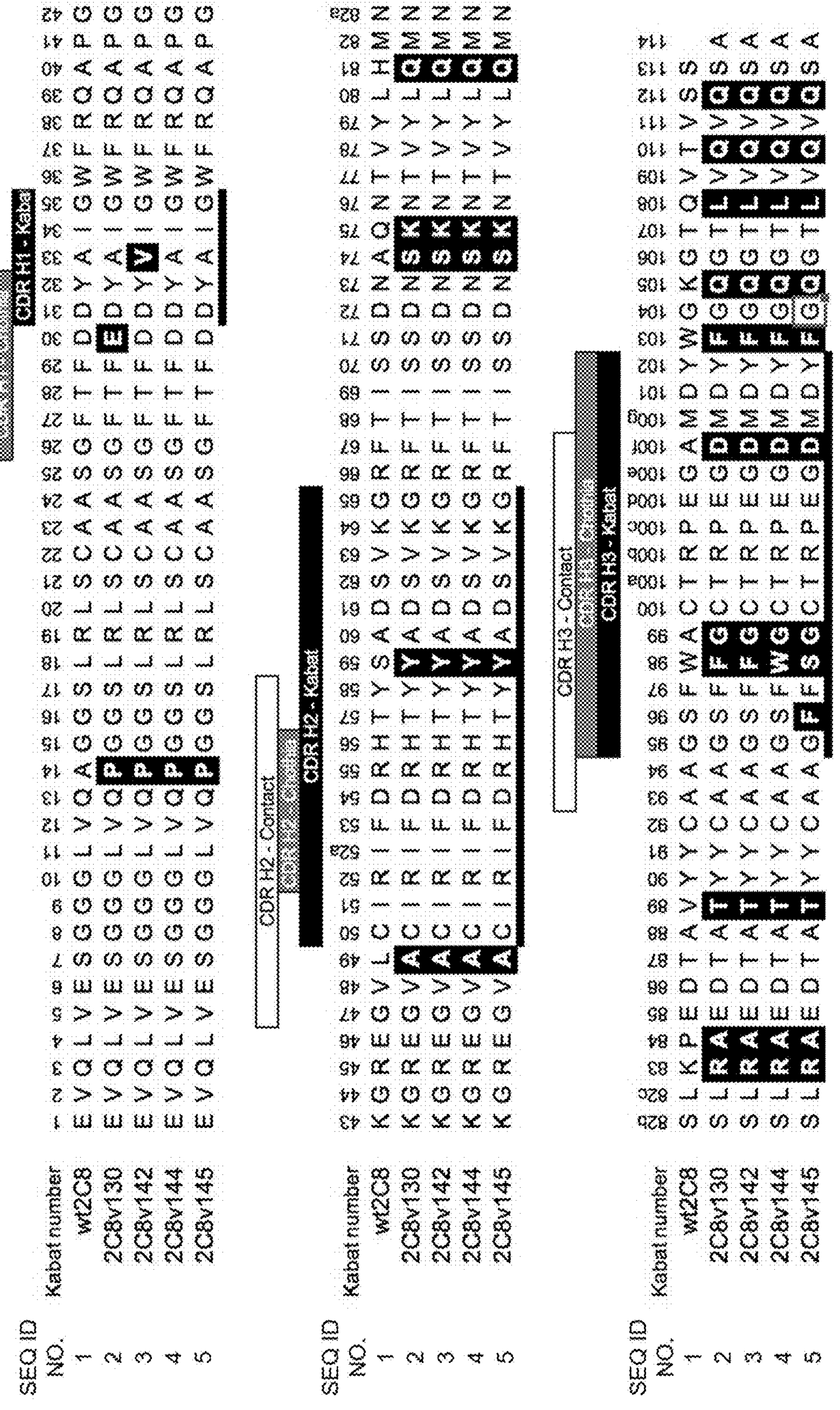
FIG. 1 provides an alignment of the amino acid sequences of exemplary anti-CD8 VHH domains, including llama VHH wt2C8 (SEQ ID NO: 1), humanized VHHs hu2C8v130 (SEQ ID NO: 2), hu2C8v142 (SEQ ID NO: 3) and hu2C8v144 (SEQ ID NO: 4), and non-binding control 2C8v145 (SEQ ID NO: 5).

Provided herein are CD8 binding agents (including anti-CD8 antibodies or antigen-binding fragments thereof) comprising a VHH domain, wherein the CD8 binding agent specifically binds human CD8 with high affinity but do not stimulate or inhibit $CD8^+$ T cell or induce $CD8^+$ T cell proliferation. The CD8 binding agents are capable of binding CD8 in non-human primates, such as rhesus and cynomolgus monkeys, with high affinity. Compared to CD8 binding agents based on traditional 4-chain antibodies, the CD8 binding agents described herein have higher permeability and shorter serum half-life. Thus, the CD8 binding agents described herein are suitable for detecting the presence, localization, and/or quantities of $CD8^+$ cells (e.g., $CD8^+$ T cells) within a short timeframe (e.g., within 1 day such as within 1 hour) post dosing, allowing same-day readout, repeated imaging and multiplexed imaging in combination with other biomarkers. Additionally, the CD8 binding agents described herein show high sensitivity to CD8, linear correlation with CD8 levels over a large dynamic range, high precision due to reduced sensitivity to extraneous factors such as permeability, and high image quality as reflected in high tumor to blood ratios in mouse xenograft models.

Provided herein are methods of using the CD8 binding agents in methods for detecting $CD8^+$ T-cells in vivo. Also provided are methods of using the CD8 binding agents herein in methods of predicting the responsiveness of a subject having a disease (e.g., cancer, autoimmune disease or condition, transplant rejection, or graft-versus-host disease) to treatment with an immunotherapeutic agent. In addition, provided are methods of using the CD8 binding agents herein to monitor disease progress and/or treatment progress in a subject having a disease (e.g., cancer, autoimmune disease or condition, transplant rejection, or graft-versus-host disease) who is receiving treatment with an immunotherapeutic agent.

Definitions

The term "human CD8" herein refers to a protein, polypeptide, or portions thereof that corresponds to cluster of differentiation 8 molecule in human. The full-length human CD8 is a transmembrane glycoprotein that serves as a co-receptor for the T cell receptor. The human CD8 protein is a dimer, consisting of a pair of CD8 chains, including CD8α and CD8β chains. The term "human CD8" encompasses CD8α/CD8α homodimer, CD8α/CD8β heterodimer, CD8α chain, CD8β chain, or portions thereof, such as extracellular domain(s). "CD8a" and "CD8α" are used interchangeably herein, and "CD8b" and "CD8β" are used interchangeably herein. An exemplary sequence of the human CD8α chain is shown in FIG. 2.

The term "CD8 binding agent" herein refers to any CD8 binding molecule. The CD8 binding agent may be a polypeptide, a protein, an antibody (including a 4-chain antibody, or a heavy chain antibody), an antibody fragment (e.g., VHH), or an immunoconjugate that binds to human CD8, cynomolgus CD8, and/or other non-human CD8 proteins or peptides. The CD8 binding agent may also comprise a label such as a small molecule label, e.g., a radionuclide. A CD8 binding agent that comprises a label is also referred herein as a "labeled CD8 binding agent".

The term "antibody" herein is used in the broadest sense and encompasses various antibody structures, including but not limited to monoclonal antibodies, monovalent antibodies (e.g., one-armed antibodies), 4-chain antibodies (such as IgG antibodies), heavy chain antibodies, and antibody fragments thereof so long as they exhibit the desired antigen-binding activity, i.e., binding to CD8 (such as a human CD8, a cynomolgus CD8, and/or a rhesus CD8). The terms "4-chain antibody" are used herein interchangeably to refer to an antibody or antigen-binding fragments having two heavy chains and two light chains.

"Antibody fragments" comprise a portion of an antibody, preferably the antigen binding or variable region of the antibody. Examples of antibody fragments include VHHs, single-domain antibodies, Fab, Fab', $F(ab')_2$, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. The term "constant domain" refers to the portion of an immunoglobulin molecule having a more conserved amino acid sequence relative to the other portion of the immunoglobulin, the variable domain, which contains the antigen-binding site. The constant domain contains the $C_H1$, $C_H2$ and $C_H3$ domains (collectively, $C_H$) of the heavy chain and the CHL (or $C_L$) domain of the light chain.

The term "Fc region" or "fragment crystallizable region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations, which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present application may be made by a variety of techniques, including, for example, the hybridoma method (e.g., Kohler and Milstein, *Nature,* 256:495-97 (1975); Hongo et al., *Hybridoma,* 14 (3): 253-260 (1995), Harlow et al., *Antibodies: A Laboratory Manual*, (Cold Spring Harbor Laboratory Press, $2^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "heavy chain antibody," also known as "heavy chain-only antibodies" or "HCAb" refers to a functional antibody, which comprises two heavy chains, but lacks two light chains usually found in 4-chain antibodies. Camelid animals (such as camels, llamas, or alpacas) are known to produce HCAbs.

The term "single-domain antibody" or "sdAb" refers to a single antigen-binding domain having three complementarity determining regions (CDRs). The sdAb alone is capable of binding to the antigen without pairing with a corresponding CDR-containing polypeptide. In some cases, single-domain antibodies are engineered from camelid HCAbs and are referred to as "VHHs" (defined below). Camelid sdAb is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)).

The term "VHH" or "variable domain of the heavy chain of a heavy chain antibody" refers to a single, heavy chain variable domain of a heavy chain antibody. VHH molecules can be derived from antibodies raised in Camelidae species, for example, camel, llama, vicuna, dromedary, alpaca and guanaco. A basic VHH has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, 4-chain antibodies and antigen-binding antibody fragments thereof comprise six HVRs: three in the VH (H1, H2, H3), and three in the VL (L1, L2, L3). Generally, heavy-chain antibodies comprise three HVRs (HVR1, HVR2, HVR3).

A number of HVR delineations are in use and are encompassed herein. Exemplary HVRs for 4-chain antibodies and antigen-binding antibody fragments thereof herein include: (a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987)); (b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, MD (1991)); (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

The amino acid residues of a single-domain antibody (such as VHH) can be numbered according to the general numbering for $V_H$ domains given by Kabat et al. ("Sequence of proteins of immunological interest", US Public Health Services, NIH Bethesda, Md., Publication No. 91), as applied to VHH domains from Camelids in the article of Riechmann and Muyldermans, J. Immunol. Methods 2000 Jun. 23; 240 (1-2): 185-195. According to this numbering, FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113. In this respect, it should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering).

"Framework" or "FR" residues are those variable-domain residues other than the HVR residues as herein defined.

The term "chimeric" antibody refers to an antibody in which a portion of the heavy and/or light chain is identical to or derived from a particular source or species, while the remainder of the heavy and/or light chain is identical to or derived from a different source or species.

"Humanized" antibodies are antibodies that contain minimal sequence derived from the non-human antibody. Generally, humanized antibodies are human immunoglobulins (recipient antibody) in which residues from a hypervariable region of the recipient are replaced by residues from a hypervariable region of a non-human species (donor antibody) such as camelid, mouse, rat, rabbit or non-human primate having the desired antibody specificity, affinity, and capability. In certain aspects, a "humanized" antibody refers to a chimeric antibody comprising amino acid residues from non-human (e.g., camelid) CDRs and amino acid residues from human FRs. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. For further details, see Jones et al., *Nature* 321:522-525 (1986); Riechmann et al., Nature 332:323-329 (1988); and Presta, Curr. Op. Struct. Biol. 2:593-596 (1992).

An "affinity-matured" antibody is one with one or more alterations in one or more CDRs thereof that result in an improvement in the affinity of the antibody for antigen, compared to a parent antibody that does not possess those alteration(s). In some embodiments, an affinity-matured antibody has nanomolar or even picomolar affinities for the target antigen. Affinity-matured antibodies are produced by procedures known in the art. For example, random mutagenesis of CDR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, California. The ALIGN-2 program should be compiled for use on a UNIX operating system, preferably digital UNIX V4.0D. All sequence comparison parameters are set by the ALIGN-2 program and do not vary.

The term "specific binding" or "specifically binds" or is "specific for" a particular polypeptide or an epitope on a particular polypeptide target as used herein can be exhibited, for example, by a molecule having a $K_D$ for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In some embodiments, the term "specific binding" refers to binding where a molecule binds a particular polypeptide or epitope on a particular polypeptide without substantially binding to any other polypeptide or polypeptide epitope. $K_D$ can be determined by methods known in the art, such as ELISA, surface plasmon resonance (SPR), fluorescence activated cell sorting (FACS) analysis, or radioimmunoprecipitation (RIA). Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target.

As used herein, "treatment" or "treating" is an approach for obtaining beneficial or desired results including clinical results. For purposes of this application, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods provided herein contemplate any one or more of these aspects of treatment.

An "effective amount" of a CD8 binding agent or composition as disclosed herein is an amount sufficient to carry out a specifically stated purpose, e.g., for imaging $CD8^+$ T-cells in vivo. An "effective amount" can be determined empirically and by known methods relating to the stated purpose (such as imaging $CD8^+$ T-cells in vivo).

The term "therapeutically effective amount" refers to an amount of, e.g., an immunotherapeutic agent (such as an immunotherapeutic agent described elsewhere herein), a cell therapy, or a cancer vaccine, effective to "treat" a disease or disorder in a subject (e.g., a mammal, such as a human). In the case of cancer, the therapeutically effective amount of the immunotherapeutic agent, cell therapy or cancer vaccine can reduce the number of cancer cells; reduce the tumor size or weight; inhibit (e.g., slow to some extent and preferably stop) cancer cell infiltration into peripheral organs; inhibit (e.g., slow to some extent and preferably stop) tumor metastasis; inhibit, to some extent, tumor growth; and/or relieve to some extent one or more of the symptoms associated with the cancer. To the extent the immunotherapeutic agent, cell therapy or cancer vaccine can prevent growth and/or kill existing cancer cells, it can be cytostatic and/or cytotoxic. In some embodiments, the therapeutically effective amount is a growth inhibitory amount. In another embodiment, the therapeutically effective amount is an amount that extends the survival of a patient. In another embodiment, the therapeutically effective amount is an amount that improves progression free survival of a patient.

An "individual" or "subject" is a mammal. Mammals include, but are not limited to, domesticated animals (e.g., cows, sheep, cats, dogs, and horses), primates (e.g., humans and non-human primates such as rhesus and cynomolgus monkeys), rabbits, and rodents (e.g., mice and rats). In some embodiments, the individual or subject is a human.

As used herein, "responsiveness" refers to the development of a favorable response when a subject is undergoing or has undergone treatment with a therapeutic agent (e.g., an immunotherapeutic agent). An example of a favorable response is inhibition of tumor growth in a subject during or following treatment with a therapeutic agent (e.g., an immunotherapeutic agent), whereas an example of an unfavorable is continued growth or accelerated growth of a tumor in a subject during or following treatment with a therapeutic agent (e.g., an immunotherapeutic agent).

As used herein "monitoring disease progression" refers to assessing a subject (e.g., a subject diagnosed with cancer, autoimmune disease or condition, transplant rejection, or graft-versus-host disease) at successive time intervals to determine whether disease symptoms have worsened, stabilized, or improved (i.e., become less severe). For example, monitoring the progression of cancer in a subject can, in certain instances, include monitoring changes in the weight or size of a tumor (such as tumor regression or tumor grown), time to progression, duration of survival, length of progression-free survival, overall response rate, duration of response, quality of life, expression and/or activity of disease markers (e.g., expression of certain genes and/or proteins), or other criteria known in the art. Additional approaches to monitoring disease progression in a patient with cancer can be employed, including for example, measurement of response to treatment via imaging techniques, which are described in further detail elsewhere herein.

As used herein "monitoring treatment progress" refers to assessing a subject (e.g., a subject diagnosed with cancer, autoimmune disease or condition, transplant rejection, or graft-versus-host disease) at successive time intervals during or following treatment (e.g., treatment with an immunotherapeutic agent) to determine whether disease symptoms have worsened, stabilized, or improved (i.e., become less severe) as a result of the treatment. For example, treatment progress in a subject (e.g., a subject who has or is receiving treatment with an immunotherapeutic agent) can be monitored using the same criteria as those used to monitor disease progression.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

As used herein "in conjunction with" refers to the timing of the administration of, e.g., a CD8 binding agent described herein, relative to the administration of a second agent, e.g., an immunotherapeutic agent, or another diagnostic imaging agent. For example, administration of a CD8 binding agent described herein in conjunction with an immunotherapeutic agent means that the CD8 binding agent may be administered before the immunotherapeutic agent has been administered, after the immunotherapeutic agent has been administered, concurrently with the administration of the immunotherapeutic agent, or simultaneously with the administration of the immunotherapeutic agent. Additional agents may be administered before or after the CD8 binding agent and the immunotherapeutic agent are administered. Additionally or alternatively, other agents may be administered between the sequential administration of the CD8 binding agent and the immunotherapeutic agent.

The term "detecting" is intended to include determining the presence or absence of a substance or quantifying the amount of a substance (such as CD8). The term thus refers to the use of the materials, compositions, and methods of the present application for qualitative and quantitative determinations. In general, the particular technique used for detection is not critical for practice of the methods in the present application. For example, "detecting" according to the methods described herein may include: observing the presence or absence of a CD8 polypeptide or a change in the levels of a CD8 polypeptide. In some embodiments, "detecting" may include detecting wild type CD8 levels (e.g., mRNA or polypeptide levels). Detecting may include quantifying a change (increase or decrease) of any value between 10% and 90%, or of any value between 30% and 60%, or over 100%, when compared to a control. Detecting may include quantifying a change of any value between 2-fold to 10-fold, inclusive, or more e.g., 100-fold.

The word "label" when used herein refers to a detectable compound or composition, which is conjugated directly or indirectly to the antibody (e.g., VHH). The label may itself be detectable by itself (e.g., radioisotope labels or fluorescent labels) or, in the case of an enzymatic label, may catalyze chemical alteration of a substrate compound or composition, which is detectable.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X".

It is understood that aspects and embodiments of the present application include "comprising," "consisting," and "consisting essentially of" aspects and embodiments.

As used herein and in the appended claims, the singular forms "a," "an," and "the" include plural referents unless the context clearly dictates otherwise.

The term "and/or" as used herein a phrase such as "A and/or B" is intended to include both A and B; A or B; A (alone); and B (alone). Likewise, the term "and/or" as used herein a phrase such as "A, B, and/or C" is intended to encompass each of the following embodiments: A, B, and C; A, B, or C; A or C; A or B; B or C; A and C; A and B; B and C; A (alone); B (alone); and C (alone).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the CD8 binding agents and methods of use thereof are specifically embraced by the present invention and are disclosed herein just as if each and every combination were individually and explicitly disclosed herein.

CD8 Binding Agents a. Functional Characteristics

A CD8 binding agent provided herein comprise a VHH domain (e.g., a camelid or humanized VHH) and has one or more of following characteristics: (a) the CD8 binding agent specifically binds a human CD8 with a $K_D$ of about 1 nM or less; (b) the CD8 binding agent binds human CD8 with a $k_{off}$ of about 0.002/s or less (e.g., about 0.0018/s, or about 0.00085/s); (c) the CD8 binding agent binds cynomolgus CD8 with a $K_D$ of about 1 nM or less; (d) the CD8 binding agent binds cynomolgus CD8 with a $k_{off}$ of about 0.004/s or less (e.g., about 0.0037/s, or about 0.0019/s); (e) the CD8 binding agent does not inhibit or stimulate the activation of $CD8^+$ T cells; (f) the CD8 binding agent does not induce $CD8^+$ T cell proliferation; and (g) the CD8 binding agent does not bind $CD4^+$ cells. In some embodiments, the VHH domain has one or more characteristics of the CD8 binding agent described herein. In some embodiments, the labeled VHH domain (i.e., the VHH domain conjugated to a detectable label) has one or more characteristics of the CD8 binding agent described herein.

The CD8 binding agent described herein binds CD8 with high affinity and specificity. In some embodiments, the CD8 binding agent binds human CD8 with a $K_D$ of about 1 nM, 0.5 nM, 0.4 nM, 0.3 nM, 0.25 nM, 0.2 nM, 0.15 nM, 0.1 nM, 0.05 nM, 0.02 nM, 0.01 nM, 0.001 nM or less (e.g., $10^{-9}$ M or less, e.g., from $10^{-9}$ M to $10^{-13}$ M, or from $10^{-10}$ M to $10^{-12}$ M), including any value or range in between these values. In some embodiments, the CD8 binding agent binds rhesus CD8 with a $K_D$ of about 1 nM, 0.5 nM, 0.4 nM, 0.3 nM, 0.25 nM, 0.2 nM, 0.15 nM, 0.1 nM, 0.05 nM, 0.02 nM, 0.01 nM, 0.001 nM or less (e.g., $10^{-9}$ M or less, e.g., from $10^{-9}$ M to $10^{-13}$ M, or from $10^{-10}$ M to $10^{-12}$ M), including any value or range in between these values. In some embodiments, the CD8 binding agent binds cynomolgus CD8 with a $K_D$ of 1 nM, 0.5 nM, 0.4 nM, 0.3 nM, 0.25 nM, 0.2 nM, 0.15 nM, 0.1 nM, 0.05 nM, 0.02 nM, 0.01 nM, 0.001 nM or less (e.g., $10^{-9}$ M or less, e.g., from $10^{-9}$ M to $10^{-13}$ M, or from $10^{-10}$ M to $10^{-12}$ M), including any value or range in between these values. In some embodiments, the CD8 binding agent binds (a) human CD8 with a $K_D$ of about 1 nM, 0.5 nM, 0.4 nM, 0.3 nM, 0.25 nM, 0.2 nM, 0.15 nM, 0.1 nM, 0.05 nM, 0.02 nM, 0.01 nM, 0.001 nM or less (e.g., $10^{-9}$ M or less, e.g. from $10^{-9}$ M to $10^{-13}$ M, or from $10^{-10}$ M to $10^{-12}$ M), including any value or range in between these values; (b) rhesus CD8 with a $K_D$ of about 1 nM, 0.5 nM, 0.4 nM, 0.3 nM, 0.25 nM, 0.2 nM, 0.15 nM, 0.1 nM, 0.05 nM, 0.02 nM, 0.01 nM, 0.001 nM or less (e.g., $10^{-9}$ M or less, e.g., from $10^{-9}$ M to $10^{-13}$ M, or from $10^{-10}$ M to $10^{12}$ M), including any value or range in between these values, and (c) cynomolgus CD8 with a $K_D$ of about 1 nM, 0.5 nM, 0.4 nM, 0.3 nM, 0.25 nM, 0.2 nM, 0.15 nM, 0.1 nM, 0.05 nM, 0.02 nM, 0.01 nM, 0.001 nM or less (e.g., $10^{-9}$ M or less, e.g., from $10^{-9}$ M to $10^{-13}$ M, or from $10^{-10}$ M to $10^{-12}$ M), including any value or range in between these values. In some embodiments, the CD8 binding agent binds human CD8 with a $K_D$ of about 150 pM or less, and the CD8 binding agent binds cynomolgus monkey CD8 with a $K_D$ of about 350 pM or less. In some embodiments, the CD8 binding agent binds human CD8 with a $K_D$ of about 132 pM, and the CD8 binding agent binds cynomolgus monkey CD8 with a $K_D$ of about 344 pM. In some embodiments, the CD8 binding agent binds human CD8 with a $K_D$ of about 50 pM or less, and the CD8 binding agent binds cynomolgus monkey CD8 with a $K_D$ of about 150 pM or less. In some embodiments, the CD8 binding agent binds human CD8 with a $K_D$ of about 50 pM, and the CD8 binding agent binds cynomolgus monkey CD8 with a $K_D$ of about 137 pM. In some embodiments, the CD8 is CD8α. In some embodiments, the CD8 is CD8α/CD8α homodimer. In some embodiments, the CD8 is CD8α/CD8β heterodimer.

In some embodiments, the CD8 binding agent binds human CD8 with a $k_{off}$ of about 0.01/s, 0.005/s, 0.004/s, 0.003/s, 0.002/s, 0.0015/s, 0.001/s, 0.0005/s, 0.0002/s, 0.0001/s or less (e.g., $10^{-2}$/s or less, e.g., from $10^{-5}$/s to $10^{-2}$/s, or from $10^{-4}$ to $10^{-3}$/s), including any value or range in between these values. In some embodiments, the CD8 binding agent binds rhesus CD8 with a $k_{off}$ of about 0.01/s, 0.005/s, 0.002/s, 0.001/s, 0.0005/s, 0.004/s, 0.003/s, 0.002/s, 0.0015/s, 0.001/s, 0.0005/s or less (e.g., $10^{-2}$/s or less, e.g., from $10^{-5}$/s to $10^{-2}$/s, or from $10^{-4}$ to $10^{-3}$/s), including any value or range in between these values. In some embodiments, the CD8 binding agent binds cynomolgus CD8 with a $k_{off}$ of about 0.01/s, 0.005/s, 0.002/s, 0.001/s, 0.0005/s, 0.004/s, 0.003/s, 0.002/s, 0.0015/s, 0.001/s, 0.0005/s or less (e.g., $10^{-2}$/s or less, e.g., from $10^{-5}$/s to $10^{-2}$/s, or from $10^{-4}$ to $10^{-3}$/s), including any value or range in between these values. In some embodiments, the CD8 binding agent binds (a) human CD8 with a $k_{off}$ of about 0.01/s, 0.005/s, 0.004/s, 0.003/s, 0.002/s, 0.0015/s, 0.001/s, 0.0005/s, 0.0002/s, 0.0001/s or less (e.g., $10^{-2}$/s or less, e.g., from $10^{-5}$/s to $10^{-2}$/s, or from $10^{-4}$ to $10^{-3}$/s), including any value or range in between these values; (b) rhesus CD8 with a $k_{off}$ of about 0.01/s, 0.005/s, 0.002/s, 0.001/s, 0.0005/s, 0.004/s, 0.003/s, 0.002/s, 0.0015/s, 0.001/s, 0.0005/s or less (e.g., $10^{-2}$/s or less, e.g., from $10^{-5}$/s to $10^{-2}$/s, or from $10^{-4}$ to $10^{-3}$/s), including any value or range in between these values; (c) cynomolgus CD8 with a $k_{off}$ of about 0.01/s, 0.005/s, 0.002/s, 0.001/s, 0.0005/s, 0.004/s, 0.003/s, 0.002/s, 0.0015/s, 0.001/s, 0.0005/s or less (e.g., $10^{-2}$/s or less, e.g., from $10^{-5}$/s to $10^{-2}$/s, or from $10^{-4}$ to $10^{-3}$/s), including any value or range in between these values. In some embodiments, the CD8 binding agent binds human CD8 with a $k_{off}$ of about 0.002/s or less, and the CD8 binding agent binds cynomolgus monkey CD8 with a $k_{off}$ of about 0.004/s or less. In some embodiments, the CD8 binding agent binds human CD8 with a $k_{off}$ of about 0.0018/s, and the CD8 binding agent binds cynomolgus monkey CD8 with a $k_{off}$ of about 0.0037/s. In some embodiments, the CD8 binding agent binds human CD8 with a $k_{off}$ of about 0.001/s, and the CD8 binding agent binds cynomolgus monkey CD8 with a $k_{off}$ of about 0.002/s. In some embodiments, the CD8 binding agent binds human CD8 with a $k_{off}$ of about 0.00085/s, and the CD8 binding agent binds cynomolgus monkey CD8 with a $k_{off}$ of about 0.0019/s. In some embodiments, the CD8 is CD8α. In some embodiments, the CD8 is CD8α/CD8α homodimer. In some embodiments, the CD8 is CD8α/CD8β heterodimer.

In some embodiments, the CD8 binding agent binds a human CD8 with a CD8-binding half-life (e.g., in an in vitro binding assay) of about 30 minutes, 1 hour, 2 hours, 3 hours, 4 hours or more (e.g., at least 15 minutes, e.g., from 15 minutes to 6 hours, or from 30 minutes to 2 hours), including any value or range in between these values. In some embodiments, the CD8 binding agent binds a rhesus CD8 with a CD8-binding half-life of about 30 minutes, 1 hour, 2 hours, 3 hours, 4 hours or more (e.g., at least 15 minutes, e.g., from 15 minutes to 6 hours, or from 30 minutes to 2 hours), including any value or range in between these values. In some embodiments, the CD8 binding agent binds a cynomolgus CD8 with a CD8-binding half-life of about 30 minutes, 1 hour, 2 hours, 3 hours, 4 hours or more (e.g., at least 15 minutes, e.g., from 15 minutes to 6 hours, or from 30 minutes to 2 hours), including any value or range in between these values.

The $K_D$ and $k_{off}$ of the CD8 binding agents provided herein for human CD8, rhesus CD8 and/or cynomolgus CD8 can be determined by any method known in the art, including, but not limited to, e.g., ELISA, fluorescence activated cell sorting (FACS) analysis, radioimmunoprecipitation (RIA), and surface plasmon resonance (SPR). In some embodiments, the $K_D$ and/or $k_{off}$ of a CD8 binding agent provided herein for human CD8, rhesus CD8 and/or cynomolgus CD8 is determined via SPR. In some embodiments, the $K_D$ and/or $k_{off}$ of a CD8 binding agent provided herein is determined by surface plasmon resonance (SPR) using a CD8α/CD8β-Fc fusion protein as a reagent. In some embodiments, the CD8α/CD8β-Fc fusion protein is a one-armed human CD8α/human CD8β-Fc fusion protein. In some embodiments, the CD8α/CD8β-Fc fusion protein is a one-armed cynomolgus CD8α/cynomolgus CD8β-Fc fusion protein. In some embodiments, the one-armed CD8α/CD8β-Fc fusion protein comprises a single-chain polypeptide comprising human CD8α and human CD8β, which is fused to one polypeptide chain of an Fc. In some embodiments, the one-armed CD8α/CD8β-Fc fusion protein comprises a single-chain polypeptide comprising cynomolgus CD8α and cynomolgus CD8β, which is fused to one polypeptide chain of an Fc. In some embodiments, the $K_D$ of a CD8 binding agent provided herein for human CD8, rhesus CD8 and/or cynomolgus CD8 is determined via FACS. Exemplary human, rhesus, and cynomolgus CD8α amino acid sequences are shown in FIG. 2.

In some embodiments, the CD8 binding agent provided herein does not bind (e.g., specifically bind) mouse CD8. In some embodiments, the CD8 binding agent does not bind (e.g., specifically bind) rat CD8. In some embodiments, the CD8 binding agent does not bind (e.g., specifically bind) to either mouse CD8 or rat CD8, e.g., as determined via SPR and/or FACS.

The characteristics of the CD8 binding agents described herein can be assessed using well known methods, e.g., methods used in the Examples below. In some embodiments, $CD8^+$ T cell proliferation is assessed in vitro in the presence of peripheral blood mononuclear cells (PBMCs), and a CD8 binding agent provided herein. In some embodiments, $CD8^+$ T cell proliferation is assessed in vitro in the presence of PBMCs, an anti-CD3 antibody, an anti-CD28 antibody, and a CD8 binding agent provided herein. In some embodiments, $CD8^+$ T cell proliferation is assessed in vitro in the presence of PBMCs stimulated with *Staphylococcus* enterotoxin B (SEB), and a CD8 binding agent provided herein. In some embodiments, $CD8^+$ T cell proliferation is assessed in vitro in the presence of PBMCs stimulated with CEF peptide pool, and a CD8 binding agent provided herein. In some embodiments, $CD8^+$ T cell proliferation is assessed in vitro in the presence of PBMCs stimulated with lipopolysaccharide (LPS), and a CD8 binding agent provided herein. In some embodiments, the in vitro assay is performed using 10% FBS as medium. In some embodiments, the in vitro assay is performed using 10% autologous donor plasma as medium, wherein the donor plasma and the PBMCs are obtained from the same donor.

In some embodiments, the CD8 binding agent provided herein does not bind (e.g., specifically bind) to human $CD4^+$ T cells. In some embodiments, the CD8 binding agent provided herein does not bind (e.g., specifically bind) to human $CD3^-$ cells. In some embodiments, the CD8 binding agent provided herein does not bind (e.g., specifically bind) to either human $CD4^+$ T cells or human $CD3^-$ cells. In some embodiments, the lack of specific binding by the CD8 binding agent provided herein to human CD4+ T cells or human CD3− cells is detected via fluorescence activated cell sorting (FACS), as discussed in the Examples.

Provided herein are exemplary CD8 binding agents (including anti-CD8 antibodies and antibody fragments thereof) having one or more of the functional characteristics described above. In some embodiments, provided is a CD8 binding agent comprising a VHH domain that specifically binds a human CD8a epitope comprising Arg25, Lys42, Gln44, Val45, Leu46, Leu47, Ser48, Pro50, Thr51, Ser52, Gln75, Arg93, Leu94, Gly95, Asp96, and Thr97, wherein the amino acid numbering is according to SEQ ID NO: 13. Also provided is a human CD8α epitope comprising Arg25, Lys42, Gln44, Val45, Leu46, Leu47, Ser48, Pro50, Thr51, Ser52, Gln75, Arg93, Leu94, Gly95, Asp96, and Thr97, wherein the amino acid numbering is according to SEQ ID NO: 13. In some embodiments, the amino acid residues in the human CD8α epitope are within about 4.5 Å from one or more amino acid residues of the VHH domain in a crystal structure of the CD8 binding agent or the VHH domain bound to the human CD8α. Further provided is an anti-CD8 antibody that competitively binds the same human CD8α epitope as any one of the CD8 binding agents (e.g., anti-CD8 VHHs) described herein.

In some embodiments, the CD8 binding agent provided herein comprises a camelid VHH domain that specifically binds human CD8. In some embodiments, the CD8 binding agent provided herein comprises a humanized VHH domain that specifically binds human CD8.

In some embodiments, provided is a CD8 binding agent comprising a VHH domain comprising at least one, two, or three CDRs in the amino acid sequence set forth in SEQ ID NO: 1, SEQ ID NO: 2, SEQ ID NO: 3 or SEQ ID NO: 4.

In some embodiments, provided is a CD8 binding agent comprising a VHH domain comprising at least one, two, or three CDRs selected from (a) CDR1 comprising the amino acid sequence set forth in SEQ ID NO: 6 or SEQ ID NO: 7; (b) CDR2 comprising the amino acid sequence set forth in SEQ ID NO: 8 or SEQ ID NO: 9; and (c) CDR3 comprising the amino acid sequence set forth in SEQ ID NO: 10, SEQ ID NO: 11, or SEQ ID NO: 12.

In some embodiments, provided is a CD8 binding agent comprising a VHH domain comprising a CDR1 comprising an amino acid sequence of SEQ ID NO: 6 or SEQ ID NO: 7; a CDR2 comprising an amino acid sequence of SEQ ID NO: 8 or SEQ ID NO: 9; and a CDR3 comprising an amino acid sequence of SEQ ID NO: 10, SEQ ID NO: 11, or SEQ ID NO: 12.

In some embodiments, provided is a CD8 binding agent comprising a VHH domain comprising a CDR1, CDR2 and CDR3 in the amino acid sequence of SEQ ID NO: 1.

In some embodiments, provided is a CD8 binding agent comprising a VHH domain comprising a CDR1, CDR2 and CDR3 in the amino acid sequence of SEQ ID NO: 2.

In some embodiments, provided is a CD8 binding agent comprising a VHH domain comprising a CDR1, CDR2 and CDR3 in the amino acid sequence of SEQ ID NO: 3.

In some embodiments, provided is a CD8 binding agent comprising a VHH domain comprising a CDR1, CDR2 and CDR3 in the amino acid sequence of SEQ ID NO: 4.

In some embodiments, provided is a CD8 binding agent comprising a VHH domain comprising a CDR1 comprising the amino acid sequence of SEQ ID NO: 6, a CDR2 comprising the amino acid sequence of SEQ ID NO: 8, and a CDR3 comprising the amino acid sequence of SEQ ID NO: 10.

In some embodiments, provided is a CD8 binding agent comprising a VHH domain comprising a CDR1 comprising the amino acid sequence of SEQ ID NO: 6, a CDR2 comprising the amino acid sequence of SEQ ID NO: 9, and a CDR3 comprising the amino acid sequence of SEQ ID NO: 11.

In some embodiments, provided is a CD8 binding agent comprising a VHH domain comprising a CDR1 comprising the amino acid sequence of SEQ ID NO: 7, a CDR2 comprising the amino acid sequence of SEQ ID NO: 9, and a CDR3 comprising the amino acid sequence of SEQ ID NO: 11.

In some embodiments, provided is a CD8 binding agent comprising a VHH domain comprising a CDR1 comprising the amino acid sequence of SEQ ID NO: 6, a CDR2 comprising the amino acid sequence of SEQ ID NO: 9, and a CDR3 comprising the amino acid sequence of SEQ ID NO: 12.

Exemplary CDR sequences are shown in FIG. 1 and Table 1 below.

TABLE 1

| CDR1 | CDR2 | CDR3 |
|---|---|---|
| DYAIG (SEQ ID NO: 6) | CIRIFDRHTYSADSVKG (SEQ ID NO: 8) | GSFWACTRPEGAMDY (SEQ ID NO: 10) |
| DYVIG (SEQ ID NO: 7) | CIRIFDRHTYYADSVKG (SEQ ID NO: 9) | GSFFGCTRPEGDMDY (SEQ ID NO: 11) |
| | | GSFWGCTRPEGDMDY (SEQ ID NO: 12) |

In some embodiments, the CD8 binding agent comprises a VHH domain comprising L49A, wherein the numbering is according to Kabat numbering. Examples of L49A mutations are shown in SEQ ID Nos: 2-4 in FIG. 1. In some embodiments, the L49A mutation allows purification of the CD8 binding agent using a Protein A column. In some embodiments, the L49A mutation increases the yield of the CD8 binding agent by at least about 2 fold, 5 fold, 10 fold or more.

In some embodiments, the CD8 binding agent comprises a VHH domain comprising one or more framework mutations that reduce immunogenicity of the VHH domain, e.g., reduce binding of the CD8 binding agent to pre-existing anti-VHH antibodies in a subject receiving the CD8 binding agent. In some embodiments, the CD8 binding agent comprises a VHH domain comprising one or more amino acid modifications selected from the group consisting of V89T substitution, T110Q substitution, S112Q substitution and A114 addition, wherein the numbering is according to Kabat numbering. In some embodiments, the VHH domain comprises V89T substitution, T110Q substitution, S112Q substitution and A114 addition, wherein the numbering is according to Kabat numbering. Examples of these mutations are shown in SEQ ID NOs: 2-4 in FIG. 1. In some embodiments, the framework mutations reduce immunogenicity of the CD8 binding agent by at least about 2 fold, 10 fold, 100 fold, 1000 fold or more.

In some embodiments, the CD8 binding agent comprises a VHH domain having the amino acid sequence of SEQ ID NO: 1. In some embodiments, the CD8 binding agent comprises a VHH domain having the amino acid sequence of SEQ ID NO: 2. In some embodiments, the CD8 binding agent comprises a VHH domain having the amino acid sequence of SEQ ID NO: 3. In some embodiments, the CD8 binding agent comprises a VHH domain having the amino acid sequence of SEQ ID NO: 4.

Exemplary VHH sequences are shown in FIG. 1.

In some embodiments, the CD8 binding agent provided herein is cleared renally. In some embodiments, the CD8 binding agent provided herein is cleared (such as predominantly cleared) by the renal system.

In some embodiments, provided are anti-CD8 antibodies. In some embodiments, provided are anti-CD8 heavy chain antibodies comprising any one of the VHH domains described herein. In some embodiments, the anti-CD8 heavy chain antibody comprises an Fc region, such as a camelid or a human Fc region. In some embodiments, the anti-CD8 heavy chain antibody comprises an Fc of an IgG1, IgG2, IgG3 or IgG4, or a variant thereof. In some embodiments, an anti-CD8 antibody provided herein comprises an Fc variant that possesses some but not all effector functions, which make it a desirable candidate for applications in which the half-life of the antibody in vivo is important yet certain effector functions (such as complement and ADCC) are unnecessary or deleterious.

In some embodiments, provided are anti-CD8 antibody fragments, such as anti-CD8 single-domain antibody or anti-CD8 VHH.

In some embodiment, the CD8 binding agent does not comprise an Fc region.

In some embodiments, the CD8 binding agent provided herein comprise one or more nonproteinaceous moieties. The moieties suitable for derivatization of an antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In some embodiments, the CD8 binding agent does not comprise a nonproteinaceous moiety that increases the serum half-life of the agent. In some embodiments, the CD8 binding agent does not comprise a soluble polymer, such as polyethylene glycol (PEG).

b. Variants and Modifications

In some embodiments, amino acid sequence variants of the CD8 binding agents (e.g., anti-CD8 antibodies) described herein are contemplated. For example, it may be desirable to improve the binding affinity and/or other biological properties of the CD8 binding agent. Amino acid sequence variants of the CD8 binding agent may be prepared by introducing appropriate modifications into the nucleotide sequence encoding the protein, or by peptide synthesis. Such modifications include, for example, deletions from, and/or insertions into and/or substitutions of residues within the amino acid sequences (such as in one or more CDRs and/or framework sequences or in the VHH domain) of the CD8 binding agent. Any combination of deletion, insertion, and substitution can be made to arrive at the final construct, provided that the final construct possesses the desired characteristics (e.g., as described elsewhere herein).

"CD8 binding agent variant" means a polypeptide, for example, a CD8 binding agent possessing the desired characteristics described herein comprises a VHH that has at least about 80% amino acid sequence identity with the VHH of a CD8 binding agent described herein. Such CD8 binding agent variants include, for instance, agents wherein one or more amino acid residues are added to or deleted from the VHH domain. Ordinarily, a CD8 binding agent variant will have at least about 80% amino acid sequence identity, alternatively at least about any of 85%, 90%, 95%, 96%, 97%, 98%, or 99% amino acid sequence identity, to a CD8 binding agent described herein. Optionally, variant CD8 binding agents will have no more than one conservative amino acid substitution as compared to a CD8 binding agent sequence provided herein, alternatively no more than about any of 2, 3, 4, 5, 6, 7, 8, 9, or 10 conservative amino acid substitution as compared to a CD8 binding agent sequence provided herein.

In some embodiments, CD8 binding agent variants having one or more amino acid substitutions, insertions, and/or deletions are provided. Sites of interest for substitutional mutagenesis include the HVRs and FRs. Conservative substitutions are shown in Table 2 under the heading of "conservative substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

| Original Residue | Exemplary Substitutions | Conservative Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Ph e(F) | Trp; Leu; Val; He; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the CD8 binding agent variant can be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, Biochemistry second ed., pp. 73-75, Worth Publishers, New York (1975)):

(1) non-polar: Ala (A), Val (V), Leu (L), Ile (I), Pro (P), Phe (F), Trp (W), Met (M)

(2) uncharged polar: Gly (G), Ser (S), Thr (T), Cys (C), Tyr (Y), Asn (N), Gln (Q)

(3) acidic: Asp (D), Glu (E)

(4) basic: Lys (K), Arg (R), His(H)

Alternatively, naturally occurring residues may be divided into groups based on common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

In some embodiments, the CD8 binding agent provided herein comprises a VHH domain comprising an amino acid sequence having at least 90%, 91%, 92%, 93%, 94%, 95%, 96%, 97%, 98%, 99%, or 100% sequence identity to the amino acid sequence of SEQ ID NO: 1. In some embodiments, the CD8 binding agent provided herein comprises a VHH domain comprising an amino acid sequence having at least 90%, 91%, 92%, 93%, 94%, 95%, 96%, 97%, 98%, 99%, or 100% sequence identity to the amino acid sequence of SEQ ID NO: 2. In some embodiments, the CD8 binding agent provided herein comprises a VHH domain comprising an amino acid sequence having at least 90%, 91%, 92%, 93%, 94%, 95%, 96%, 97%, 98%, 99%, or 100% sequence identity to the amino acid sequence of SEQ ID NO: 3. In some embodiments, the CD8 binding agent provided herein comprises a VHH domain comprising an amino acid sequence having at least 90%, 91%, 92%, 93%, 94%, 95%, 96%, 97%, 98%, 99%, or 100% sequence identity to the amino acid sequence of SEQ ID NO: 4. In some embodiments, a VHH sequence having at least 90%, 91%, 92%, 93%, 94%, 95%, 96%, 97%, 98%, or 99% identity contains substitutions (e.g., conservative substitutions), insertions, or deletions relative to the reference sequence, but the CD8 binding agent comprising that sequence retains the ability to bind CD8 (e.g., a human CD8, a rhesus CD8, and/or a cynomolgus CD8). In some embodiments, a total of 1 to 10 amino acids have been substituted, inserted and/or deleted in SEQ ID NO: 1, SEQ ID NO: 2, SEQ ID NO: 3, or SEQ ID NO: 4. In some embodiments, substitutions, insertions, or deletions occur in regions outside the CDRs (i.e., in the FRs). In some embodiments, the CD8 binding agent comprises the VHH sequence set forth in SEQ ID NO: 1, SEQ ID NO: 2, SEQ ID NO: 3 or SEQ ID NO: 4, including post-translational modifications of that sequence.

One type of substitutional variant involves substituting one or more hypervariable region residues of a parent antibody (e.g., a llama VHH or a humanized VHH). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VHH being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR3 in particular is often targeted.

In some embodiments, substitutions, insertions, or deletions may occur within one or more CDRs so long as such alterations do not substantially reduce the ability of the CD8 binding agent to CD8. For example, conservative alterations (e.g., conservative substitutions as provided herein) that do not substantially reduce binding affinity may be made in CDRs. Such alterations may be outside of CDRs "hotspots" or SDRs. In some embodiments of the variant VHH sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

c. Immunoconjugates Comprising Detectable Labels

In some embodiments, the CD8 binding agent is an immunoconjugate comprising any one of the anti-CD8 antibodies (e.g., anti-CD8 VHH) described herein conjugated to a detectable label. The term "label" or "detectable label" refers to an atom, molecule, or compound that is useful in diagnosing, detecting or visualizing/imaging a location and/or quantity of a target molecule (such as CD8) on a cell, tissue, organ and the like. Detectable labels that can be used in accordance with the embodiments herein include, but are not limited to, radioactive substances (e.g., radioisotopes, radionuclides, radio labels or radiotracers), dyes (e.g., Indo-Cyanine Green (ICG)), contrast agents, fluorescent compounds or molecules, bioluminescent compounds or molecules, enzymes and enhancing agents (e.g., paramagnetic ions). In addition, some nanoparticles, for example quantum dots and metal nanoparticles can be suitable for use as a detection agent.

Radioactive substances that can be used as detectable labels in accordance with the embodiments herein include, but are not limited to $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{75}Sc$, $^{77}As$, $^{86}Y$, $^{89}Sr$, $^{89}Zr$, $^{90}Y$, $^{90}Nb$, $^{94}Tc$, $^{99}Tc$, $^{99}mTc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-158}Gd$, $^{161}Tb$, $^{166}Dy$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, and $^{225}Ac$. Exemplary Paramagnetic ions substances that can be used as detectable labels include, but are not limited to ions of transition and lanthanide metals (e.g. metals having atomic numbers of 6 to 9, 21 to 29, 42 to 44, or 57 to 71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

When the detectable label is a radioactive metal or paramagnetic ion, in some embodiments, the label can be reacted with a reagent having a long tail with one or more chelating groups attached to the long tail for binding these ions. The long tail can be a polymer such as polylysine, polysaccharide, or other derivatized or derivatizable chains having pendant groups to which a chelating group (i.e., for binding ions) may be bound. Examples of chelating groups that may be used according to the embodiments herein include, but are not limited to, ethylenediaminetetraacetic acid (EDTA), diethylenetriaminepentaacetic acid (DTPA), DOTA, NOIA, NOGADA, NETA, NODA, NOTA, deferoxamine (DfO), DFO* (i.e., DFO-star), DFO-squaramide, porphyrins, polyamines, crown ethers, bis-thiosemicarbazones, polyoximes, and like groups. The chelate can be linked to an anti-CD8 antibody (e.g., anti-CD8 VHH) provided herein by a group that allows formation of a bond to the molecule with minimal loss of immunoreactivity and minimal aggregation and/or internal cross-linking. The same chelates, when complexed with non-radioactive metals (e.g., manganese, iron and gadolinium) are useful for magnetic resonance imaging (MRI), when used along with the CD8 binding agents described herein. Macrocyclic chelates such as NOIA, NOGADA, DOTA, NODA, NOTA, and TETA are of use with a variety of metals and radiometals including, but not limited to, e.g., radionuclides of gallium, yttrium and copper. Other ring-type chelates such as macrocyclic polyethers, which are of interest for stably binding radionuclides, such as Radium-223 for radioactive iodine treatment (RAIT) may be used. In some embodiments, chelating moieties may be used to attach a positron emission tomography (PET) imaging agent, such as an aluminum-$^{18}F$ complex, to a CD8 binding agent provided herein for use in PET analysis. The aluminum-$^{18}F$ complex may be conjugated to a VHH domain via a restrained complexing agent (RESCA), such as a compound of Formula (I):

(I)

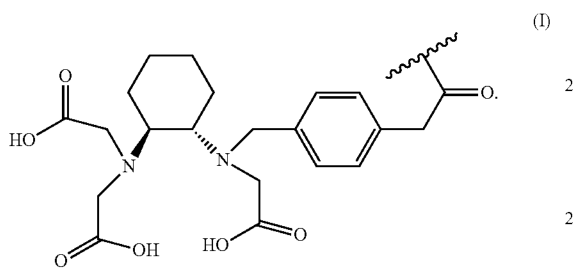

See, for example, US20180273441A1, and Cleeren F. et al. Nature Protocols 13, 2330-2347 (2018).

In some embodiments, there is provided a CD8 binding agent comprises any one of the anti-CD8 VHH domains described herein conjugated to a radionuclide label, such as $^{18}F$. In some embodiments, the VHH domain is conjugated to a label via a chelating moiety. In some embodiments, the chelating moiety is covalently linked to the VHH domain via a lysine residue. In some embodiments, the radionuclide label is comprised in a metal complex. In some embodiments, the radionuclide label forms a complex with a metal, wherein the complex is chelated by the chelating moiety. In some embodiments, the CD8 binding agent comprises an anti-CD8 VHH domain conjugated to a chelating moiety that chelates a complex comprising an $^{18}F$ label and aluminum. In some embodiments, the chelating moiety is a compound of Formula (I).

In some embodiments, there is provided a CD8 binding agent, comprising any one of the anti-CD8 VHH domains described herein conjugated to an [$^{18}F$]-aluminum fluoride complex via a compound of Formula (I).

In some embodiments, there is provided a CD8 binding agent, comprising a VHH domain conjugated to a [$^{18}F$]-aluminum fluoride complex via a compound of Formula (I), wherein the VHH domain comprises a CDR1 comprising the amino acid sequence of SEQ ID NO: 7, a CDR2 comprising the amino acid sequence of SEQ ID NO: 9, and a CDR3 comprising the amino acid sequence of SEQ ID NO: 11. In some embodiments, the VHH domain comprises the amino acid sequence of SEQ ID NO: 3.

In some embodiments, there is provided a CD8 binding agent, comprising a VHH domain conjugated to a [$^{18}F$]-aluminum fluoride complex via a compound of Formula (I), wherein the VHH domain comprises a CDR1 comprising the amino acid sequence of SEQ ID NO: 6, a CDR2 comprising the amino acid sequence of SEQ ID NO: 9, and a CDR3 comprising the amino acid sequence of SEQ ID NO: 12. In some embodiments, the VHH domain comprises the amino acid sequence of SEQ ID NO: 4.

Exemplary contrast agents that can be used as detectable labels in accordance with the embodiments of methods and compositions herein include, but are not limited to, barium, diatrizoate, ethiodized oil, gallium citrate, iocarmic acid, iocetamic acid, iodamide, iodipamide, iodoxamic acid, iogulamide, isohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, thallous chloride, or combinations thereof.

Bioluminescent and fluorescent compounds or molecules and dyes that can be used as detectable labels in accordance with the methods and compositions herein include, but are not limited to, e.g., fluorescein, fluorescein isothiocyanate (FITC), OREGON GREEN™, rhodamine, Texas red, IRDye800CW, ALEXA FLUOR® 647, tetrarhodimine isothiocynate (TRITC), Cy3, Cy5, and the like), fluorescent markers (e.g., green fluorescent protein (GFP), phycoerythrin, and the like), autoquenched fluorescent compounds that are activated by tumor-associated proteases, enzymes (e.g., luciferase, horseradish peroxidase, alkaline phosphatase, and the like), nanoparticles, biotin, digoxigenin or combination thereof.

Enzymes that can be used as detectable labels in accordance with the methods and compositions herein include, but are not limited to, e.g., horseradish peroxidase, alkaline phosphatase, acid phosphatase, glucose oxidase, beta-galactosidase, beta-glucoronidase or beta-lactamase. Such enzymes may be used in combination with a chromogen, a fluorogenic compound or a luminogenic compound to generate a detectable signal.

In some embodiments, the CD8 binding agent provided herein is conjugated to a nanoparticle, i.e., a microscopic particle whose size is measured in nanometers. For example, a nanoparticle is a particle with at least one dimension less than about 100 nm. Nanoparticles can be used as detectable substances because they are small enough to scatter visible light rather than absorb it. For example, gold nanoparticles possess significant visible light extinction properties and appear deep red to black in solution. As a result, CD8 binding agents provided herein that have been conjugated to nanoparticles can be used for the in vivo imaging of T-cells in a subject. At the small end of the size range, nanoparticles are often referred to as clusters. Metal, dielectric, and semiconductor nanoparticles have been formed, as well as hybrid structures (e.g. core-shell nanoparticles). Nanospheres, nanorods, and nanocups are just a few of the shapes that have been grown. Semiconductor quantum dots and nanocrystals are examples of additional types of nanoparticles. Such nanoscale particles, when conjugated to an anti-CD8 antibody (e.g., anti-CD8 VHH) provided herein, can be used as imaging agents for the in vivo detection of T-cells as described herein.

Conjugates of an antibody and a label may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionuclide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used. The immunoconjugates herein include, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A). In some embodiments, the CD8 binding agent provided herein comprises a linker that is a desferrioxamine compound (see, e.g., Vugts et al. (2017) *Eur J Nucl Med Mol Imaging.* 44:286-295 and Rudd et al. (2016) *Chem Commun.* 52: 11859-12000). In some embodiments, the CD8 binding agent provided herein comprises an N-succinyl-desferrioxamine (DFO) linker. In some embodiments, the CD8 binding agent provided herein comprises an anti-CD8 VHH conjugated to a radionuclide (e.g., including, but not limited to $^{89}$Zr, $^{124}$I, or $^{18}$F) by way of a desferrioxamine compound (e.g., N-succinyl-desferrioxamine). In some embodiments, the label is conjugated to the anti-CD8 VHH domain in a site-specific manner, for example, using an enzyme, for example, a sortase or transglutaminase.

In some embodiments, the CD8 binding agent provided herein comprises an anti-CD8 VHH domain directly coupled to a detectable label (i.e., without a linker).

Methods of Producing CD8 Binding Agents

Also provided herein are methods of producing the CD8 binding agents described herein, including methods of producing the anti-CD8 antibodies (e.g., anti-CD8 VHHs), and methods of producing labeled CD8 binding agents.

The anti-CD8 antibodies (e.g., anti-CD8 VHHs) described herein may be produced using recombinant methods and compositions, e.g., as described in U.S. Pat. No. 6,015,695. In some embodiments, isolated nucleic acid encoding an anti-CD8 antibody (e.g., anti-CD8 VHH) described herein is provided. Such nucleic acid may encode an amino acid sequence comprising the anti-CD8 VHH domain. In some embodiments, an isolated nucleic acid encoding an anti-CD8 VHH domain is provided wherein the nucleic acid comprises a sequence having at least 90%, 91%, 92%, 93%, 94%, 95%, 96%, 97%, 98%, 99%, or 100% sequence identity to a nucleic acid sequence that encodes SEQ ID NO:1, SEQ ID NO: 2, SEQ ID NO: 3, or SEQ ID NO: 4

In some embodiments, a vector (e.g., expression vector) comprising a nucleic acid described herein are provided. In some embodiments, a host cell comprising such nucleic acid or vector is provided. In some embodiments, the host cell is eukaryotic, e.g. a Chinese Hamster Ovary (CHO) cell, Expi293 cell, or lymphoid cell (e.g., Y0, NS0, Sp20 cell). In some embodiments, the host cell is prokaryotic, e.g. an *E. coli* cell. In some embodiments, a method of making an anti-CD8 antibody (e.g., anti-CD8 VHH) is provided, wherein the method comprises culturing a host cell comprising a nucleic acid encoding the antibody, as provided above, under conditions suitable for expression of the antibody, and optionally recovering the antibody from the host cell (or host cell culture medium).

Further provided are methods of preparing a labeled CD8 binding agent, comprising conjugating a chelating moiety to any one of the anti-CD8 antibodies (e.g., anti-CD8 VHHs) described herein to provide a conjugate comprising the anti-CD8 antibody and the chelating moiety, and contacting the conjugate with an aluminum fluoride complex comprising $^{18}$F to provide the labeled CD8 binding agent, wherein the chelating moiety is a compound of Formula (I). In some embodiments, the chelating moiety is conjugated to a lysine residue of the anti-CD8 antibody. In some embodiments, the conjugate is contacted with the aluminum fluoride complex in the presence of one or more anti-oxidant compounds. In some embodiments, the one or more anti-oxidant compounds comprise methionine and/or N-acetyl-tryptophan. In some embodiments, the conjugate is contacted with the aluminum fluoride complex in the presence of methionine and N-acetyl-tryptophan. In some embodiments, method comprises purifying the labeled CD8 binding agent from the reaction mixture comprising the conjugate and the aluminum fluoride by a desalting column. In some embodiments, the desalting column is equilibrated with a buffer comprising histidine, methionine, N-acetyl tryptophan, and/or sucrose. In some embodiments, the desalting column is equilibrated with a buffer comprising histidine, methionine, N-acetyl tryptophan, and sucrose.

For recombinant production of an anti-CD8 antibody (e.g., anti-CD8 VHH), nucleic acid encoding an antibody, e.g., as described above, is isolated and inserted into a vector for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, NJ, 2003), pp. 245-254, describing expression of antibody fragments in *E. coli*). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including $DHFR^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

Methods of Detecting, Localizing, and/or Imaging $CD8^+$ Cells Using CD8 Binding Agents Provided herein are methods of detecting, localizing, and/or imaging $CD8^+$ cells using any one of the CD8 binding agents described herein (e.g., anti-CD8 antibody, or an immunoconjugate comprising an anti-CD8 antibody and a detectable label). In some embodiments, the method comprises detecting the presence of CD8 in an in vitro or ex vivo sample. In some embodiments, the method comprises adding the CD8 binding agent to an in vitro or ex vivo sample. Such method, which includes, but is not limited to, e.g., Western blots, immunohistochemical analyses, ELISA assays, and the like, optionally comprises performing a wash following the addition of the CD8 binding agent to the in vitro or ex vivo sample. In some embodiments, detecting the binding of the CD8 binding agent to CD8 comprises detecting the label attached to the anti-CD8 VHH domain. In some embodiments, the method comprises applying a secondary agent that comprises a detectable label herein that binds an anti-CD8:CD8 complex, and detecting the binding of the CD8 binding agent to CD8 comprises detecting the detectable label of the secondary agent. It will be readily understood by those of ordinary skill in the art that the secondary agent does not compete with the CD8 binding agent for binding to CD8, or compete with CD8 for binding to the CD8 binding agent.

In some embodiments, the method comprises detecting, localizing, or imaging the presence of CD8 in vivo. In some embodiments, the method comprises administering the CD8 binding agent described herein to a subject. In some embodiments, the subject is a human. In some embodiments, the subject is a non-human mammal, e.g., a rat, mouse, guinea pig, hamster, rabbit, dog, cat, cow, horse, goat, sheep, donkey, pig, monkey, ape, or other non-human primate. In some embodiments, the non-human primate is a rhesus macaque or a cynomolgus macaque. In some embodiments, the CD8 binding agent is administered orally, topically, or locally to the subject. In some embodiments, the CD8 binding agent is administered to the subject via infusion (such as an intravenous infusion). In some embodiments, the infusion is intraperitoneal. In some embodiments, the CD8 binding agent is administered to the subject by injection, such as intravenous injection or subcutaneous injection. In some embodiments, the method comprises administering the CD8 binding agent to the subject and removing a sample from the subject for analysis (i.e., detection of the binding of the CD8 binding agent to CD8).

In some embodiments, the detection, localization and/or imaging of $CD8^+$ cells is performed in vivo, e.g., using techniques described in further detail elsewhere herein.

In some embodiments, detecting the presence of CD8 in vivo comprises localizing CD8 (such as $CD8^+$ cells) to an organ or a tissue. In some embodiments, the method comprises determining the number of $CD8^+$ cells in an organ or tissue in a subject, such as a diseased tissue. In some embodiments, the subject has cancer, and detecting the presence of CD8 in vivo comprises localizing $CD8^+$ cells to a tumor. In some embodiments, the $CD8^+$ cells are $CD8^+$ T cells, e.g., tumor infiltrating $CD8^+$ T cells. In some embodiments, the method comprises determining the number of $CD8^+$ T cells in a tumor in a subject who has cancer. In some embodiments, the method comprises determining the number of $CD8^+$ T cells in a tumor in a subject who has cancer at multiple successive time points.

In some embodiments, $CD8^+$ cells can be detected, localized, or imaged in vivo within about 1 day or less, such as within about 6 hours, 4 hours, 3 hours, 2 hours, 90 minutes, 1 hour, 30 minutes or less (e.g., about 30 minutes to about 6 hours, about 30 minutes to about 4 hours, or about 2 hours to 4 hours), including any value or range in between these values, after administration of the CD8 binding agent.

In some embodiments, $CD8^+$ cells can be detected, localized, or imaged in vivo using any of the methods described herein for one or more times, such as 1, 2, 3, 4, 5 times or more per year without exceeding the dosimetry guidelines. In some embodiments, the method can be repeated after about 7 days, 6 days, 5 days, 4 days, 3 days, 2 days, 1 day, or less after a first administration of the CD8 binding agent.

In some embodiments, the labeled CD8 binding agent may be used in conjunction with one or more additional imaging agents for multiplexed imaging. In some embodiments, the one or more additional imaging agents may be administered to the subject within a short period of time from the administration of the labeled CD8 binding agent, e.g., as soon as the radioactivity from the first imaging agent has diminished, for example, within about any one of 48 hours, 36 hours, 24 hours, 18 hours, 12 hours, 8 hours, 6 hours, 4 hours, 2 hours, 1 hour or less. In some embodiments, unlike long-lived imaging reagents, the labeled CD8 binding agents described herein enable CD8 imaging to be combined with standard of care PET imaging (e.g., FDG-PET) or novel molecular imaging (e.g., CD4, granzyme B, PSMA), for additional characterization of the immune response. In some embodiments, the method further comprises performing another imaging scan (e.g., PET such as FDG-PET, SPECT, or scintigraphic scan) within about 48 hours from the imaging using the labeled CD8 binding agent.

In some embodiments, the method can be used to detect, localize, or image $CD8^+$ cells in vivo over an extended period of time, such as for at least about 3 months, 6 months, 1 year, 2 years, 3 years, 4 years, 5 years, 10 years or more, including any value or range in between these values. The low immunogenicity of the CD8 binding agents described herein allows repeated and extended use of the CD8 binding agents for imaging and CD8 detection in vivo.

In some embodiments, the method has a sensitivity of about 1 nM, 2 nM, 5 nM, 10 nM, 15 nM, 20 nM, 25 nM, 30 nM, 40 nM, or 50 nM, (e.g., at least about 50 nM, e.g., about 1 nM to about 50 nM, or about 1 nM to about 30 nM), including any value or range in between these values, of CD8 for in vivo CD8 detection. In some embodiments, the method has a linear correlation between the signal from the label and CD8 level in vivo. In some embodiments, the method has a tumor:blood ratio of at least about 2, 3, 4, 5, 6, 7, 8, 9, 10, 11, 12, 13, 14, 15, 20 or higher in a mouse $CD8^+$ tumor (e.g., TALL-1) xenograft model.

Techniques for In Vivo Detection of CD8

In some embodiments, the binding of the CD8 binding agent to CD8 (such as a $CD8^+$ cell, e.g., a $CD8^+$ T cell) in vivo is detected via at least one of: immuno PET (positron emission tomography), SPECT (single-photon emission computed tomography), MRI (magnetic resonance imaging), which is also known as NMR (nuclear magnetic resonance), near-infrared (NIR), or Cerenkov luminescence imaging (CLI). In some embodiments, the binding of the CD8 binding agent to CD8 is detected via two or more forms of imaging. In some embodiments, the binding of the CD8 binding agent to CD8 is detected via near-infrared (NIR) and/or CLI. In some embodiments, the binding of the CD8 binding agent to CD8 is detected via immunoSPECT and/or MR fluorescence. In some embodiments, the binding of the CD8 binding agent to CD8 is detected via immunoSPECT and computer tomography.

Immuno-PET is based on the coincidence detection of an antibody (such as an anti-CD8 antibody provided herein) or fragment thereof labeled with a positron-emitting radionuclide, such as $^{18}F$, $^{64}Cu$, $^{68}Ga$, $^{76}Br$, $^{86}Y$, $^{89}Zr$, and $^{124}I$. Suitable radionuclides for labeling the anti-CD8 antibodies include, but are not limited to, e.g., $^{18}F$, $^{64}Cu$, $^{68}Ga$, $^{76}Br$, $^{86}Y$, $^{88}Y$, $^{89}Zr$, $^{99m}Tc$, $^{111}In$, $^{177}Lu$, $^{123}I$, $^{124}I$, $^{125}I$, and $^{131}I$. The emitted positron will travel a distance of up to a few millimeters, depending on the initial positron energy and the density of the surroundings (see, e.g., Table 2 in Guus et al. (2007) *The Oncologist,* 12: 1379-1389). After having lost its kinetic energy, the positron combines with an electron, leading to the so-called annihilation process, which yields two photons, each with an energy of 511 keV. The two photons are emitted simultaneously in opposite directions. The distribution of a positron-emitting radionuclide-labeled anti-CD8 antibody in a patient can be monitored by detection of the annihilation photon pairs with a PET camera. A PET camera consists of a ring of detectors placed around the body of the patient. If two photons are registered by detectors on opposite sides of the body within a very short time interval (typically 5-15 nanoseconds), it is assumed that somewhere along the line between the two detectors an annihilation event has taken place. By calculating the crossing of all lines, the location of the radiation source (radiolabeled antibody) can be determined. For quantification, PET can provide reliable information when appropriate corrections are performed (see Verel et al. (2005) J Nucl Med, 46 suppl 1:164S-171S). Additional details regarding immuno PET are provided in, e.g., van Dongen et al. (2007) The Oncologist, 12(12): 1379-1389; Reddy et al. (2010) Semin Nucl Med. 40(3): 182-189; Boerman et al. (2011) J. Nucl Med. 52(8): 1171-1172; Santangelo et al. (2015) Nature Methods, 12: 427-432.

ImmunoSPECT imaging entails the administration of an antibody (such as an anti-CD8 antibody provided herein) or fragment thereof labeled with a gamma-emitting radionuclide to a subject, typically through injection into the bloodstream. Examples of gamma-emitting radionuclides include, but are not limited to, e.g., $^{67}Ga$, $^{99m}Tc$, $^{111}In$, $^{123}I$, $^{131}I$, $^{153}Sm$, or $^{186}Re$. Next, a gamma camera is used to acquire multiple 2-D images, from multiple angles. A computer is then used to apply a tomographic reconstruction algorithm to the multiple projections, yielding a 3-D data set. This data set may then be manipulated to show thin slices along any chosen axis of the body, similar to those obtained from other tomographic techniques. To acquire SPECT images, the gamma camera is rotated around the patient. Projections are acquired at defined points during the rotation, typically every 3-6 degrees. In most cases, a full 360-degree rotation is used to obtain an optimal reconstruction. The time taken to obtain each projection is also variable, but 15-20 seconds is typical. This gives a total scan time of 15-20 minutes. In some cases, a SPECT gamma scanner may be built to operate with a conventional CT scanner, with coregistration of images. This allows location of tumors or tissues, which may be seen on SPECT scintigraphy, but are difficult to locate precisely with regard to other anatomical structures. Additional details regarding immunoSPECT can be found in, e.g., Laverman et al. (2015) *J Nucl Med,* 56(5): 778-783; Lutje et al. (2014) *Cancer Res,* 74(21): 6216-6223; Muselaers et al. (2013) *Eur Urology* 64(4): 1101-1106; and others.

The principle of in vivo MRI (magnetic resonance imaging), also known as NMR (nuclear magnetic resonance), is based on manipulating the magnetic properties of the protons and neutrons contained in atomic nuclei present a subject's body (most commonly, those found in the atoms of hydrogen). The motion of these nuclei produces a small magnetic moment. When the subject's body is placed in the magnetic field of the MRI scanner, the magnetic moment of these nuclei aligns with the direction of the magnetic field. A radiofrequency (RF) pulse is then applied to the subject's body in the scanner, which excites the nuclei such that there are transitions between lower and higher energy spin states. Once the RF pulse is given, the nuclei return to their equilibrium state (a process called relaxation), releasing their absorbed extra energy and emitting an RF signal. This signal is detected by the scanner's RF coils and is then used to generate a detailed image of the body's tissues. By using MRI contrast agents, the contrast of this image, and so the visibility of specific body structures, can be improved. Examples of labels that are detectable via MRI include, but are not limited to, e.g., superparamagnetic iron oxides (including iron oxide nanoparticles such as Molday ION Rhodamine-B Carboxyl), $^{19}F$-based probes, paramagnetic metals (e.g., gadolinium, manganese, manganese oxide, dysprosium), (U)SPIO, PARA(CEST), DIA(CEST), and PFCs. Additional information about using labeled antibodies for in vivo MRI and/or labels that are detectable via MRI is discussed in, e.g., Srivastava (2015) *Dis Model Mech.* 8(4): 323-336; Zhou et al. (2013) *Wiley Interdiscip Rev Nanomed Nanobiotechnol.* 5(1): 1-18; Sohn et al. (2015) *Nanomedicine.* 11(1): 127-135; Bates et al. (2014) *PloS* ONE 9(5): e97220; Zhu et al. (2015) Int. J. Mol. Sci. 16: 9573-9587; and Zhang et al. (2014) Int J. Medicine. 9: 33-41.

NIR imaging takes advantage of the deep photon penetration of near infrared light into living tissue to provide imaging of endogenous and/or exogenous contrast at depths of <1 cm. Within this field, MR fluorescence imaging focuses on the detection of an antibody labeled with an exogenous contrast agent that emits fluorescence between 700 and 900 nm. The typical fluorescence imaging system has been described in detail elsewhere (De Grand et al. (2003) *Technol Cancer Res Treat,* 2:553-62; Nakayama et al. (2002) *Mol Imaging,* 1:365-77; Ntziachristos et al. (2003) *Eur Radiol,* 13:195-208; Tanaka et al. (2006) *Ann Surg Oncol,* 13:1671-81; Themelis et al. (2009) *J Biomed Opt,* 4:064012; and Troyan et al. (2009) *Ann Surg Oncol,* 16:2943-52. Briefly, it consists of a spectrally resolved light source (filtered broadband source, light-emitting diode [LED], or laser diode) exciting a fluorophore within a turbid medium. The light emitted from this fluorophore is then imaged onto a charge-coupled device (CCD) camera, with special care taken to filter out the powerful excitation light. Examples of infrared dyes include, but are not limited to, Tracy 652, Tracy 645, rhodamine dyes, cyanine dyes, Cy7, Cy7.5, ALEXA FLUOR®, CYDYE®, TRDYE®, DyLight, and ATTO. Cellular and tissue imaging in the near-infrared (MR) wavelengths between about 650 and about 950 nm is advantageous for in vivo imaging because of the low absorption of biological molecules in this region. Further details regarding the use of labeled antibodies for MR imaging in vivo and detectable labels for MR imaging in vivo are provided in Cillers et al. (2017) *Mol Pharmaceuticals* 14(5): 1623-1633; Hilderbrand et al. (2010) *Curr Opin Chem Biol.* 14(1): 71-79; Hong et al. (2017) *Nat Biomed Eng.* 1, 0010 DOI: 10.1038/s41551-016-0010; Pansare et al. (2012) *Chem Mater.* 24(5): 812-827; Hickson (2009) *Urol Oncol Semin Orig Invest.* 27: 295-297; Zhang et al. (2012) *Curr Protoc Cytom*. Chapter 12: Unit 12.7; Quek et al. (2012) *Nanomaterials.* 2: 92-112; Luker et al. (2008) J Nucl Med 49:1-4; and Liu et al. (2016) *NPG Asia Materials.* 8, e295.

Cerenkov luminescence imaging (CLI) is a molecular optical imaging technique that is based on the detection of optical Cerenkov photons emitted by positron emission tomography (PET) imaging agents (such as those described elsewhere herein). Other CLI imaging agents include, but are not limited to, e.g., $^{131}I$, $^{18}F$, and $^{90}Y$. Cerenkov radiation is produced when a charged particle travels through a dielectric medium (i.e., a medium that can be polarized by an electric field) with a speed faster than the speed of light in that medium. While propagating, the charged particle (a positively charged positron or negatively charged electron) induces a local polarization by displacing the positive and negative charges of the atoms in the medium. See, e.g., FIG. 1 in Grootendorst et al. (2016) *Clin Transl Imaging.* 4(5): 353-366). When the particle's speed exceeds the speed of light, the polarization becomes asymmetrical along the track of the particle, resulting in a dipole electric field at larger distances from the particle. As the particle passes, the electrons of the atoms return to their ground state, thereby emitting the transferred energy as optical photons. CLI images can be acquired by detecting the Cerenkov light from PET tracers using ultra-high-sensitivity optical cameras such as electron-multiplying charge-coupled device (EMCCD) cameras. The CLI image can be analyzed semi-quantitatively in photon radiance. CLI and PET are directly correlated due to both techniques measuring the photons produced by positron-emitting radiopharmaceuticals; PET measures the annihilation photons, and CLI measures the Cerenkov photons. Several studies have shown a strong correlation between CLI and PET for different radiopharmaceuticals in vitro, ex vivo and in vivo, thus demonstrating the feasibility of CLI for molecular imaging of living subjects. Publications regarding CLI or which detail the correlation between CLI and PET include, e.g., Xu et al. (2012) *J Nucl Med,* 53(2):312-317; Liu et al. (2010) *PLoS ONE.* 5(3): e9470; Zhang et al. (2013) *PLoS ONE.* 8(4): e62007; Hu et al. (2015) *Eur Radiol.* 25(6):1814-1822; Robertson et al. (2011) J Nucl Med. 52(11):1764-1769; Timmermand et al. (2015) *J Nucl Med.* 56(3):444-449; Cao et al. (2014) *Biomed Opt Express.* 5(10):3660-3670 and Thorek et al. (2014) *J Nucl Med.* 55(1):95-98.

Methods for Predicting the Responsiveness of a Subject having Cancer to Immunotherapy Also provided are methods of predicting the responsiveness of a subject having cancer to treatment with an immunotherapeutic agent. In some embodiments, the method comprises administering a labeled CD8 binding agent and detecting the binding of the labeled CD8 binding agent to $CD8^+$ T cells in a tumor tissue in the subject, wherein the detection of the binding indicates that the subject is likely to respond to the immunotherapeutic agent. In some embodiments, the method comprises administering a labeled CD8 binding agent described herein and detecting the binding of the labeled CD8 binding agent to $CD8^+$ T cells in a tumor tissue in the subject, wherein the detection of the binding indicates that the subject is in need of treatment with the immunotherapeutic agent. In some embodiments, the CD8 binding agent is labeled with a detectable label (e.g., $^{89}Zr$, $^{124}I$, $^{18}F$, $^{68}Ga$ etc.), and the binding of the labeled CD8 binding agent to $CD8^+$ T cells in a tumor tissue is detected via PET or PET/CT. In some embodiments, the CD8 binding agent is an anti-CD8 VHH conjugated to an $^{18}F$ label. In some embodiments, the CD8 binding agent is an anti-CD8 VHH conjugated to an [$^{18}F$]-aluminum fluoride complex via a compound of Formula (I). In some embodiments, the anti-CD8 VHH comprises a CDR1 comprising the amino acid sequence of SEQ ID NO: 7, a CDR2 comprising the amino acid sequence of SEQ ID NO: 9, and a CDR3 comprising the amino acid sequence of SEQ ID NO: 11. In some embodiments, the anti-CD8 VHH comprises a CDR1 comprising the amino acid sequence of SEQ ID NO: 6, a CDR2 comprising the amino acid sequence of SEQ ID NO: 9, and a CDR3 comprising the amino acid sequence of SEQ ID NO: 12. In some embodiments, the anti-CD8 VHH comprises the amino acid sequence of SEQ ID NO: 3. In some embodiments, the anti-CD8 VHH comprises the amino acid sequence of SEQ ID NO: 4.

In some embodiments, the method comprises administering a therapeutically effective amount of an immunotherapeutic agent, a cell therapy, or a cancer vaccine (e.g., a Personalized Cancer Vaccine or "PCV") to the subject in whom the binding of the labeled CD8 binding agent to $CD8^+$ T cells in a tumor tissue has been detected.

In some embodiments, the CD8 binding agent is administered for more than one time for repeated predication of responsiveness of the subject to the immunotherapeutic agent. In some embodiments, the method is repeated over an extended period of time, such as at least about 6 months, 1 year, 2 years, 3 years, 4 years, 5 years, 10 years or more, including any value or range in between these values.

In some embodiments, the immunotherapeutic agent is an immune checkpoint inhibitor. In some embodiments, the immune checkpoint inhibitor is a therapeutic anti-CTLA-4 antibody, such as ipilimumab (YERVOY®). In some embodiments, the immune checkpoint inhibitor is a therapeutic anti-PD-1 antibody. In some embodiments, the therapeutic anti-PD-1 antibody is nivolumab (OPDIVO®). In some embodiments, the therapeutic anti-PD-1 antibody is pembrolizumab (KEYTRUDA®). In some embodiments, the therapeutic anti-PD-1 antibody is pidilizumab.

In some embodiments, the immune checkpoint inhibitor is a therapeutic anti-PD-L1 antibody. In some embodiments, the therapeutic anti-PD-L1 antibody is BMS-936559. In some embodiments, the therapeutic anti-PD-L1 antibody is avelumab (BANVENCIO®). In some embodiments, the therapeutic anti-PD-L1 antibody is durvalumab (IMFINZI®). In some embodiments, the therapeutic anti-PD-L1 antibody is atezolizumab (TECENTRIQ®).

Further details regarding therapeutic immune checkpoint inhibitors are provided in, e.g., Byun et al. (2017) *Nat Rev Endocrinol.* 13: 195-207; La-Beck et al. (2015) *Pharmacotherapy.* 35(10): 963-976; Buchbinder et al. (2016) *Am J*

*Clin Oncol.* 39(1): 98-106; Michot et al. (2016) *Eur J Cancer.* 54: 139-148, and Topalian et al. (2016) *Nat Rev Cancer.* 16: 275-287.

In some embodiments, the immune checkpoint inhibitor is administered to the subject in combination with one or more additional therapeutic (such as chemotherapeutic) agents. In some embodiments, the immune checkpoint inhibitor that is administered to the subject in combination with one or more additional therapeutic (such as chemotherapeutic) agents is an anti-PD-L1 antibody (such as atezolizumab). Examples of chemotherapeutic agents include erlotinib (TARCEVA®, Genentech/OSI Pharm), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994, 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE (docetaxel, doxetaxel; Sanofi-Aventis); chlorambucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifene citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretinoic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTO IECAN®; ABARE- LIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the present application include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motavizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucotuzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1\lambda$ antibody genetically modified to recognize interleukin-12 p40 protein.

Chemotherapeutic agent also includes “EGFR inhibitors,” which refers to compounds that bind or otherwise interact directly with EGFR and prevent or reduce its signaling activity, and is alternatively referred to as an “EGFR antagonist.” Examples of such agents include antibodies and small molecules that bind EGFR. Examples of antibodies which bind EGFR include MAb 579 (ATCC CRL HB 8506), MAb 455 (ATCC CRL HB8507), MAb 225 (ATCC CRL 8508), MAb 528 (ATCC CRL 8509) (see U.S. Pat. No. 4,943,533, Mendelsohn et al.) and variants thereof, such as chimerized 225 (C225 or Cetuximab; ERBUTIX®) and reshaped human 225 (H225) (see WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., *J. Biol. Chem.* 279(29):30375-30384 (2004)). The anti-EGFR antibody may be conjugated with a cytotoxic agent, thus generating an immunoconjugate (see, e.g., EP659439A2, Merck Patent GmbH). EGFR antagonists include small molecules such as compounds described in U.S. Pat. Nos. 5,616,582; 5,457,105; 5,475,001; 5,654,307; 5,679,683; 6,084,095; 6,265,410; 6,455,534; 6,521,620; 6,596,726; 6,713,484; 5,770,599; 6,140,332; 5,866,572; 6,399,602; 6,344,459; 6,602,863; 6,391,874; 6,344,455; 5,760,041; 6,002,008; and 5,747,498; as well as the following PCT publications: WO 98/14451, WO 98/50038, WO 99/09016, and WO 99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl) amino]-7-[3-(4-morpholinyl)propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl) amino]-1H-pyrrolo[2,3-d]pyrimidin-6-yl]-phenol); (R)-6-(4-hydroxyphenyl)-4-[(1-phenylethyl)amino]-7H-pyrrolo [2,3-d]pyrimidine); CL-387785 (N-[4-[(3-bromophenyl) amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl) methoxy]phenyl]-6[5[[[2methylsulfonyl)ethyl]amino] methyl]-2-furanyl]-4-quinazolinamine).

Chemotherapeutic agents also include “tyrosine kinase inhibitors” including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyridopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lambert); antisense molecules (e.g. those that bind HER-encoding nucleic acid); quinoxalines (U.S. Pat. No. 5,804,396); tyrphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PM 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983

(Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, erlotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMRA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-$OCH_3$, or farnesyl transferase inhibitors (L-739749, L-744832); polyphenols such as quercetin, resveratrol, piceatannol, epigallocatechin gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib.

In some embodiments, the anti-PD-L1 antibody (such as atezolizumab) is administered in combination with one or more of the following chemotherapeutic agents: an anti-HER2 antibody (e.g., trastuzumab (HERCEPTIN®, Genentech) or pertuzumab (PERJETA®, Genentech)), a PD1 binding antagonist (e.g., MDX-1106 (nivolumab), MK-3475 (pembrolizumab, lambrolizumab), CT-011 (pidilizumab), or AMP-224), and a PD-L2 binding antagonist.

In some embodiments, the anti-PD-L1 antibody (such as atezolizumab) is administered in combination with a growth inhibitory agent. A "growth inhibitory agent" when used herein refers to a compound or composition which inhibits growth of a cell either in vitro or in vivo. Exemplary growth inhibitory agents include, e.g., vincas (vincristine and vinblastine), taxanes (Docetaxel (TAXOTERE®, Rhone-Poulenc Rorer) and paclitaxel (TAXOL®, Bristol-Myers Squibb)) and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13.

In some embodiments, the immunotherapeutic agent is a dendritic cell activator or dendritic cell growth factor. In some embodiments, the immunotherapeutic agent is a vaccine adjuvant. In some embodiments, the immunotherapeutic agent is a T-cell stimulator or growth factor. In some embodiments, the immunotherapeutic agent is an agent that neutralizes or inhibits suppressive immune cells, cytokines, and/or enzymes.

In some embodiments, the method comprises administering a immunotherapeutic agent selected from the group consisting of an anti-TIGIT antibody, a TIGIT antagonist, an anti-CSF-1R antibody, an anti-CSF-1R antagonist, an anti-CEA antibody, an anti-CEA antagonist, an anti-CTLA4 antibody, a CTLA4 antagonist, an anti-OX40 antibody, an OX40 agonist, any anti-PDL1 antibody combined with one or more chemotherapeutic agent, any anti-PD1 antibody combined with one or more chemotherapeutic agent, and atezolizumab combined with one or more chemotherapeutic agents. In some embodiments, the anti-PD1 or anti-PDL1 antibody is combined with one or more of TARCEVA® (erlotinib), ZELBORAF® (vemurafenib), GAZYVA® (obinutuzumab), AVASTIN® (bevacizumab), COTELLIC® (cobimetinib), ZELBORAF® (vemurafenib) and COTELLIC® (cobimetinib), ALECENSA® (alectinib), KADCYLA® (ado-trastuzumab emtansine), HERCEPTIN® (trastuzumab), PERJETA® (pertuzumab), polatuzumab, IFN-alpha, an anti-CD40 agent, an anti-OX40 antibody (e.g., an OX40 agonist), an anti-CSF-1R antibody, an anti-CEA antibody, an IDO inhibitor, or an anti-TIGIT antibody. In some embodiments, the anti-PD-L1 antibody is atezolizumab and the atezolizumab is combined with one or more of TARCEVA® (erlotinib), ZELBORAF® (vemurafenib), GAZYVA® (obinutuzumab), AVASTIN® (bevacizumab), COTELLIC® (cobimetinib), ZELBORAF® (vemurafenib) and COTELLIC® (cobimetinib), ALECENSA® (alectinib), KADCYLA® (ado-trastuzumab emtansine), HERCEPTIN® (trastuzumab), PERJETA® (pertuzumab), polatuzumab, IFN-alpha, an anti-CD40 agent, an anti-OX40 antibody (e.g., an OX40 agonist), an anti-CSF-1R antibody, an anti-CEA antibody, an IDO inhibitor, an anti-CTLA4 antibody, or an anti-TIGIT antibody. In some embodiments, the immunotherapeutic agent is a cytokine. In some embodiments, the cytokine is IL2, an engineered IL2, IL15, or an engineered IL15. In some embodiments, the immunotherapeutic agent is a dendritic cell modulator, such as dendritic cell activator or dendritic cell growth factor.

In some embodiments, the cell therapy is chimeric antigen receptor T cell (CAR-T) therapy. In some embodiments, the cell therapy is engineered T-cell receptor T cell (TCR-T) therapy. In some embodiments, the cell therapy is a neoantigen-specific T cell therapy.

Methods of Monitoring Progression in a Subject Having Cancer

Provided herein are methods of monitoring disease progression in a subject having cancer. Such methods comprise administering a labeled CD8 binding agent to the subject and detecting binding of the labeled CD8 binding agent to $CD8^+$ T cells in a tumor tissue in the subject at a first time point and a second time point. In some embodiments, the methods further comprise administering a therapeutically effective amount of an immunotherapeutic agent (e.g., an immunotherapeutic agent described elsewhere herein) to the subject wherein the disease has progressed in the subject. In some embodiments, the methods comprise (a) administering a labeled CD8 binding agent to the subject and detecting binding of the labeled CD8 binding agent to $CD8^+$ T cells in the tumor tissue prior to administering the immunotherapeutic agent, (b) administering the immunotherapeutic agent, (c) administering the labeled CD8 binding agent to the subject and detecting binding of the labeled CD8 binding agent to $CD8^+$ T cells in the tumor tissue at a time point following the administration of the immunotherapeutic agent, and (d) measuring the difference in labeling of $CD8^+$ T cells in the tumor tissue before and after administration of the immunotherapeutic agent.

In some embodiments, the immunotherapeutic agent is an immune checkpoint inhibitor. In some embodiments, the immune checkpoint inhibitor is an anti-PD1 antibody (such as, but no limited to, an anti-PD1 antibody described herein). In some embodiments, the immune checkpoint inhibitor is an anti-PD-L1 antibody (such as, but not limited to, an anti-PD-L1 antibody described herein). In some embodiments, the anti-PD-L1 antibody is atezolizumab. In some embodiments, the anti-PD-L1 antibody (such as atezolizumab) is administered to the subject in combination with a second therapeutic agent (such as, but not limited to, an immunotherapeutic and/or chemotherapeutic agent described elsewhere herein). In some embodiments, the second therapeutic agent is an immunotherapeutic agent. In some embodiments, the immunotherapeutic agent is an anti-PD-L1 antibody or an anti-PD1 antibody which is further combined with one or more of an anti-TIGIT antibody, a TIGIT antagonist, an anti-CSF-1R antibody, an anti-CSF-1R antagonist, an anti-CEA antibody, an anti-CEA antagonist, an anti-OX40 antibody, an OX40 agonist, an anti-CTLA4 antibody, a CTLA4 antagonist, TARCEVA® (erlotinib), ZELBORAF® (vemurafenib), GAZYVA® (obinutuzumab), AVASTIN® (bevacizumab), COTELLIC® (cobimetinib), ZELBORAF® (vemurafenib) and COTELLIC® (cobimetinib), ALECENSA® (alectinib), KADCYLA® (ado-trastuzumab emtansine), HERCEPTIN® (trastuzumab), PERJETA® (pertuzumab), polatuzumab, IFN-alpha, an anti-CD40 agent, or an IDO inhibitor.

In some embodiments, the immunotherapeutic agent is a cytokine. In some embodiments, the cytokine is IL2, an engineered IL2, IL15, or an engineered IL15.

In some embodiments, the immunotherapeutic agent is a dendritic cell modulator. In some embodiments, the immunotherapeutic agent is a dendritic cell activator or dendritic cell growth factor.

In some embodiments, the effect of the immunotherapeutic agent is determined by detecting the level of $CD8^+$ T cells in the tumor tissue at the second time point and comparing it to the level of $CD8^+$ T cells in the tumor tissue at the first time point. In some embodiments, disease progression is detected when the level of $CD8^+$ T cells in the tumor tissue at the second time point is higher than the level of $CD8^+$ T cells in the tumor tissue at the first time point. In some embodiments, the level of $CD8^+$ T cells in the tumor tissue is detected in third, fourth, or fifth subsequent time points. In some embodiments, the time points are at least 1 day, 3 days, 1 week, two weeks, three weeks, four weeks, one month, two months, three months, four months, five months, 6 months, 9 months, 12 months, 1.5 years, 2 years, 2.5 years, 3 years or more than three years apart. In some embodiments, the level of $CD8^+$ T cells in the tumor tissue is detected following the administration of the immunotherapeutic agent to the patient.

In some embodiments, the effect of one or more dosing regimens of an immunotherapeutic agent on tumor tissue is determined by comparing the levels of CD8+ T cells in the tumor tissues of a patient as measured by the CD8 binding agent at a first time point and at a second time point. In some embodiments, the levels (or localization) of CD8+ T cells to tumor tissues after administration of the immunotherapeutic agent to a subject is determined by comparing the levels of CD8+ T cells in the tumor tissues measured by the CD8 binding agent at a first time point before administration of the immunotherapeutic agent and at a second time point after administration.

In some embodiments, the CD8 binding agent is labeled with a detectable label (e.g., $^{89}Zr$, $^{124}I$, $^{18}F$, $^{68}Ga$ etc.), and the binding of the labeled CD8 binding agent to $CD8^+$ T cells in a tumor tissue is detected via PET or PET/CT. In some embodiments, the CD8 binding agent is an anti-CD8 VHH conjugated to an $^{18}F$ label. In some embodiments, the CD8 binding agent is an anti-CD8 VHH conjugated to an [$^{18}F$]-aluminum fluoride complex via a compound of Formula (I). In some embodiments, the anti-CD8 VHH comprises a CDR1 comprising the amino acid sequence of SEQ ID NO: 7, a CDR2 comprising the amino acid sequence of SEQ ID NO: 9, and a CDR3 comprising the amino acid sequence of SEQ ID NO: 11. In some embodiments, the anti-CD8 VHH comprises a CDR1 comprising the amino acid sequence of SEQ ID NO: 6, a CDR2 comprising the amino acid sequence of SEQ ID NO: 9, and a CDR3 comprising the amino acid sequence of SEQ ID NO: 12. In some embodiments, the anti-CD8 VHH comprises the amino acid sequence of SEQ ID NO: 3. In some embodiments, the anti-CD8 VHH comprises the amino acid sequence of SEQ ID NO: 4.

In some embodiments, the CD8 binding agent is administered for more than one time for repeated monitoring of progress of cancer in the subject. In some embodiments, the subject is monitored over an extended period of time, such as at least about 6 months, 1 year, 2 years, 3 years, 4 years, 5 years, 10 years or more, including any value or range in between these values.

Methods of Monitoring Treatment Progress in a Subject having Cancer

Provided herein are methods of monitoring treatment progress in a subject having cancer who has previously received or is currently receiving treatment with an immunotherapeutic agent (e.g., an immunotherapeutic agent described elsewhere herein). Such methods comprise administering a labeled CD8 binding agent to the subject in conjunction with the immunotherapeutic agent, and detecting binding of the labeled CD8 binding agent to $CD8^+$ T cells in the tumor tissue at a first time point and a second time point. In some embodiments, the labeled CD8 binding agent is administered before the immunotherapeutic agent, and the first time point is after the administration of the labeled CD8 binding agent and prior to the administration of the immunotherapeutic agent, and the second time point is after the administration of the immunotherapeutic agent. In some embodiments, lower levels of $CD8^+$ T cells in the tumor tissue at the second time point as compared to the first time point indicates positive treatment progress (e.g., beneficial or desired clinical results). In some embodiments, higher levels of $CD8^+$ T cells in the tumor tissue at the second time point as compared to the first time point indicates lack of treatment progress (e.g., lack beneficial or desired clinical results). In some embodiments, the immunotherapeutic agent is administered before the labeled CD8 binding agent, the first time point is after the administration of the immunotherapeutic agent and after the administration of the labeled CD8 binding agent, and the second time point is after the first time point. In some embodiments, lower levels of $CD8^+$ T cells in the tumor tissue at the second time point as compared to the first time point indicates positive treatment progress (e.g., beneficial or desired clinical results). In some embodiments, higher levels of $CD8^+$ T cells in the tumor tissue at the second time point as compared to the first time point indicates lack of treatment progress (e.g., lack beneficial or desired clinical results). In some embodiments, the method is used to explain the mechanism of treatment failure, e.g., by loss of tumor $CD8^+$ cells, by exhaustion, and/or by loss of therapeutic potency. In some embodiments, the level of $CD8^+$ T cells in the tumor tissue is detected in third, fourth, or fifth subsequent time points. In some embodiments, the time points are at least about 1 day, 3 days, 1 week, two weeks, three weeks, four weeks, one month, two months, three months, four months, five months, 6 months, 9 months 12 months, 1.5 years, 2, years, 2.5 years, 3 years or more than three years apart.

In some embodiments, the immunotherapeutic agent is an immune checkpoint inhibitor. In some embodiments, the immune checkpoint inhibitor is an anti-PD-L1 antibody (e.g., as described elsewhere herein). In some embodiments, the anti-PD-L1 antibody is atezolizumab. In some embodiments, the anti-PD-L1 antibody (such as atezolizumab) is administered to the subject in combination with a second therapeutic agent (e.g., as described elsewhere herein).

In some embodiments, the CD8 binding agent is labeled with a detectable label (e.g., $^{89}Zr$, $^{124}I$, $^{18}F$, $^{68}Ga$ etc.), and the binding of the labeled CD8 binding agent to $CD8^+$ T cells in a tumor tissue is detected via PET or PET/CT. In some embodiments, the CD8 binding agent is an anti-CD8 VHH conjugated to an $^{18}F$ label. In some embodiments, the CD8 binding agent is an anti-CD8 VHH conjugated to an [$^{18}F$]-aluminum fluoride complex via a compound of Formula (I). In some embodiments, the anti-CD8 VHH comprises a CDR1 comprising the amino acid sequence of SEQ ID NO: 7, a CDR2 comprising the amino acid sequence of SEQ ID NO: 9, and a CDR3 comprising the amino acid sequence of SEQ ID NO: 11. In some embodiments, the anti-CD8 VHH comprises a CDR1 comprising the amino acid sequence of SEQ ID NO: 6, a CDR2 comprising the amino acid sequence of SEQ ID NO: 9, and a CDR3 comprising the amino acid sequence of SEQ ID NO: 12. In some embodiments, the anti-CD8 VHH comprises the amino acid sequence of SEQ ID NO: 3. In some embodiments, the anti-CD8 VHH comprises the amino acid sequence of SEQ ID NO: 4.

In some embodiments, the CD8 binding agent is administered for more than one time for repeated monitoring of treatment progress in the subject. In some embodiments, the subject is monitored over an extended period of time, such as at least about 6 months, 1 year, 2 years, 3 years, 4 years, 5 years, 10 years or more, including any value or range in between these values.

Methods of Predicting the Responsiveness of a Subject having Cancer to Treatment with a Cancer Vaccine and Methods of Monitoring Disease Progression in a Subject having Cancer to Whom a Cancer Vaccine has been Administered Provided herein are methods of predicting the responsiveness of a subject having cancer to treatment with a cancer vaccine. In some embodiments, the cancer vaccine is a Personalized Cancer Vaccine ("PCV"). Exemplary PCV are described in, e.g., Ott et al. (2017) *Nature* 547, 217-221 and Sahin et al. (2017) *Nature* 547, 222-226. In some embodiments, the method comprises administering a labeled CD8 binding agent described herein and detecting the binding of the labeled CD8 binding agent to $CD8^+$ T cells in a tumor tissue in the subject, wherein the detection of the binding indicates that the subject is likely to respond to the cancer vaccine. In some embodiments, the method comprises administering a labeled CD8 binding agent described herein and detecting the binding of the labeled CD8 binding agent to $CD8^+$ T cells in a tumor tissue in the subject, wherein the detection of the binding indicates that the subject is in need of treatment with the cancer vaccine. In some embodiments, the cancer vaccine is administered in combination with one or more immunotherapeutic and/or chemotherapeutic agents described herein.

Also provided herein are methods of monitoring disease progression in a subject having cancer. Such methods comprise administering a CD8 binding agent described herein to the subject and detecting binding of the labeled CD8 binding agent to $CD8^+$ T cells in the tumor tissue in the subject at a first time point and a second time point. In some embodiments, the methods further comprise administering a therapeutically effective amount of a cancer vaccine. In some embodiments, the cancer vaccine is a Personalized Cancer Vaccine ("PCV").

Provided herein are methods of monitoring treatment progress in a subject having cancer who has previously received or is currently receiving treatment with cancer vaccine. In some embodiments, the cancer vaccine is a Personalized Cancer Vaccine ("PCV"). In some embodiments, the methods comprise (a) administering a labeled CD8 binding agent to the subject and detecting binding of the labeled CD8 binding agent to $CD8^+$ T cells in the tumor tissue prior to administering the cancer vaccine (e.g., PCV), (b) administering the cancer vaccine (e.g., PCV), (c) administering the labeled CD8 binding agent to the subject and detecting binding of the labeled CD8 binding agent to $CD8^+$ T cells in the tumor tissue at a time point following the administration of the cancer vaccine (e.g., PCV), and (d) measuring the difference in labeling of $CD8^+$ T cells in the tumor tissue before and after administration of the cancer vaccine (e.g., PCV). In some embodiments, the method is used to explain the mechanism of treatment failure, e.g., by loss of tumor $CD8^+$ cells, by exhaustion, and/or by loss of therapeutic potency.

In some embodiments, the CD8 binding agent is labeled with a detectable label (e.g., $^{89}Zr$, $^{124}I$, $^{18}F$, $^{68}Ga$ etc.), and the binding of the labeled CD8 binding agent to $CD8^+$ T cells in a tumor tissue is detected via PET or PET/CT. In some embodiments, the CD8 binding agent is an anti-CD8 VHH conjugated to an $^{18}F$ label. In some embodiments, the CD8 binding agent is an anti-CD8 VHH conjugated to an [$^{18}F$]-aluminum fluoride complex via a compound of Formula (I). In some embodiments, the anti-CD8 VHH comprises a CDR1 comprising the amino acid sequence of SEQ ID NO: 7, a CDR2 comprising the amino acid sequence of SEQ ID NO: 9, and a CDR3 comprising the amino acid sequence of SEQ ID NO: 11. In some embodiments, the anti-CD8 VHH comprises a CDR1 comprising the amino acid sequence of SEQ ID NO: 6, a CDR2 comprising the amino acid sequence of SEQ ID NO: 9, and a CDR3 comprising the amino acid sequence of SEQ ID NO: 12. In some embodiments, the anti-CD8 VHH comprises the amino acid sequence of SEQ ID NO: 3. In some embodiments, the anti-CD8 VHH comprises the amino acid sequence of SEQ ID NO: 4.

In some embodiments, the CD8 binding agent is administered for more than one time for repeated prediction or monitoring in the subject. In some embodiments, the method is repeated or the subject is monitored over an extended period of time, such as at least about 6 months, 1 year, 2 years, 3 years, 4 years, 5 years, 10 years or more, including any value or range in between these values.

Methods of Predicting the Responsiveness of a Subject having Cancer to Treatment with a Cell Therapy and Methods of Monitoring Disease Progression in a Subject having Cancer to Whom a Cell Therapy has been Administered Provided herein are methods of predicting the responsiveness of a subject having cancer to treatment with a cell therapy. In some embodiments, the cell therapy is CAR-T or neoantigen-specific T cell therapy. Exemplary cell therapies are described in, e.g., June et al. (2018) *Science* 359, 1361-1365 and Guedan et al. (2019) *Annu. Rev. Immunol.* 37:145-171. In some embodiments, the method comprises administering a labeled CD8 binding agent described herein and detecting the binding of the labeled CD8 binding agent to $CD8^+$ T cells in a tumor tissue in the subject, wherein the detection of the binding indicates that the subject is likely to respond to the cell therapy. In some embodiments, the method comprises administering a labeled CD8 binding agent described herein and detecting the binding of the labeled CD8 binding agent to $CD8^+$ T cells in a tumor tissue in the subject, wherein the detection of the binding indicates that the subject is in need of treatment with the cell therapy. In some embodiments, the cell therapy is administered in combination with one or more immunotherapeutic and/or chemotherapeutic agents described herein.

Also provided herein are methods of monitoring disease progression in a subject having cancer. Such methods comprise administering a CD8 binding agent described herein to the subject and detecting binding of the labeled CD8 binding agent to $CD8^+$ T cells in the tumor tissue in the subject at a first time point and a second time point. In some embodiments, the methods further comprise administering a therapeutically effective amount of a cell therapy.

Provided herein are methods of monitoring treatment progress in a subject having cancer who has previously received or is currently receiving treatment with cell therapy. In some embodiments, the cell therapy is CAR-T or neoantigen-specific T cell therapy. In some embodiments, the methods comprise (a) administering a labeled CD8 binding agent to the subject and detecting binding of the labeled CD8 binding agent to $CD8^+$ T cells in the tumor tissue prior to administering the cell therapy, (b) administering the cell therapy, (c) administering the labeled CD8 binding agent to the subject and detecting binding of the labeled CD8 binding agent to $CD8^+$ T cells in the tumor tissue at a time point following the administration of the cell therapy, and (d) measuring the difference in labelling of $CD8^+$ T cells in the tumor tissue before and after administration of the cell therapy. In some embodiments, the method is used to explain the mechanism of treatment failure, e.g., by loss of tumor $CD8^+$ cells, by exhaustion, and/or by loss of therapeutic potency.

In some embodiments, the CD8 binding agent is labeled with a detectable label (e.g., $^{89}Zr$, $^{124}I$, $^{18}F$, $^{68}Ga$ etc.), and the binding of the labeled CD8 binding agent to $CD8^+$ T cells in a tumor tissue is detected via PET or PET/CT. In some embodiments, the CD8 binding agent is an anti-CD8 VHH conjugated to an $^{18}F$ label. In some embodiments, the CD8 binding agent is an anti-CD8 VHH conjugated to an [$^{18}F$]-aluminum fluoride complex via a compound of Formula (I). In some embodiments, the anti-CD8 VHH comprises a CDR1 comprising the amino acid sequence of SEQ ID NO: 7, a CDR2 comprising the amino acid sequence of SEQ ID NO: 9, and a CDR3 comprising the amino acid sequence of SEQ ID NO: 11. In some embodiments, the anti-CD8 VHH comprises a CDR1 comprising the amino acid sequence of SEQ ID NO: 6, a CDR2 comprising the amino acid sequence of SEQ ID NO: 9, and a CDR3 comprising the amino acid sequence of SEQ ID NO: 12. In some embodiments, the anti-CD8 VHH comprises the amino acid sequence of SEQ ID NO: 3. In some embodiments, the anti-CD8 VHH comprises the amino acid sequence of SEQ ID NO: 4.

In some embodiments, the CD8 binding agent is administered for more than one time for repeated prediction or monitoring in the subject. In some embodiments, the method is repeated or the subject is monitored over an extended period of time, such as at least about 6 months, 1 year, 2 years, 3 years, 4 years, 5 years, 10 years or more, including any range in between these values.

Methods for Autoimmune Diseases or Conditions, Transplant Rejection, and Graft-Versus-Host Disease Because of their high sensitivity and low immunogenicity, the CD8 binding agents described herein are suitable for monitoring disease progression, predicting responsiveness to immunotherapy, and/or monitoring treatment progress in a subject having an autoimmune disease or condition, transplant rejection, or graft-versus-host disease. In some embodiments, the immunotherapy is an immunosuppressant agent.

Provided herein are methods of monitoring treatment progress and disease progression in a subject having an autoimmune disease or condition (e.g., autoimmune arthritis, colitis, celiac disease), transplant rejection, or graft-versus-host disease. Such diseases all involve $CD8^+$ T cells as part of the damaging inflammatory process. See Petrelli & Femke, $CD8^+$ *T cells in human autoimmune arthritis: the usual suspects; Nature Reviews Thumatology* 12:421-428 (2016). Such methods comprise administering a labeled CD8 binding agent to the subject, with or without interventional treatment, and detecting binding of the labeled CD8 binding agent to $CD8^+$ T cells in the tissue at a first time point and a second time point. In some embodiments, an increase in $CD8^+$ T cells from the first time point and the second time point is an indication that the autoimmune disease or condition, transplant rejection, or graft-versus-host disease has progressed. In some embodiments, an interventional therapy to treat the autoimmune disease or condition, transplant rejection, or graft-versus-host disease is administered before the labeled CD8 binding agent, the first time point is after the administration of the interventional therapy to treat the autoimmune disease or condition, transplant rejection, or graft-versus-host disease and after the administration of the labeled CD8 binding agent, and the second time point is after the first time point. In some embodiments, lower levels of $CD8^+$ T cells in the tissue at the second time point as compared to the first time point indicates positive treatment progress (e.g., beneficial or desired clinical results). In some embodiments, higher levels of $CD8^+$ T cells in the diseased tissue at the second time point as compared to the first time point indicates lack of treatment progress (e.g., lack beneficial or desired clinical results). In some embodiments, the level of $CD8^+$ T cells in the tissue is detected in third, fourth, or fifth subsequent time points. In some embodiments, lower levels of $CD8^+$ T cells in the tissue at the subsequent time point(s) as compared to the first time point indicates lack of treatment progress (e.g., lack beneficial or desired clinical results). In some embodiments, higher levels of $CD8^+$ T cells in the diseased tissue at the subsequent time point(s) as compared to the first time point indicates lack of treatment progress (e.g., lack beneficial or desired clinical results). In some embodiments, the method is used to explain the mechanism of treatment failure. In some embodiments, the time points are at least about 1 day, 3 days, 1 week, two weeks, three weeks, four weeks, one month, two months, three months, four months, five months, 6 months, 9 months 12 months, 1.5 years, 2, years, 2.5 years, 3 years or more than three years apart.

Also provided herein are methods of predicting responsiveness of a subject having an autoimmune disease or condition, transplant rejection, or graft-versus-host disease to an immunotherapeutic agent (e.g., an immunosuppressant agent). In some embodiments, the method comprises administering a labeled CD8 binding agent described herein and detecting the binding of the labeled CD8 binding agent to $CD8^+$ T cells in a diseased tissue in the subject, wherein the detection of the binding indicates that the subject is likely to respond to the immunotherapeutic agent. In some embodiments, the method comprises administering a labeled CD8 binding agent described herein and detecting the binding of the labeled CD8 binding agent to $CD8^+$ T cells in a diseased tissue in the subject, wherein the detection of the binding indicates that the subject is in need of treatment with the immunotherapeutic agent. In some embodiments, the method further comprises administering a therapeutically effective amount of the immunotherapeutic agent to the subject in whom the binding has been detected.

Further provided are methods of monitoring treatment progress in a subject having an autoimmune disease or condition, transplant rejection, or graft-versus-host disease who has or is receiving an immunotherapeutic agent (e.g., an immunosuppressant agent). In some embodiments, the methods comprise (a) administering a labeled CD8 binding agent to the subject and detecting binding of the labeled CD8 binding agent to $CD8^+$ T cells in a diseased tissue prior to administering the immunotherapeutic agent, (b) administering the immunotherapeutic agent, (c) administering the labeled CD8 binding agent to the subject and detecting binding of the labeled CD8 binding agent to $CD8^+$ T cells in the diseased tissue at a time point following the administration of the immunotherapeutic agent, and (d) measuring the difference in labeling of $CD8^+$ T cells in the tumor tissue before and after administration of the immunotherapeutic agent. In some embodiments, lower levels of $CD8^+$ T cells in the diseased tissue at a time point following the administration of the immunotherapeutic agent as compared to the time point before the administration of the immunotherapeutic agent indicates positive treatment progress (e.g., beneficial or desired clinical results). In some embodiments, higher levels of $CD8^+$ T cells in the diseased tissue at a time point following the administration of the immunotherapeutic agent as compared to the time point before the administration of the immunotherapeutic agent indicates lack of treatment progress (e.g., lack beneficial or desired clinical results). In some embodiments, the level of $CD8^+$ T cells in the tissue is detected in one, two, three, four or more subsequent time points. In some embodiments, the method is used to explain the mechanism of treatment failure. In some embodiments, the time points are at least about 1 day, 3 days, 1 week, two weeks, three weeks, four weeks, one month, two months, three months, four months, five months, 6 months, 9 months 12 months, 1.5 years, 2, years, 2.5 years, 3 years or more than three years apart.

In some embodiments, the CD8 binding agent is labeled with a detectable label (e.g., $^{89}Zr$, $^{124}I$, $^{18}F$, $^{68}Ga$ etc.), and the binding of the labeled CD8 binding agent to $CD8^+$ T cells in a tumor tissue is detected via PET or PET/CT. In some embodiments, the CD8 binding agent is an anti-CD8 VHH conjugated to an $^{18}F$ label. In some embodiments, the CD8 binding agent is an anti-CD8 VHH conjugated to an [$^{18}F$]-aluminum fluoride complex via a compound of Formula (I). In some embodiments, the anti-CD8 VHH comprises a CDR1 comprising the amino acid sequence of SEQ ID NO: 7, a CDR2 comprising the amino acid sequence of SEQ ID NO: 9, and a CDR3 comprising the amino acid sequence of SEQ ID NO: 11. In some embodiments, the anti-CD8 VHH comprises a CDR1 comprising the amino acid sequence of SEQ ID NO: 6, a CDR2 comprising the amino acid sequence of SEQ ID NO: 9, and a CDR3 comprising the amino acid sequence of SEQ ID NO: 12. In some embodiments, the anti-CD8 VHH comprises the amino acid sequence of SEQ ID NO: 3. In some embodiments, the anti-CD8 VHH comprises the amino acid sequence of SEQ ID NO: 4.

In some embodiments, the method is used for transplant rejection, such as kidney, liver, heart, or heart/lung transplant rejection. In some embodiments, the method is used for an autoimmune disease or condition, such as hepatitis, lupus (e.g. SLE), vasculitis, and neuritis with demyelination including multiple sclerosis.

In some embodiments, the immunotherapeutic agent is an immunosuppressant agent. Suitable immunosuppressant agents include, but are not limited to, prednisone, cyclophosphamide, cyclosporine, mycophenolate mofetil, ibrutinib, ruxolitinib, and biologics such as TNF-alpha antibodies, e.g., adalimumab, etanercept, golimumab, and infliximab.

In some embodiments, the CD8 binding agent is administered for more than one time for repeated prediction or monitoring in the subject. In some embodiments, the method is repeated or the subject is monitored over an extended period of time, such as at least about 6 months, 1 year, 2 years, 3 years, 4 years, 5 years, 10 years or more, including any value or range in between these values.

In some embodiments, the CD8 binding agent can enable serial evaluation of lymphoid tissues and organs involved in cancer, an autoimmune disease or condition, transplant rejection, or a graft-versus-host disease. In some embodiments, the level(s) or signal(s) detected from the CD8 binding agent in a subject can be correlated with other imaging technologies (e.g., MRI). In some embodiments, the level(s) or signal(s) detected from the CD8 binding agent in a subject can be correlated with blood and/or tissue biomarkers (e.g., tissue biopsy biomarkers).

In some embodiments, the CD8 binding agent enables multiplexed imaging, e.g., with another imaging scan such as PET, SPECT or scintigraphic scan.

In some embodiments, the imaging data obtained using the CD8 binding agent is correlated with data from other radiologic methods, such as MRI, CT, ultrasound, or x-ray.

Pharmaceutical Compositions

Also provided are compositions, including pharmaceutical formulations, comprising a CD8 binding agent such as anti-CD8 antibody (e.g., anti-CD8 VHH), or polynucleotides comprising sequences encoding a CD8 binding agent such as anti-CD8 antibody (e.g., anti-CD8 VHH). In some embodiments, compositions comprise one or more CD8 binding agents that bind CD8, or one or more polynucleotides comprising sequences encoding one or more CD8 binding agents that bind CD8. These compositions may further comprise suitable carriers, such as pharmaceutically acceptable excipients including buffers, which are well known in the art.

In some embodiments, there is provided a pharmaceutical composition comprising any one of the CD8 binding agents (e.g., labeled CD8 binding agents) described herein, and a pharmaceutically acceptable carrier. In some embodiments, there is provided a pharmaceutically formulation comprising any one of the labeled CD8 binding agents described herein and one or more anti-oxidant compounds, such as methionine and/or N-acetyl tryptophan. In some embodiments, the pharmaceutical formulation comprises histidine, methionine, N-acetyl tryptophan, and/or sucrose. In some embodiments, the pharmaceutical formulation comprises histidine, methionine, N-acetyl tryptophan, and sucrose.

Pharmaceutical formulations of a CD8 binding agent as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid, N-acetyltryptophan and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary (e.g., an immunotherapeutic agent) for the particular indication being treated (e.g., cancer, autoimmune disease or condition, transplant rejection, or graft-versus-host disease), preferably those with complementary activities that do not adversely affect each other. For example, it may be desirable to further provide statin. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

Articles of Manufacture and Kits

In some embodiments, provided is an article of manufacture or kit containing materials useful for predicting the responsiveness of a subject having a disease (e.g., cancer, autoimmune disease or condition, transplant rejection, or graft-versus-host disease) to an immunotherapeutic agent, for monitoring disease progression in a subject having a disease (e.g., cancer, autoimmune disease or condition, transplant rejection, or graft-versus-host disease), and/or monitoring treatment progress in a subject having a disease (e.g., cancer, autoimmune disease or condition, transplant rejection, or graft-versus-host disease).

In some embodiments, the article of manufacture or kit comprises a container containing one or more of the CD8 binding agents or the compositions described herein. In some embodiments, the article of manufacture or kit comprises a container containing nucleic acids(s) encoding one (or more) of the CD8 binding agents or the compositions described herein. In some embodiments, the kit includes a cell of a cell line that produces a CD8 binding agent (e.g., an anti-CD8 antibody) as described herein.

In some embodiments, the kit or article of manufacture comprises an anti-CD8 WM. In some embodiments, the kit or article of manufacture comprises a labeled CD8 binding agent, e.g., an immunoconjugate comprising a detectable label. In some embodiments, the kit comprises both an anti-CD8 antibody (e.g., anti-CD8 VHH) and a labeled CD8 binding agent. In some embodiments, the kit or article of manufacture further comprises reagents for preparing the labeled CD8 binding agent, such as a chelating agent of Formula (I) and an [$^{18}$F]-aluminum fluoride complex.

In some embodiments, the labeled CD8 binding agent is an anti-CD8 VHH conjugated to an $^{18}$F label. In some embodiments, the CD8 binding agent is an anti-CD8 VHH conjugated to an [$^{18}$F]-aluminum fluoride complex via a compound of Formula (I). In some embodiments, the anti-CD8 VHH comprises a CDR1 comprising the amino acid sequence of SEQ ID NO: 7, a CDR2 comprising the amino acid sequence of SEQ ID NO: 9, and a CDR3 comprising the amino acid sequence of SEQ ID NO: 11. In some embodiments, the anti-CD8 VHH comprises a CDR1 comprising the amino acid sequence of SEQ ID NO: 6, a CDR2 comprising the amino acid sequence of SEQ ID NO: 9, and a CDR3 comprising the amino acid sequence of SEQ ID NO: 12. In some embodiments, the anti-CD8 VHH comprises the amino acid sequence of SEQ ID NO: 3. In some embodiments, the anti-CD8 VHH comprises the amino acid sequence of SEQ ID NO: 4.

In some embodiments, the kit includes one or more positive controls, for example CD8 (or fragments thereof) or CD8$^+$ cells. In some embodiments, the kit includes negative controls, for example a surface or solution that is substantially free of CD8.

In some embodiments, the article of manufacture or kit comprises a container and a label or package insert on or associated with the container. Suitable containers include, for example, bottles, vials, syringes, IV solution bags, etc. The containers may be formed from a variety of materials such as glass or plastic. The container holds a composition, which is by itself or combined with another composition effective for treating, preventing and/or diagnosing cancer and may have a sterile access port (for example, the container may be an intravenous solution bag or a vial having a stopper pierceable by a hypodermic injection needle). At least one agent in the composition is a CD8 binding agent described herein. The label or package insert indicates that the composition is used for predicting the responsiveness of a subject having cancer to an immunotherapeutic agent, for monitoring disease progression in a subject having cancer, and/or monitoring treatment progress in a subject having cancer.

Moreover, the article of manufacture or kit may comprise (a) a first container with a composition contained therein, wherein the composition comprises a CD8 binding agent described herein; and (b) a second container with a composition contained therein, wherein the composition comprises a further cytotoxic or otherwise therapeutic agent. In some embodiments, the therapeutic agent is an immunotherapeutic agent, as described herein.

The article of manufacture or kit provided herein may further comprise a package insert indicating that the composition(s) can be used to predict the responsiveness of a subject having a disease (e.g., cancer, autoimmune disease or condition, transplant rejection, or graft-versus-host disease) to an immunotherapeutic agent, to monitor disease progression in a subject having a disease (e.g., cancer, autoimmune disease or condition, transplant rejection, or graft-versus-host disease), and/or monitor treatment progress in a subject having a disease (e.g., cancer, autoimmune disease or condition, transplant rejection, or graft-versus-host disease). Additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXEMPLARY EMBODIMENTS

The Present Application Provides the Following Embodiments:

1. A CD8 binding agent comprising a variable domain of the heavy chain of a heavy chain antibody (VHH domain), wherein the CD8 binding agent specifically binds a human CD8 with a $K_D$ of about 1 nM or less.
2. The CD8 binding agent of embodiment 1, wherein the CD8 binding agent binds human CD8 with a $k_{off}$ of about 0.002/s or less.
3. The CD8 binding agent of embodiment 1 or 2, wherein the $K_D$ and/or $k_{off}$ is determined by surface plasmon resonance using a one-armed human CD8α/human CD8β-Fc fusion protein (e.g., a single-chain polypeptide comprising human CD8α and human CD8β, which is fused to one polypeptide chain of an Fc) as a reagent.
4. The CD8 binding agent of any one of embodiments 1-3, wherein the CD8 binding agent binds cynomolgus CD8 with a $K_D$ of about 1 nM or less.
5. The CD8 binding agent of any one of embodiments 1-4, wherein the CD8 binding agent binds cynomolgus CD8 with a $k_{off}$ of about 0.004/s or less.
6. The CD8 binding agent of embodiment 4 or 5, wherein the $K_D$ and/or $k_{off}$ is determined by surface plasmon resonance using a one-armed cynomolgus CD8α/cynomolgus CD8β-Fc fusion protein (e.g., a single-chain polypeptide comprising cynomolgus CD8α and cynomolgus CD8β, which is fused to one polypeptide chain of an Fc) as a reagent.
7. The CD8 binding agent of any one of embodiments 1-6, wherein the CD8 binding agent does not stimulate or inhibit the activation of CD8$^+$ T cells.

8. The CD8 binding agent of any one of embodiments 1-7, wherein the CD8 binding agent does not induce $CD8^+$ T cell proliferation.
9. The CD8 binding agent of any one of embodiments 1-8, wherein the CD8 binding agent does not bind $CD4^+$ T cells.
10. The CD8 binding agent of any one of embodiments 1-9, wherein the VHH domain is a llama VHH.
11. The CD8 binding agent of any one of embodiments 1-10, wherein the VHH domain is humanized.
12. The CD8 binding agent of any one of embodiments 1-11, wherein the VHH domain specifically binds a human CD8α epitope comprising Arg25, Lys42, Gln44, Val45, Leu46, Leu47, Ser48, Pro50, Thr51, Ser52, Gln75, Arg93, Leu94, Gly95, Asp96, and Thr97, wherein the amino acid numbering is according to SEQ ID NO: 13.
13. The CD8 binding agent of embodiment 12, wherein the VHH domain comprises a complementarity determining region (CDR) 1 comprising an amino acid sequence of SEQ ID NO: 6 or 7; a CDR2 comprising an amino acid sequence of SEQ ID NO: 8 or 9; and a CDR3 comprising an amino acid sequence of any one of SEQ ID NOs: 10-12.
14. The CD8 binding agent of embodiment 13, wherein the VHH domain comprises:
    (1) a CDR1 comprising the amino acid sequence of SEQ ID NO: 6, a CDR2 comprising the amino acid sequence of SEQ ID NO: 8, and a CDR3 comprising the amino acid sequence of SEQ ID NO: 10;
    (2) a CDR1 comprising the amino acid sequence of SEQ ID NO: 6, a CDR2 comprising the amino acid sequence of SEQ ID NO: 9, and a CDR3 comprising the amino acid sequence of SEQ ID NO: 11;
    (3) a CDR1 comprising the amino acid sequence of SEQ ID NO: 7, a CDR2 comprising the amino acid sequence of SEQ ID NO: 9, and a CDR3 comprising the amino acid sequence of SEQ ID NO: 11; or
    (4) a CDR1 comprising the amino acid sequence of SEQ ID NO: 6, a CDR2 comprising the amino acid sequence of SEQ ID NO: 9, and a CDR3 comprising the amino acid sequence of SEQ ID NO: 12.
15. The CD8 binding agent of embodiment 13, wherein the VHH domain comprises a CDR1 comprising the amino acid sequence of SEQ ID NO: 6, a CDR2 comprising the amino acid sequence of SEQ ID NO: 9, and a CDR3 comprising the amino acid sequence of SEQ ID NO: 12.
16. The CD8 binding agent of any one of embodiments 1-15, wherein the VHH domain comprises L49A, wherein the numbering is according to Kabat numbering.
17. The CD8 binding agent of any one of embodiments 1-16, wherein the VHH domain comprises one or more amino acid modifications selected from the group consisting of V89T substitution, T110Q substitution, S112Q substitution and A114 addition, wherein the numbering is according to Kabat numbering.
18. The CD8 binding agent of any one of embodiments 1-17, wherein the VHH domain comprises the amino acid sequence of any one of SEQ ID NOs: 1-4.
19. The CD8 binding agent of any one of embodiments 1-18, wherein the agent does not comprise an Fc region.
20. An isolated nucleic acid encoding the CD8 binding agent of any one embodiments 1-19.

21. An expression vector comprising the nucleic acid of embodiment 20.
22. A host cell comprising the nucleic acid of embodiment 20 or the expression vector of embodiment 21.
23. The host cell of embodiment 22, wherein the host cell is a eukaryotic cell.
24. The host cell of embodiment 23, wherein the host cell is a mammalian cell.
25. The host cell of embodiment 24, wherein the host cell is an Expi293 cell.
26. The host cell of embodiment 22, wherein the host cell is a prokaryotic cell.
27. A method of making a CD8 binding agent, the method comprising:
    a) culturing the host cell of any one of embodiments 22-26 under conditions where the agent is produced; and
    b) recovering the CD8 binding agent produced by the host cell.
28. The CD8 binding agent of any one of embodiments 1-19, wherein the VHH domain is conjugated to a label.
29. The CD8 binding agent of embodiment 28, wherein the label is a fluorescent dye, a radionuclide, or an enzyme.
30. The CD8 binding agent of embodiment 29, wherein the label is a radionuclide.
31. The CD8 binding agent of embodiment 30, wherein the radionuclide is $^{18}F$, $^{89}Zr$, $^{99m}Tc$, $^{67}Ga$, $^{68}Ga$, $^{64}Cu$, $^{52}Mn$, $^{111}In$, or $^{124}I$.
32. The CD8 binding agent of any one of embodiments 28-31, wherein the VHH domain is conjugated to a label via a chelating moiety.
33. The CD8 binding agent of embodiment 32, wherein the chelating moiety is covalently linked to the VHH domain via a lysine residue.
34. The CD8 binding agent of embodiment 32 or 33, wherein the label forms a complex with a metal, wherein the complex is chelated by the chelating moiety.
35. The CD8 binding agent of embodiment 34, wherein the label is $^{18}F$ and the metal is aluminum.
36. The CD8 binding agent of embodiment 35, wherein the chelating moiety is a compound of Formula (I):

(I)

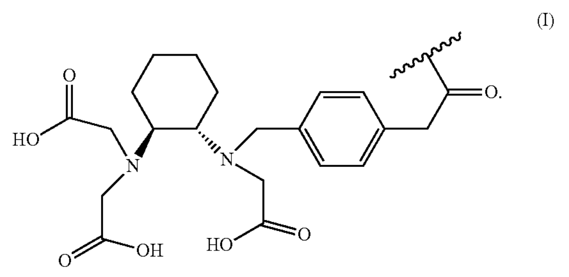 [SMILES: *C(=O)Cc1ccc(CN(CC(=O)O)[C@H]2CCCC[C@@H]2N(CC(=O)O)CC(=O)O)cc1]

37. A method of detecting $CD8^+$ cells in a subject, the method comprising:
    a) administering the labeled CD8 binding agent of any one of embodiments 28-36 to the subject; and
    b) detecting binding of the labeled CD8 binding agent to $CD8^+$ cells in the subject, wherein the detection of the binding indicates the presence of $CD8^+$ cells.
38. The method of embodiment 37, wherein detecting binding of the labeled CD8 binding agent to $CD8^+$ cells in the subject comprises imaging $CD8^+$ cells in the subject.

39. The method of embodiment 38, wherein imaging $CD8^+$ cells in the subject comprises performing a positron emission tomography (PET) scan or positron emission tomography/computed tomography (PET/CT) scan on the subject.
40. The method of any one of embodiments 37-39, wherein the $CD8^+$ cells are $CD8^+$ T cells.
41. The method of any one of embodiments 37-40, wherein the $CD8^+$ cells are $CD8^+$ tumor cells.
42. The method of any one of embodiments 37-41, wherein the detecting is carried out within about 1 day or less after the administering.
43. The method of any one of embodiments 37-42, wherein the method is repeated for one or more times.
44. The method of embodiment 43, wherein the method is repeated after about 1 day after the prior administration of the CD8 binding agent.
45. The method of embodiment 43 or 44, wherein the method is repeated for 1 to 4 times per year.
46. The method of any one of embodiments 43-45, wherein the method is repeated for more than 1 year.
47. The method of any one of embodiments 37-46, wherein the method has a sensitivity of about 1 nM to about 30 nM.
48. The method of any one of embodiments 37-47, wherein the subject is a human or a non-human primate.
49. The method of embodiment 48, wherein the non-human primate is a cynomolgus monkey or a rhesus monkey.
50. The method of embodiment 48, wherein the subject is human.
51. The method of any one of embodiments 37-50, wherein the subject has cancer.
52. The method of any one of embodiments 37-50, wherein the subject has an autoimmune disease, transplant rejection, or graft-versus-host disease.
53. A method of predicting responsiveness of a subject having a cancer to an immunotherapeutic agent, a cell therapy, or a cancer vaccine, the method comprising:
   a) administering the labeled CD8 binding agent of any one of embodiments 28-36 to the subject and;
   b) detecting binding of the labeled CD8 binding agent to $CD8^+$ T cells in a tumor tissue in the subject, wherein the detection of the binding indicates that the subject is likely to respond to the immunotherapeutic agent, the cell therapy, or the cancer vaccine.
54. The method of embodiment 53, further comprising the step of:
   (c) administering a therapeutically effective amount of the immunotherapeutic agent, the cell therapy, or the cancer vaccine to the subject in whom the binding has been detected.
55. A method of monitoring disease progression in a subject having cancer, the method comprising:
   a) administering the labeled CD8 binding agent of any one of embodiments 28-36 to the subject, and
   b) detecting binding of the labeled CD8 binding agent to $CD8^+$ T cells in a tumor tissue in the subject at a first time point and a second time point.
56. The method of embodiment 55, further comprising the step of:
   (c) administering a therapeutically effective amount of an immunotherapeutic agent, a cell therapy, or a cancer vaccine to the subject wherein a level of $CD8^+$ T cells in the tumor tissue at the second time point is higher than the level of $CD8^+$ T cells in the tumor tissue at the first time point.
57. A method of monitoring treatment progress in a subject having cancer who has or is receiving an immunotherapeutic agent, a cell therapy, or a cancer vaccine, the method comprising:
   i) administering the labeled CD8 binding agent of any one of embodiments 28-36 to the subject in conjunction with the immunotherapeutic agent, the cell therapy, or the cancer vaccine, and
   ii) detecting binding of the labeled CD8 binding agent to $CD8^+$ T cells in a tumor tissue at a first time point and a second time point.
58. The method of embodiment 57, wherein the labeled CD8 binding agent is administered before the immunotherapeutic agent, the cell therapy, or the cancer vaccine, wherein the first time point is after the administration of the labeled CD8 binding agent and prior to the administration of the immunotherapeutic agent, the cell therapy, or the cancer vaccine, and wherein the second time point is after the administration of the immunotherapeutic agent, the cell therapy, or the cancer vaccine.
59. The method of embodiment 57, wherein the immunotherapeutic agent, the cell therapy, or the cancer vaccine is administered before the labeled CD8 binding agent, wherein the first time point is after the administration of the immunotherapeutic agent, the cell therapy, or the cancer vaccine and after the administration of the labeled CD8 binding agent, and wherein the second time point is after the first time point.
60. The method of any one of embodiments 53-54, and 56-59, wherein the immunotherapeutic agent is administered to the subject.
61. The method of embodiment 60, wherein the immunotherapeutic agent is an anti-PDL1 antibody, an anti-PD1 antibody, an anti-TIGIT antibody, a TIGIT antagonist, an anti-CSF-1R antibody, an anti-CSF-1R antagonist, an anti-CEA antibody, an anti-CEA antagonist, an anti-CTLA4 antibody, a CTLA4 antagonist, an anti-OX40 antibody, or an OX40 agonist.
62. The method of embodiment 61, wherein the immunotherapeutic agent is an anti-PD-L1 antibody.
63. The method of embodiment 62, wherein the anti-PD-L1 antibody is atezolizumab.
64. The method of embodiment 62 or 63, wherein the anti-PD-L1 antibody is administered in combination with one or more therapeutic agents.
65. The method of embodiment 64, wherein the one or more therapeutic agents is TARCEVA® (erlotinib), ZELBORAF® (vemurafenib), GAZYVA® (obinutuzumab), AVASTIN® (bevacizumab), COTELLIC® (cobimetinib), ZELBORAF® (vemurafenib) and COTELLIC® (cobimetinib), ALECENSA® (alectinib), KADCYLA® (ado-trastuzumab emtansine), HERCEPTIN® (trastuzumab), PERJETA® (pertuzumab), polatuzumab, IFN-alpha, an anti-CD40 agent, an anti-OX40 antibody, an OX40 agonist, an anti-CSF-1R antibody, an anti-CEA antibody, an IDO inhibitor, or an anti-TIGIT antibody.
66. The method of embodiment 60, wherein the immunotherapeutic agent is a cytokine.
67. The method of embodiment 66, wherein the cytokine is IL2, an engineered IL2, IL15, or an engineered IL15.
68. The method of embodiment 60, wherein the immunotherapeutic agent is a bispecific antigen-binding molecule that specifically binds CD3.

69. The method of embodiment 60, wherein the immunotherapeutic agent is a bispecific antigen-binding molecule that specifically binds CD16.
70. The method of embodiment 68 or 69, wherein the bispecific antigen-binding molecule is an antibody or antigen-binding fragment thereof.
71. The method of embodiment 69 or 70, wherein the bispecific antigen-binding molecule specifically binds CD16A.
72. The method of embodiment 60, wherein the immunotherapeutic agent is a dendritic cell modulator.
73. The method of embodiment 72, wherein the immunotherapeutic agent is a dendritic cell activator or dendritic cell growth factor.
74. The method of any one of embodiments 53-54, and 56-59, wherein the cancer vaccine is administered to the subject.
75. The method of embodiment 74, wherein the cancer vaccine is a Personalized Cancer Vaccine (PCV).
76. The method of any one of embodiments 53-54, and 56-59, wherein the cell therapy is administered to the subject.
77. The method of embodiment 76, wherein the cell therapy is a CAR-T or neoantigen-specific T cells.
78. A method of predicting responsiveness of a subject having an autoimmune disease, transplant rejection, or graft-versus-host disease to an immunotherapeutic agent, the method comprising:
   a) administering the labeled CD8 binding agent of any one of embodiments 28-36 to the subject and;
   b) detecting binding of the labeled CD8 binding agent to $CD8^+$ T cells in a diseased tissue in the subject, wherein the detection of the binding indicates that the subject is likely to respond to the immunotherapeutic agent.
79. The method of embodiment 78, further comprising the step of:
   (c) administering a therapeutically effective amount of the immunotherapeutic agent to the subject in whom the binding has been detected.
80. A method of monitoring disease progression in a subject having an autoimmune disease, transplant rejection, or graft-versus-host disease, the method comprising:
   a) administering the labeled CD8 binding agent of any one of embodiments 28-36 to the subject, and
   b) detecting binding of the labeled CD8 binding agent to $CD8^+$ T cells in a diseased tissue in the subject at a first time point and a second time point, wherein an increase in $CD8^+$ T cells from the first time point and the second time point is an indication that the autoimmune disease, transplant rejection, or graft-versus-host disease has progressed.
81. The method of embodiment 80, further comprising the step of:
   (c) administering a therapeutically effective amount of an immunotherapeutic agent to the subject wherein a level of $CD8^+$ T cells in the diseased tissue at the second time point is lower than the level of $CD8^+$ T cells in the diseased tissue at the first time point.
82. A method of monitoring treatment progress in a subject having an autoimmune disease, transplant rejection, or graft-versus-host disease who has or is receiving an immunotherapeutic agent, the method comprising:
   i) administering the labeled CD8 binding agent of any one of embodiments 28-36 to the subject in conjunction with the immunotherapeutic agent, and
   ii) detecting binding of the labeled CD8 binding agent to $CD8^+$ T cells in a diseased tissue at a first time point and a second time point.
83. The method of embodiment 82, wherein the labeled CD8 binding agent is administered before the immunotherapeutic agent, wherein the first time point is after the administration of the labeled CD8 binding agent and prior to the administration of the immunotherapeutic agent, and wherein the second time point is after the administration of the immunotherapeutic agent.
84. The method of embodiment 82, wherein the immunotherapeutic agent is administered before the labeled CD8 binding agent, wherein the first time point is after the administration of the immunotherapeutic agent and after the administration of the labeled CD8 binding agent, and wherein the second time point is after the first time point.
85. The method of any one of embodiments 53-84, wherein detecting binding of the labeled CD8 binding agent to the $CD8^+$ T cells in the subject comprises imaging $CD8^+$ T cells in the subject.
86. The method of embodiment 85, wherein imaging the $CD8^+$ T cells in the subject comprises performing a positron emission tomography (PET) scan or positron emission tomography/computed tomography (PET/CT) scan on the subject.
87. The method of any one of embodiments 53-86, further comprising performing another imaging scan (e.g., PET, SPECT, or scintigraphic scan) within about 48 hours from the imaging using the labeled CD8 binding agent.
88. The method of any one of embodiments 55-77 and 80-87, wherein the subject is monitored for at least 1 year.
89. A method of identifying gut microbial strains associated with responsiveness to treatment with an immunotherapeutic agent, comprising:
   a) obtaining gut microbiome samples from a population of subjects having cancer, which population comprises subjects who are responsive to treatment with the immunotherapeutic agent and subjects who are not responsive to treatment with the immunotherapeutic agent;
   b) analyzing the gut microbiome samples of the subjects who are responsive to the treatment and the gut microbiome samples of the subjects who are not responsive to the treatment; and
   c) identifying gut microbial strains associated with the subjects who are responsive to the treatment; wherein responsiveness is determined by detecting binding of the labeled CD8 binding agent of any one of embodiments 28-36 to $CD8^+$ T cells in a tumor tissue in the subjects, and wherein the detection of the binding indicates that the subjects are responsive to the immunotherapeutic agent.
90. The method of embodiment 89, further comprising preparing a microbiome-based drug comprising gut microbial strains associated with responsiveness to the immunotherapeutic agent.
91. The method of embodiment 89 or 90, wherein the immunotherapeutic agent is an anti-PD-1 antibody.
92. The method of embodiment 89 or 90, wherein the immunotherapeutic agent is an anti-PD-L1 antibody.

93. The method of embodiment 92, wherein the anti-PD-L1 antibody is atezolizumab.
94. A kit comprising the labeled CD8 binding agent of any one of embodiments 28-36.
95. A method of preparing a labeled CD8 binding agent, comprising conjugating a chelating moiety to the VHH domain of the CD8 binding agent of any one of embodiments 1-19 to provide a conjugate, and contacting the conjugate with an aluminum fluoride complex comprising $^{18}F$ to provide the labeled CD8 binding agent, wherein the chelating moiety is a compound of Formula (I):

(I)

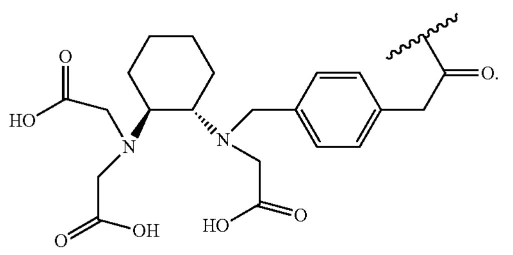

96. The method of embodiment 95, wherein the conjugate is contacted with the aluminum fluoride complex in the presence of one or more anti-oxidant compounds.
97. The method of embodiment 96, wherein the one or more anti-oxidant compounds comprise methionine and/or N-acetyl-tryptophan.
98. A pharmaceutical formulation comprising the CD8 binding agent of any one of embodiments 1-19 and 28-36, and one or more anti-oxidant compounds.
99. The pharmaceutical formulation of embodiment 98, wherein the one or more anti-oxidant compounds are methionine and/or N-acetyl tryptophan.
100. The pharmaceutical formulation of embodiment 98 or 99, further comprising histidine and sucrose.

EXAMPLES

Example 1: Development and Characterization of VHHs Against Human CD8

Discovery and Initial Screening of Anti-CD8 VHHs

Llamas were immunized with either of two antigens, a C-terminal hFc-tagged CD8α receptor (CD8α-Fc) or a C-terminal histidine tag single chain protein in which CD8α is fused to CD8β via a linker (CD8αβ-His). Standard immunization protocols were performed as described in Ghahroudi et al. FEBS 1997 (see also U.S. Pat. No. 6,015,695). Using standard RT-PCR methods, the VHH heavy chain repertoire was amplified and cloned into a phagemid vector to construct an immune phage library. Several rounds of in vitro selections with the phage libraries were then performed using either the CD8αβ-His or CD8α-Fc with varying concentrations, wash times, and elution conditions. After three and four rounds of selections, individual phage clones were characterized by ELISA and subjected to Sanger sequencing.

Figure 3:
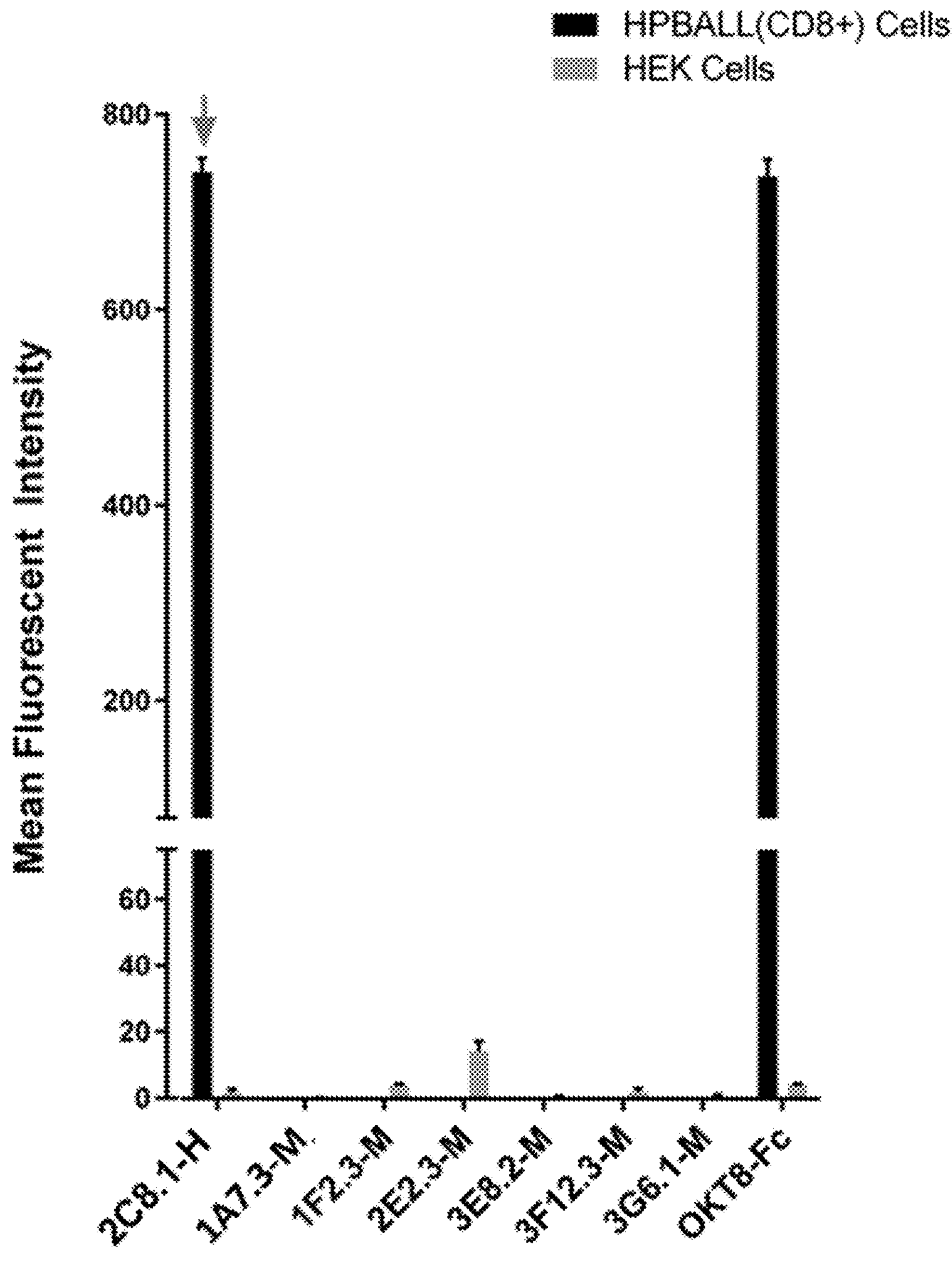
FIG. 3 shows the results of experiments that were performed to assess CD8+ cell-specific binding of VHH-Fc variants as compared to OKT8-Fc.

Additionally, the binding affinity for selected VHH antibodies to both human (huCD8a-Fc) and cynomolgus (cynoCD8a-Fc) CD8 were determined by SPR. In particular, 2C8.1—H (also referred herein as "wt2C8") exhibited acceptable affinity and binding to the huCD8+ HPBALL cells (FIG. 3).

VHH Expression and Purification

Unique sequences identified from phage panning were expressed in a mammalian expression vector containing a C-terminal His tag. The expressed VHHs were subjected to two-step purification: Ni Sepharose excel histidine-tagged protein purification resin (GE Healthcare) followed by size-exclusion chromatography (SEC). Tagless VHHs were also expressed in mammalian cells. Untagged VHHs were subjected to ion exchange purification (SP column) or a recombinant protein A resin (GORE) followed by SEC.

SPR Characterization

The binding affinity for each VHH variant to both human (a one-armed single chain huCD8α/huCD8β-Fc) and cynomolgus monkey (a one-armed single chain cynoCD8α/cynoCD8β-Fc) were determined by Surface Plasmon Resonance (SPR). SPR experiments were carried out on the Biacore T200 (GE Healthcare) at 37° C. using HBS-P+ (GE Healthcare) running buffer. 1.5 μg/mL of CD8αβ-Fc was captured using an anti-HuIgG1 Fc capture kit (GE Healthcare) and monomeric VHHs were added as the analyte in solution at a flow rate of 100 μL/min. The VHH was titrated using a dilution series from 100-0 nM. Sensorgrams were fit to a 1:1 Langmuir model to identify kinetic parameters, including $K_D$, $k_{on}$ and $k_{off}$.

Identification of $CD8^+$ Cell-Specific VHH Variants

Recombinant VHHs fused to a C-terminal huIgG1 Fc were expressed, purified, and screened by FACS against huCD8+ HPBALL cells, a CD8-expressing human T-cell leukemia cell line (DSMZ, Germany). Human embryonic kidney cells (HEK) obtained from ATCC were included as a non-CD8 expressing control cell line. Approximately 300,000 cells were plated in round-bottom 96-well plates in the presence of 100 μL RPMI media supplemented with 10% v/v fetal bovine serum and 1% v/v penicillin-streptomycin (Thermo Fisher Scientific). The VHH variants fused to human-IgG Fc were incubated with the cells at a concentration of 10 μg/mL for 60 minutes at 37° C. Unbound VHH was subsequently washed off and an ALEXA FLUOR® 647 goat anti-human IgG Fc antibody (Jackson Immuno Research, Inc.) was added to the cells at a concentration of 7.5 μg/mL for 60 minutes at 37° C. Cells were then washed twice with phosphate buffered saline (pH 7.4) supplemented with 0.5% bovine serum albumin and analyzed by a FACSCalibur flow cytometer (BD Biosciences). Samples were analyzed in duplicates. OKT8-Fc derived from a four-chain antibody that binds human CD8a served as a positive control.

Results are shown in FIG. 3, which shows that the 2C8 VHH-Fc has comparable affinity and binding to HPBALL cells as OKT8-Fc.

Binding to Whole Blood Cells and PBMCs

2C8 VHH was chosen for further FACS analysis on human whole blood and corresponding PBMC samples. The VHH was expressed as His-tagged monomers and directly labeled with ALEXA FLUOR® 647.

Briefly, whole blood samples from 4 healthy donors (Health center, Genentech) were collected at room temperature and processed less than 30 minutes after blood draw. For each donor, 1 mL sample was kept for direct staining and 4 mL sample was used for peripheral blood monocyte cells (PBMCs) isolation (Ficoll-Paque separation) before staining. To avoid nonspecific binding, whole blood or PBMCs were incubated prior to staining with 20 μL FcR blocking human reagent (Miltenyi Biotech) per 1000 μL or $10^7$ cells respectively. 100 μL of whole blood or $5\times10^4$ PBMCs were distributed into 96 deep-well plates for flow cytometry staining. Fluorescently labeled antibodies were prepared by EDC-NHS mediated conjugation with ALEXA FLUOR® 647 (AF647) dye as per the manufacturer's protocol (Thermo Fisher Scientific).

OKT8-AF647 or VHH-AF647 variants (20 ng/mL), anti-CD14 VioBlue (Miltenyi Biotech; 1/25), anti-CD16 PerCP Cy5.5 (Becton-Dickinson; 1/200), anti-CD4 VioBright-FITC (Miltenyi Biotech; 1/50), anti-CD3 APC-Vio770 (Miltenyi Biotech; 1/50) were added as a premixed antibody cocktail for 10 minutes at room temperature. Samples were then resuspended with 2 mL of red blood cells lysing solution (Becton Dickinson), thoroughly mixed and incubated for 10 minutes at room temperature before centrifugation for 5 minutes at 1500 rpm. After supernatant removal, the pellets were washed with PBS 1×, BSA 0.5% before acquisition on a MacsQuant 10 analyzer (Miltenyi Biotech).

The same protocol was applied for PBMC staining with the exception that no red blood cells lysis step was performed.

Figure 4:
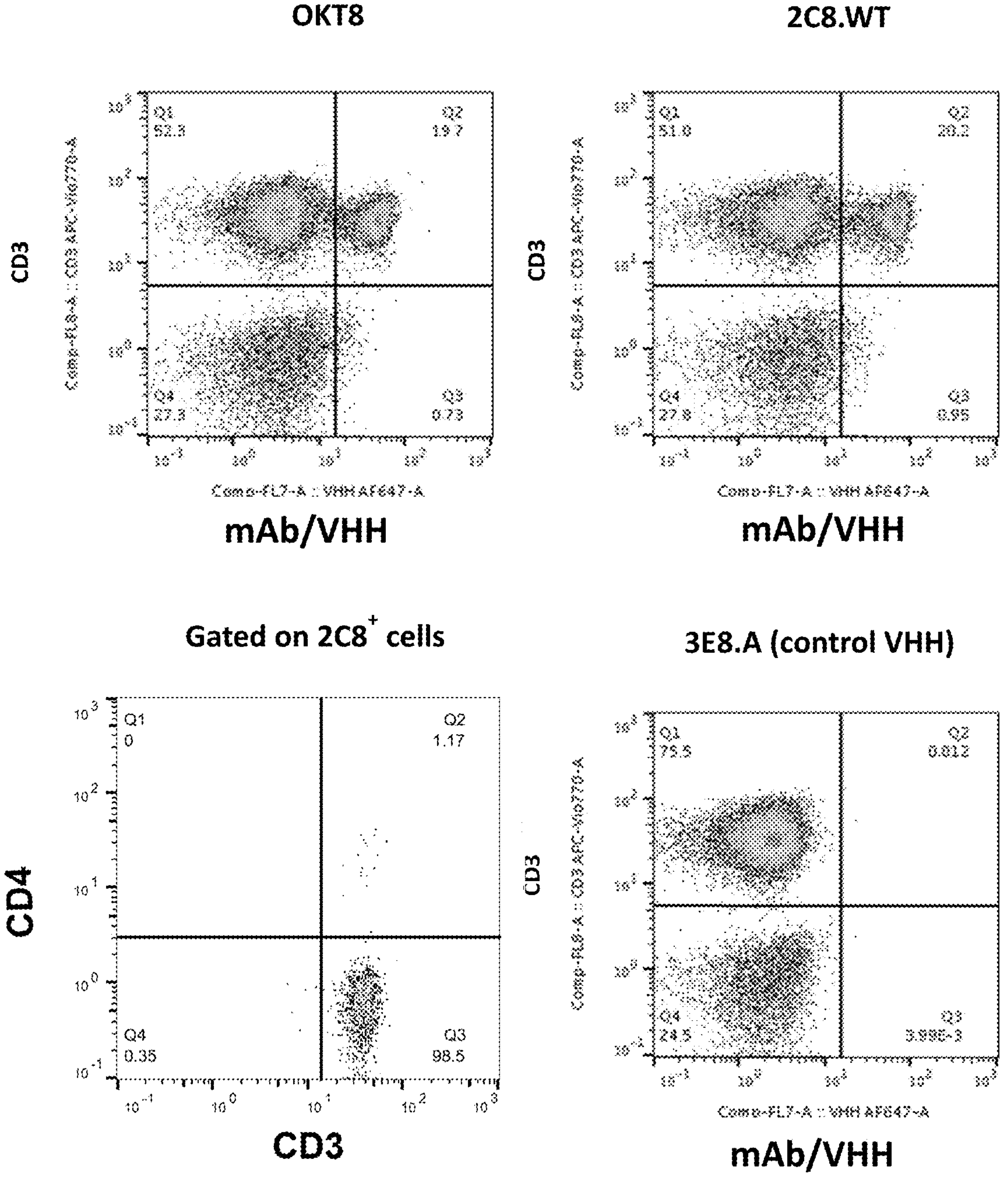
FIG. 4 shows exemplary results of staining of whole blood cell samples from healthy volunteers bound to 2C8 VHH. OKT8 is an anti-CD8 IgG, serving as a positive control. 3E8 VHH is a non-binding negative control.

FIG. 4 shows results using the whole blood cell samples. OKT8 and 2C8 VHH show similar staining patterns, including strong staining of $CD8^+$ T cells and low level of staining of $CD3^-$ cells (e.g., NK cells). Experiments with the PBMC samples yielded similar results. 2C8 VHH binds strongly to only the $CD3^+CD8^+$ T cell population in both whole blood (which contains polynuclear and mononuclear cells) and PBMCs (which contains mononuclear cells only), confirming specificity to human CD8.

Structural Characterization

Figure 5:
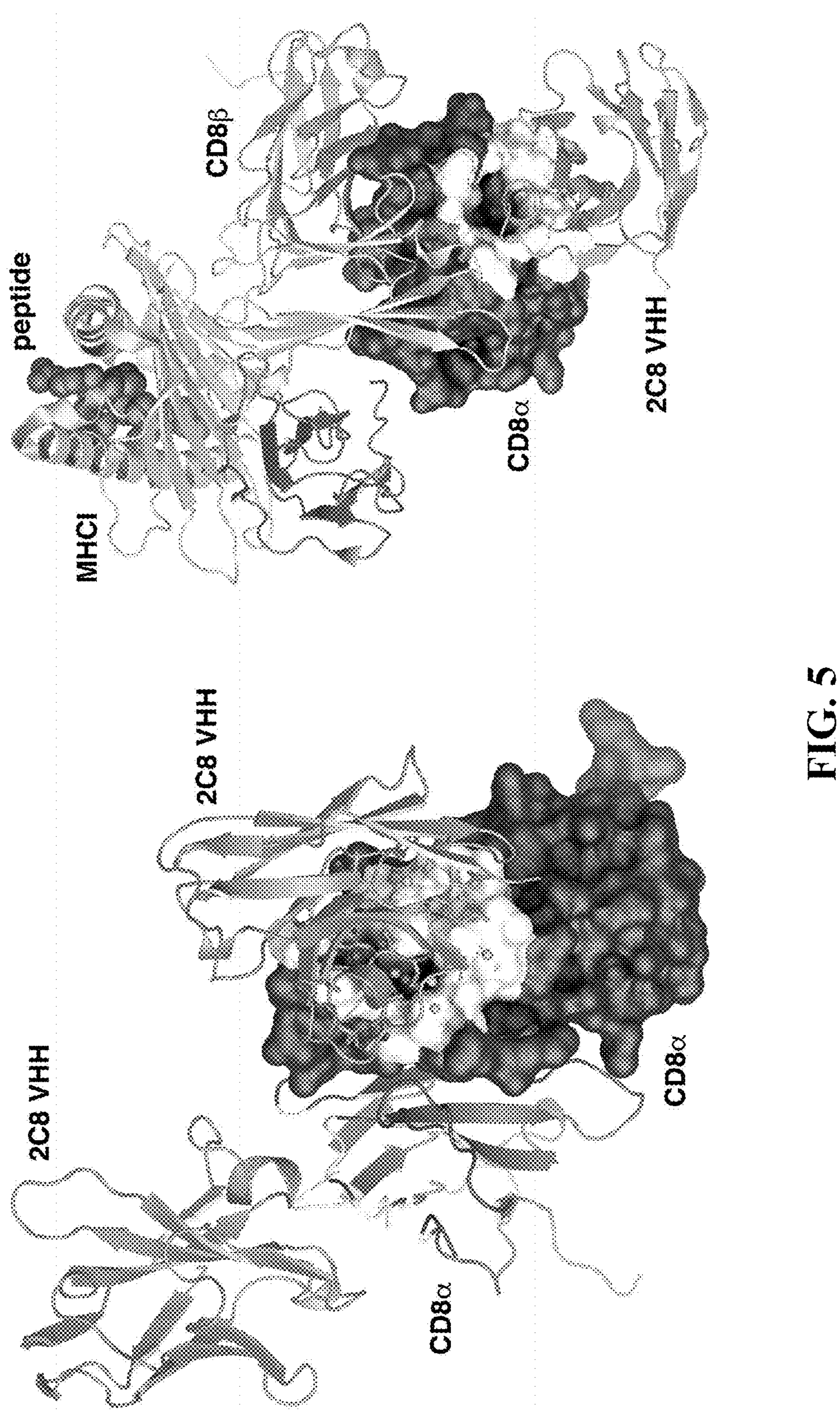
FIG. 5 shows schematics of crystal structures of 2C8 WM. The structure on the left shows 2C8 VHH (light gray) bound to a CD8α/8α homodimer (black with epitope highlighted in white, dimer reconstituted via crystallographic symmetry operators). The structure on the right shows superposition of the 2C8 VHH: CD8α/8α complex (same colors as left panel) onto the published structure of an MHC class I complex with a CD8α/β heterodimer (PDB ID: 3DMM, MHC I is shown in light gray, and CD8β is shown in medium gray).

To determine the epitope of 2C8 on CD8α, the crystal structure of 2C8 bound to homodimeric CD8αα was determined (FIG. 5). 2C8 binds the apex of CD8α and contacts Arg25, Lys42, Gln44, Val45, Leu46, Leu47, Ser48, Pro50, Thr51, Ser52, Gln75, Arg93, Leu94, Gly95, Asp96, and Thr97. These CD8α amino acid residues are each within about 4.5 Å from one or more amino acid residues of 2C8 in the crystal structure. This epitope does not overlap with the binding epitope of mouse CD8αβ in complex with MHCI (Wang et al. J Immunol 2009).

Affinity Maturation Via NNK Walk of VHH CDRs

The initial affinity of 2C8 was deemed suboptimal for sensitive detection of CD8+ cells without some half-life extension mechanism such as PEGylation as described in Rashidian et al. JEM 2017. To identify mutations in 2C8 that improved the affinity, we performed an NNK walk of the CDRs of 2C8 as described in Koenig, et al. JBC 2015.

Briefly, a CDR NNK scanning library was generated in which each mutant contains a single mutation and the entire library includes all 20 amino acids at every CDR position in the VHH. The library was cloned into a phagemid vector and subjected to several rounds of phage panning against CD8α-hFc with decreasing concentrations and increasing wash times. The VHH domain was amplified from the initial library and from the round 3 selected library and subjected to next-generation sequencing (NGS). NGS was done on amplified DNA amplicons using a MiSeq (Illumina) instrument. Enrichment ratios were determined by dividing the frequency of each mutation after 3 rounds of selection by the frequency of each mutation in the initial library.

Upon analysis of the NGS results, we observed that A99G and A100fD were strongly enriched. Generation of 2C8 with the A99G and A100fD mutations improved the affinity by ~10-fold compared to the parental clone.

Humanization of 2C8

We humanized 2C8 by grafting the CDRs (30-35 (H1), 50-65 (H2), and 94-102 (H3)) on IGHV3-23*04. All Vernier positions from the llama were also grafted into their respective locations. We left several llama residues (F37, R45, G47, and L49) in the framework since these are required to maintain binding, stability, and soluble expression of the VHH. After SPR characterization, we determined that only S71 and V78 Vernier residues were required to maintain high affinity binding. Upon humanization, we noticed very poor binding to protein A resins despite having the preferred residue at all protein A contact sites (as described in Henry et al. PLoS One 2016). We inspected potential residues outside those residues that directly contact protein A, which might indirectly alter the conformation of VHH residues important for protein A binding. We identified L49 as one such residue. Upon mutation to Ala (L49A), we observed a large increase VHH recovery after purification via protein A residue (Table 3).

TABLE 3

Yields of purified VHH after protein A and SEC purification

| Clone | Yield (mg from 30 mL Expi293 expression) |
|---|---|
| Hu2C8 | 0.256 |
| Hu2C8.L49A | 2.493 |

Reduction of Binding to Pre-Existing ADAs

Previous clinical data with VHHs has shown pre-existing anti-VHH antibodies in patients [Cordy et al. Clin Exp Immunol 2015; Holland et al. J Clin Immunol 2013; Papadopoulos et al. Cancer Chemother Pharmacol 2015]. We assessed binding of the VHH variants to pre-existing anti-VHH antibodies, introduced four framework mutations (V89T, T110Q, S112Q, and A114 addition) to mitigate risk associated with binding to these pre-existing antibodies.

To perform the VHH anti-drug antibody assay, VHH variants were coated on Maxisorp plates at 2 μg/mL in PBS overnight at 4° C. Plates were washed with PBS+0.5% BSA+0.1% Tween20 (PBSBT) and blocked for 2 hours at 25° C. with 2% BSA. Individual serum samples from 96 different healthy donors were diluted at 1:50 and incubated with VHH-coated and empty wells for 1-2 hours at 25° C. with shaking. After washing, an anti-human Fc-specific HRP 2° antibody (1:10,000) was added for 30 min at 25° C. with shaking. After washing with PBSBT, plates were developed with TMB substrate for 10 minutes and detected at 650 nm.

Figure 6:
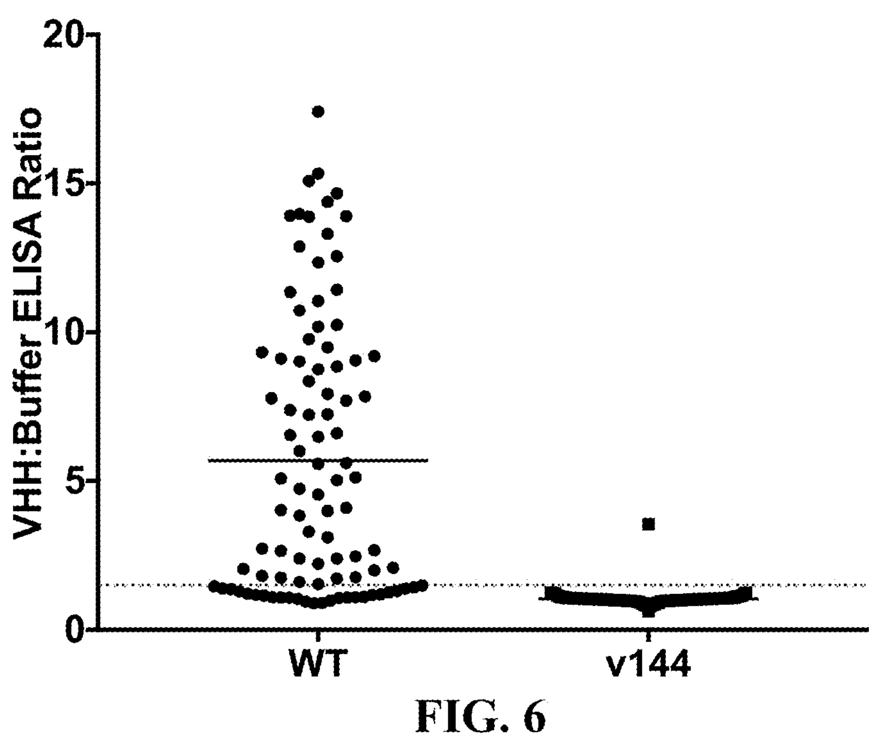
FIG. 6 shows results of experiments that were performed to assess binding of wild-type 2C8 and 2C8.v144 VHH to pre-existing anti-VHH antibodies in blood samples from 96 healthy donors.

As shown in FIG. 6, the framework mutations eliminate binding of the anti-CD8 VHH to pre-existing anti-VHH antibodies pooled from 96 healthy donors.

Overall, we developed several humanized and optimized clones (v130, v142, and v144) that bind strongly to both human and cynomolgus monkey CD8α. FIG. 1 and Table 4 show the amino acid sequences of exemplary VHH clones.

TABLE 4

VHH sequences

| Variant | CDR1 | CDR2 | CDR3 | VHH |
|---|---|---|---|---|
| 2C8 | DYAIG (SEQ ID NO: 6) | CIRIFDRHTYSADSVKG (SEQ ID NO: 8) | GSFWACTRPEGAMDY (SEQ ID NO: 10) | SEQ ID NO: 1 |
| 2C8v130 | DYAIG (SEQ ID NO: 6) | CIRIFDRHTYYADSVKG (SEQ ID NO: 9) | GSFFGCTRPEGDMDY (SEQ ID NO: 11) | SEQ ID NO: 2 |

TABLE 4-continued

| VHH sequences | | | | |
|---|---|---|---|---|
| Variant | CDR1 | CDR2 | CDR3 | VHH |
| 2C8v142 | DYVIG (SEQ ID NO: 7) | CIRIFD RHTYYA DSVKG (SEQ ID NO: 9) | GSFFG CTRPE GDMDY (SEQ ID NO: 11) | SEQ ID NO: 3 |
| 2C8v144 | DYAIG (SEQ ID NO: 6) | CIRIFD RHTYYA DSVKG (SEQ ID NO: 9) | GSFWG CTRPE GDMDY (SEQ ID NO: 12) | SEQ ID NO: 4 |

Tables 5 and 6 show the affinity of 2C8v142 and 2C8v144 to αβ as determined by SPR, respectively. 2C8v144 has high affinity to human and cynomolgus CD8α, and relatively slow off-rate. The 2C8v142 clone contains a W98F mutation in CDR3 compared to 2C8v144, which makes 2C8v142 less prone to oxidation when exposed to high levels of radiation compared to 2C8v144.

TABLE 5

| Affinity of 2C8v142 against human and cynomolgus monkey CD8αβ | | | |
|---|---|---|---|
| | $k_{on}$ (1/M*s) | $k_{off}$ (1/s) | $K_D$ (pM) |
| Human CD8αβ | 1.34e7 | 1.76e−3 | 131.7 |
| Cyno CD8αβ | 1.09e7 | 3.7e−3 | 344.1 |

TABLE 6

| Affinity of 2C8v144 against human and cynomolgus monkey CD8αβ | | | |
|---|---|---|---|
| | $k_{on}$ (1/M*s) | $k_{off}$ (1/s) | $K_D$ (pM) |
| Human CD8αβ | 1.7e7 | 8.448e−4 | 49.7 |
| Cyno CD8αβ | 1.39e7 | 1.9e−3 | 136.6 |

Impact on T Cell Function

In order to evaluate potential impact of 2C8 VHH binding on $CD8^+$ T cell function, we performed in vitro T cell proliferation assays in the presence of 2C8.v130.

Briefly, freshly isolated PBMCs from three healthy donors were washed in PBS 1× and the pellets resuspended at $10\times10^6$ cells per mL in PBS1×. An equal volume of freshly prepared carboxyfluorescein succinimidyl ester (CFSE) 2.5 μM working solution was added (Molecular Probe) before incubation for 5 minutes at room temperature. The labeling was stopped by adding 9 volumes of RPMI, 10% FBS before centrifugation for 5 minutes at 1500 rpm. Two additional washes were performed with RPMI, 10% FBS media before cell count and distribution.

100,000 CFSE-labelled cells were plated in round-bottom 96-well plate for polyclonal stimulation using anti-CD3 at 0.2 μg/mL (Becton Dickinson; pre-coated plate) plus freshly added anti-CD28 at 1 μg/mL or superantigen *Staphylococcal* enterotoxin B (SEB) at 0.4 μg/mL (TruCulture tube; Myriad RBM). For antigen specific stimulation, 500,000 CFSE-labelled cells were plated into round-bottom 96-well plate and 2 μg/mL of CEF peptide pool (Mabtech) was added to each well. 10 ng/mL lipopolysaccharide ("LPS," Sigma) was used as an innate cell activator control and media alone (RPMI, 10% FBS) was used as a negative control. Finally, for all conditions, PBS 1×, 2C8v130 VHH (1 μg/mL and 10 μg/mL final concentration) or Lys2 VHH (10 μg/mL), a control, were added in triplicate for a final volume of 200 μL per well. The control Lys2 VHH binds lysozyme and was described in De Genst, et al. JBC 2005.

Additionally, to evaluate the potential impact of circulating human blood molecules on effect of VHH binding, FBS in the culture medium was replaced by 10% of autologous plasma without stimulation or with SEB 0.4 μg/mL. The plates were incubated for 5 days at 37° C. before analysis.

After plate centrifugation, the supernatant was removed and pellets were washed once with PBS 1×. 100 μL of diluted fixable viability dye solution were added (Live Dead Aqua, ThermoFischer) and cells were incubated 15 minutes at 4° C. before wash with PBS, 0.5% BSA. A premixed antibody cocktail containing anti-CD4 APC-Vio770 (Miltenyi Biotech; 1/50), anti-CD3 Pacific Blue (Becton Dickinson; 1/100), anti-CD8α APC (Becton Dickinson; 1/100) was added to the pellet. Cells were incubated for 20 minutes on ice before PBS wash and flow cytometry analysis using the MacsQuant 10 (Miltenyi Biotech).

Figure 7A:
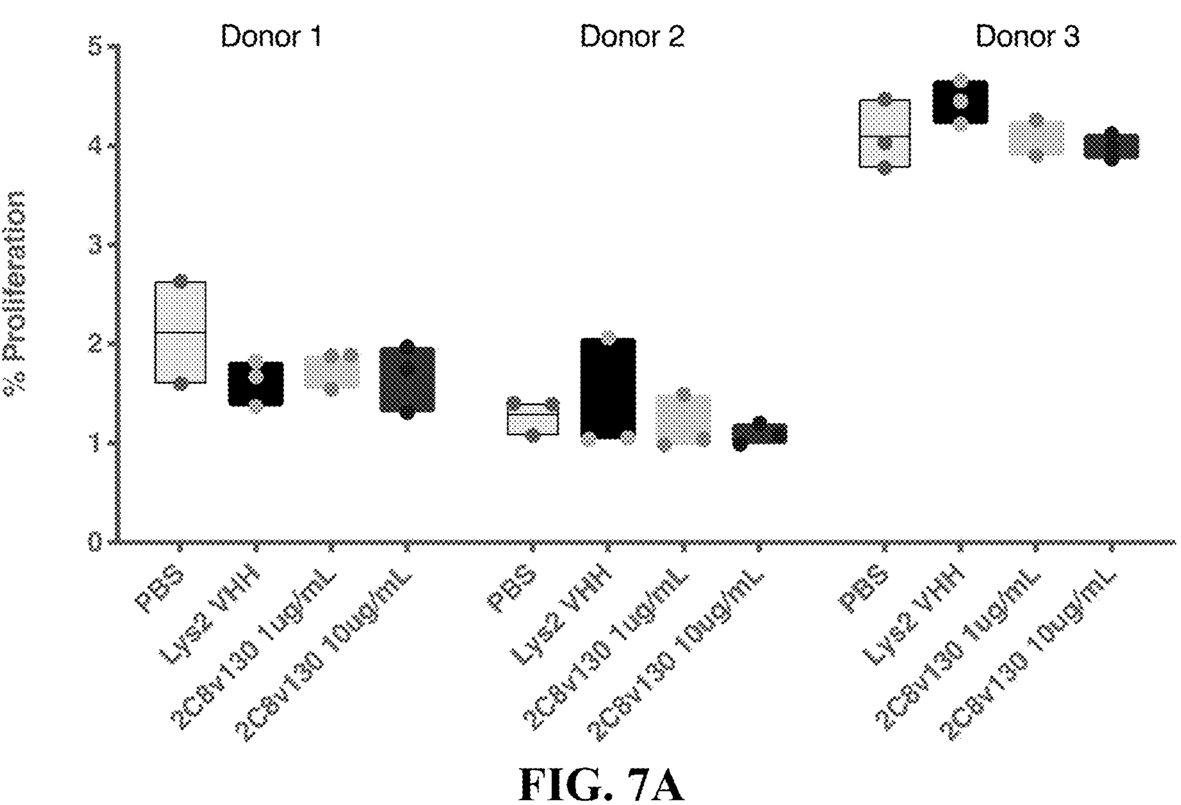
FIG. 7A provides the results of experiments that were performed to assess $CD8^+$ T cell proliferation in the presence of 2C8v130, Lys2 VHH (non-binding control) or PBS (vehicle).
Figure 7B:
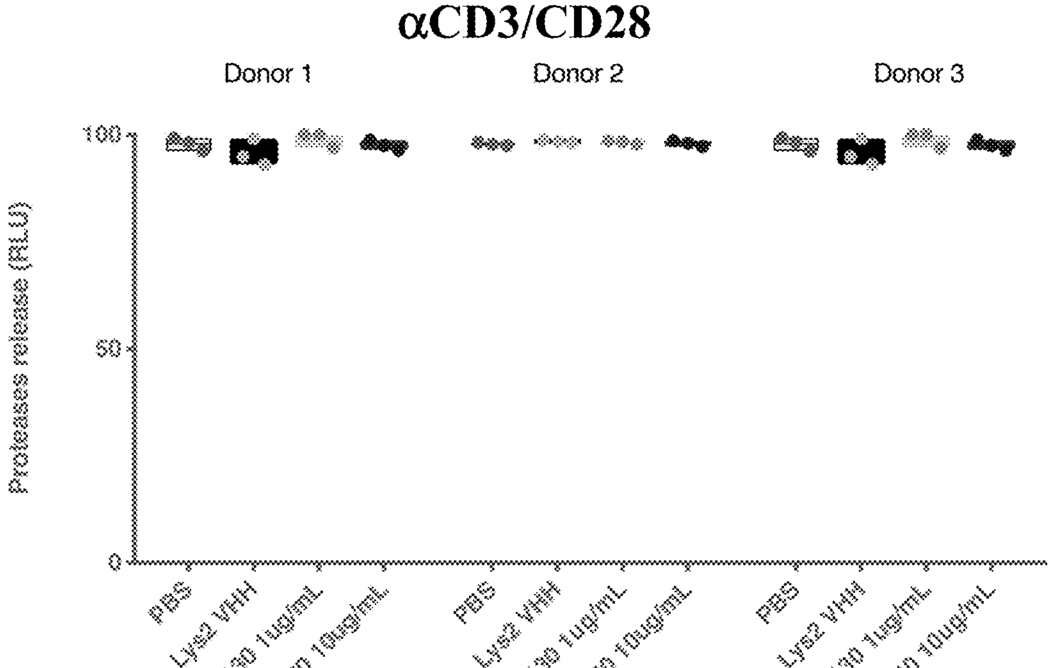
FIG. 7B provides the results of experiments that were performed to assess $CD8^+$ T cell protease release response to polyclonal T cell stimulation via anti-CD3 and anti-CD28 in the presence of 2C8v130, Lys2 VHH (non-binding control) or PBS (vehicle).
Figure 7C:
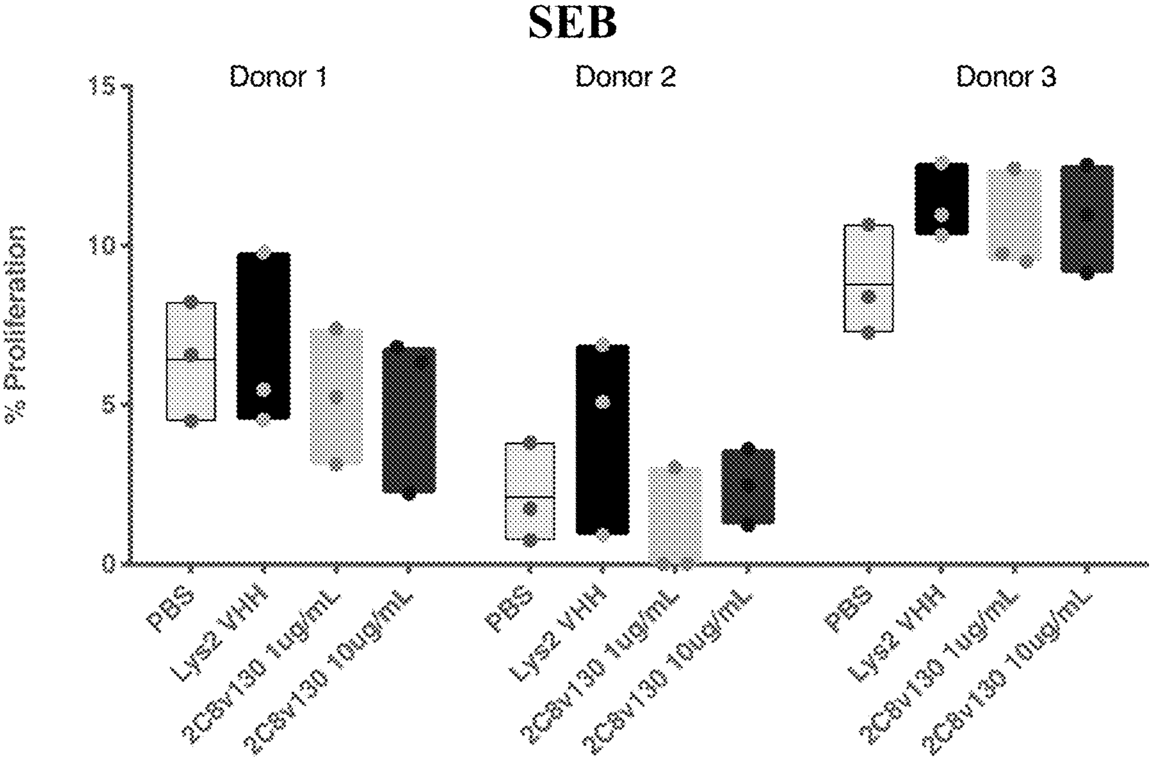
FIG. 7C provides the results of experiments that were performed to assess $CD8^+$ T cell proliferation in the presence of 2C8v130, Lys2 VHH (non-binding control) or PBS (vehicle) following SEB stimulation.
Figure 7D:
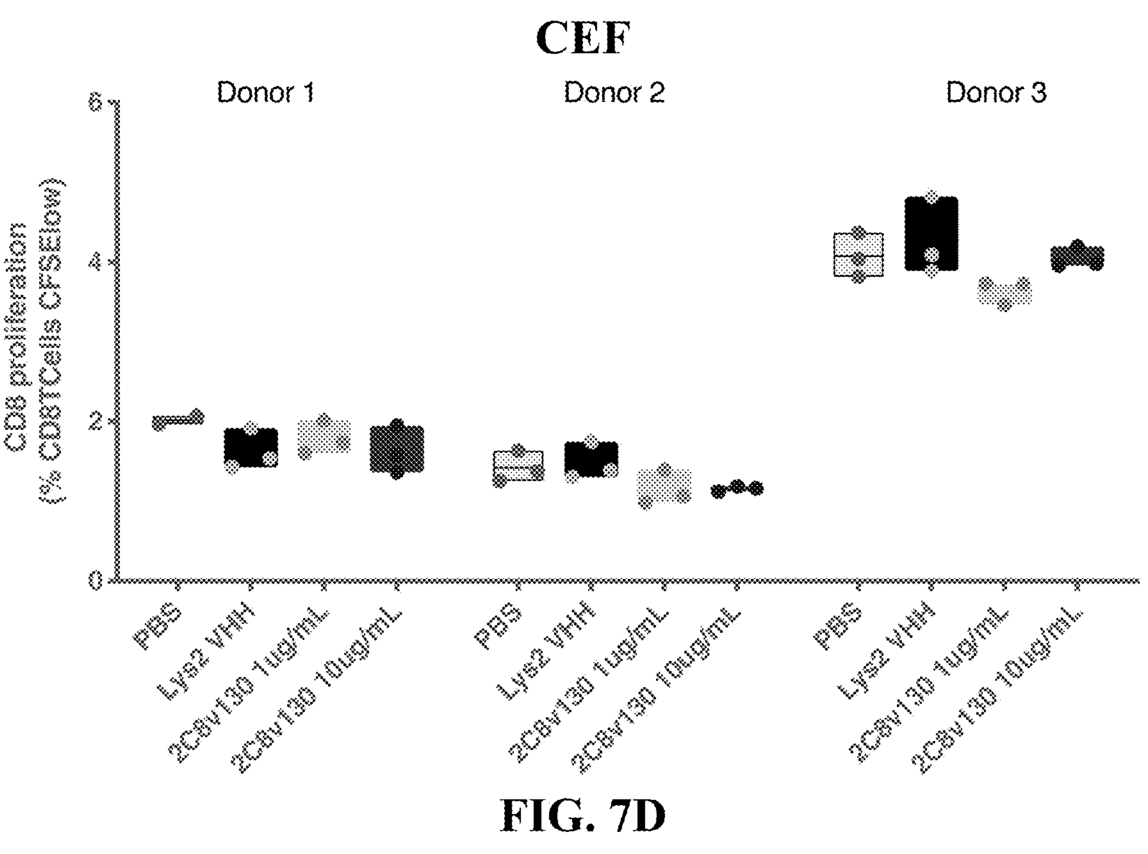
FIG. 7D provides the results of experiments that were performed to assess $CD8^+$ T cell proliferation in the presence of 2C8v130, Lys2 VHH (non-binding control) or PBS (vehicle) following stimulation by CEF peptide pool.
Figure 7E:
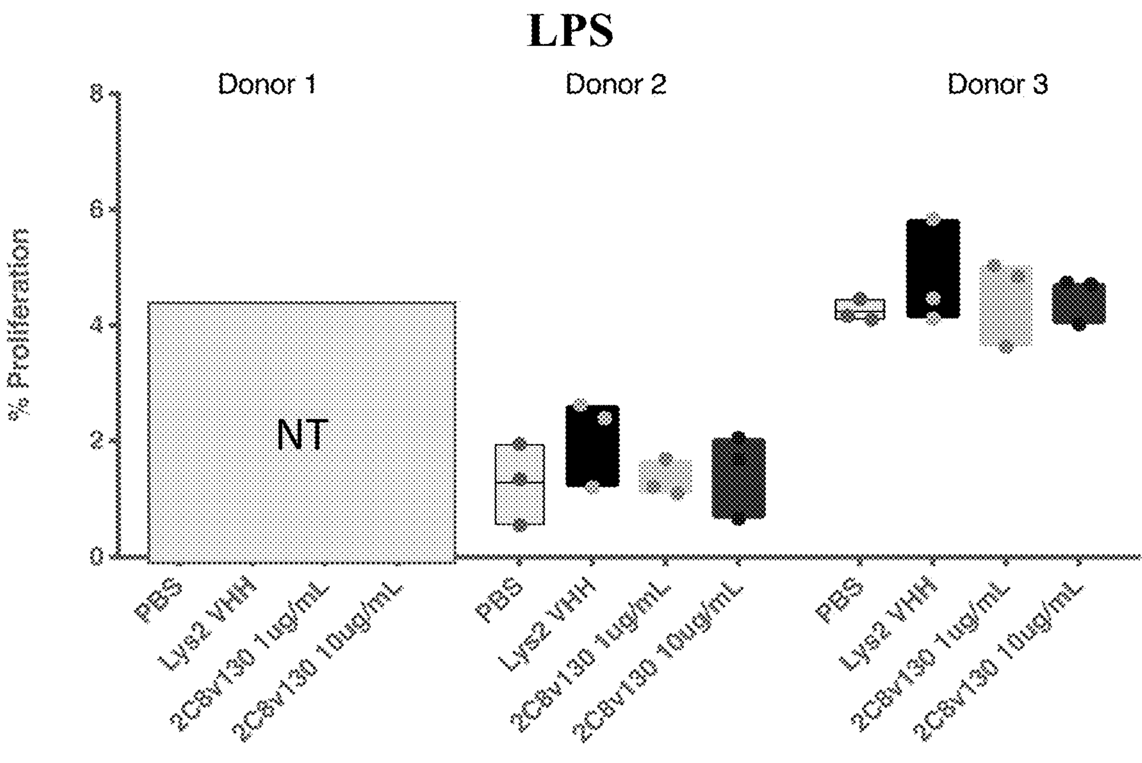
FIG. 7E provides the results of experiments that were performed to assess $CD8^+$ T cell proliferation in the presence of 2C8v130, Lys2 VHH (non-binding control) or PBS (vehicle) following LPS stimulation.

FIGS. 7A-7E show results of the proliferation assays using CFSE labelled human PBMCs (n=3) in presence of high (10 μg/mL) or lower (1 μg/mL) saturating concentrations of 2C8.v130, high concentration (10 μg/mL) of a non CD8-binding VHH (Lys2), or PBS (vehicle). Without stimulation (culture media, FIG. 7A), neither 2C8.v130 nor Lys2-VHH induced background proliferation among the three donors tested, which indicates that the addition of VHH with or without binding to $CD8^+$ cells does not trigger non-specific T cell activation. Upon anti-CD3/CD28 polyclonal stimulation (FIG. 7B), an optimal $CD8^+$ T cell proliferation (more than 90% of CFSE dilution) was obtained for all donors, and addition of 2C8.v130 or Lys2 VHH had no impact on the T cell activation. The superantigen SEB induces a crosslink between MHC-II and TCR, but addition of SEB to the samples did not provide optimal proliferation rate (less than 15% of CFSE low) due to high cell death. Nonetheless, no significant difference was observed across different conditions for a single donor (FIG. 7C). In order to mimic more physiological MHC-I/TCR/CD8 complex engagement, the CEF peptide pool was used to activate TCR specific $CD8^+$ T cells. However, none of the donors tested had detectable reacting $CD8^+$ T cells as the proliferation rates were similar to culture media condition (FIG. 7D), which confirms the absence of VHH-induced background proliferation. In the same manner, upon TLR4 stimulation on monocytes (LPS condition), indirect T cell proliferation was not observed when VHHs were added (FIG. 7E).

Figure 8A:
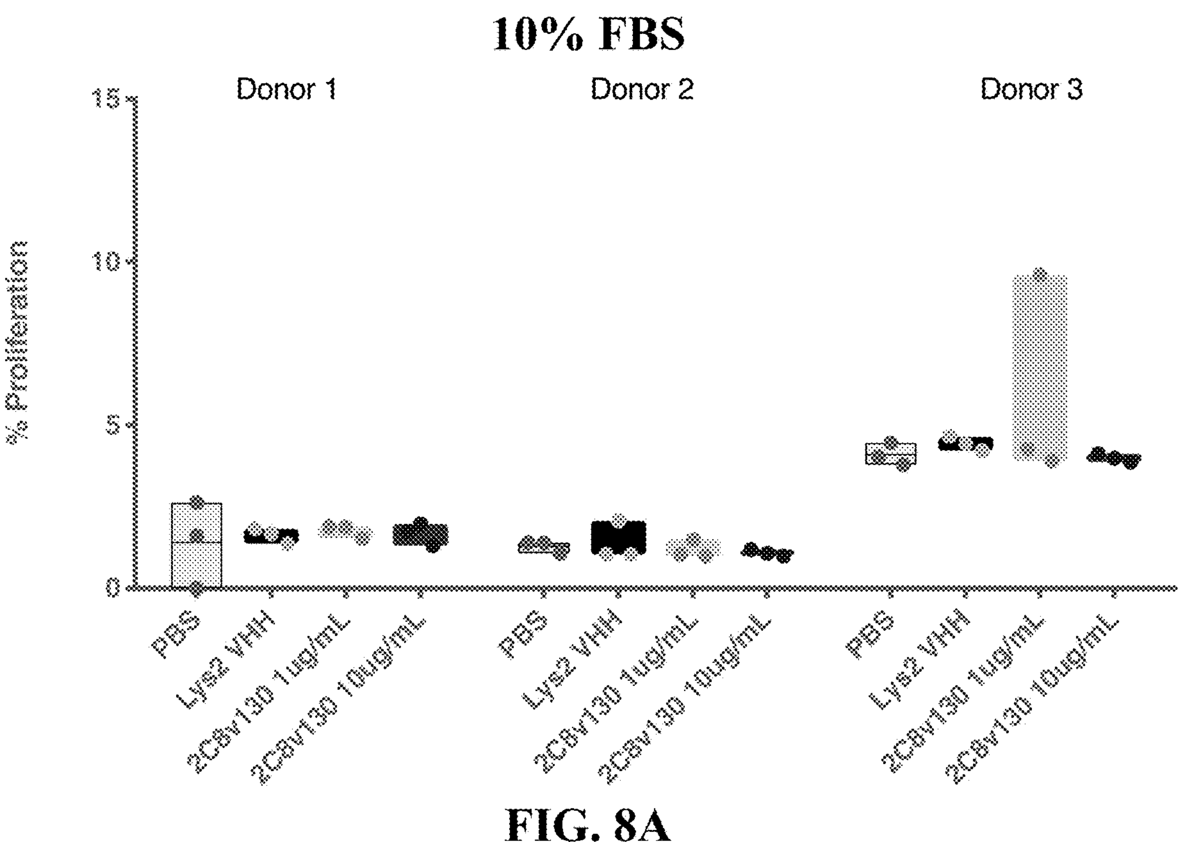
FIG. 8A provides the results of experiments that were performed to assess $CD8^+$ T cell proliferation in the presence of 2C8v130, Lys2 VHH (non-binding control) or PBS (vehicle), in which 10% FBS was used as culture medium.
Figure 8B:
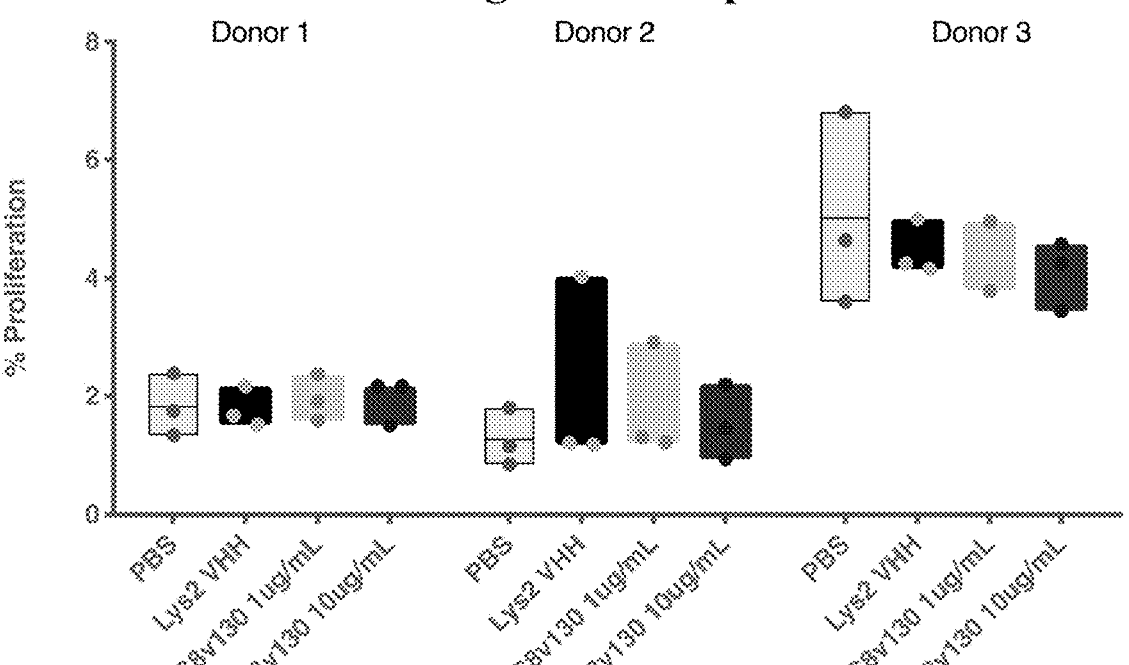
FIG. 8B provides the results of experiments that were performed to assess $CD8^+$ T cell proliferation in the presence of 2C8v130, Lys2 VHH (non-binding control) or PBS (vehicle), in which 10% autologous donor plasma was used as culture medium.
Figure 8C:
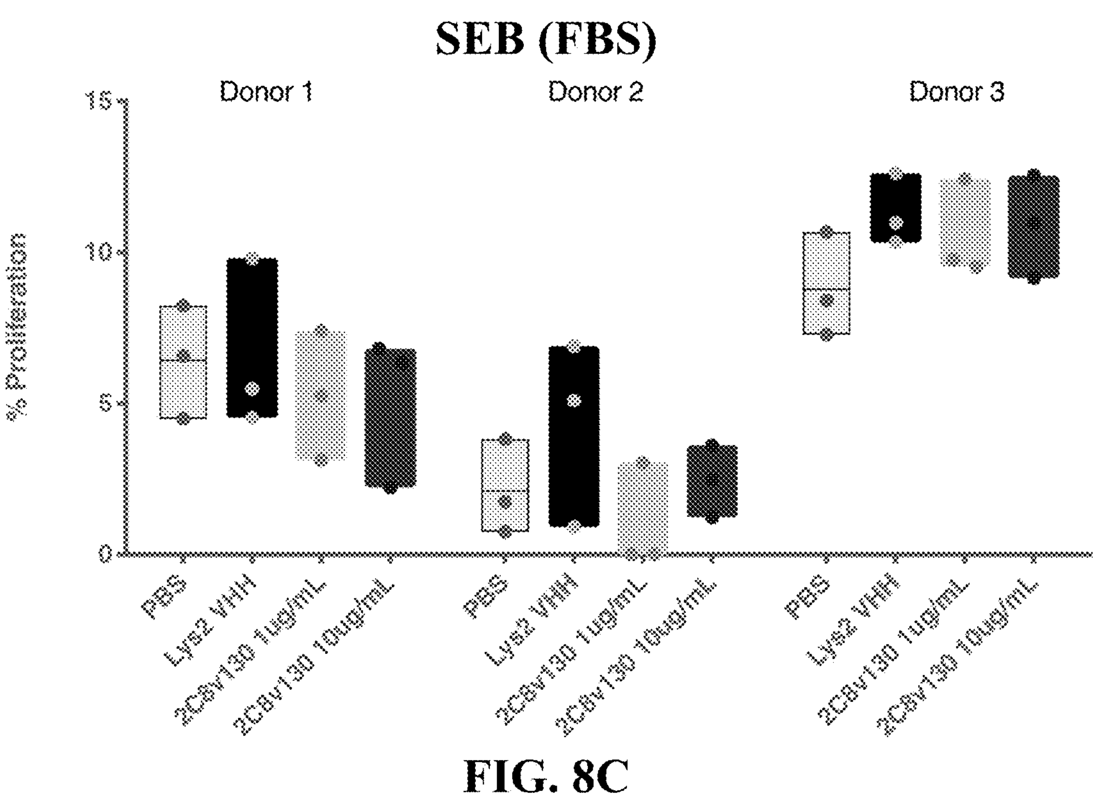
FIG. 8C provides the results of experiments that were performed to assess $CD8^+$ T cell proliferation in the presence of 2C8v130, Lys2 VHH (non-binding control) or PBS (vehicle) following SEB stimulation, in which 10% FBS was used as culture medium.
Figure 8D:
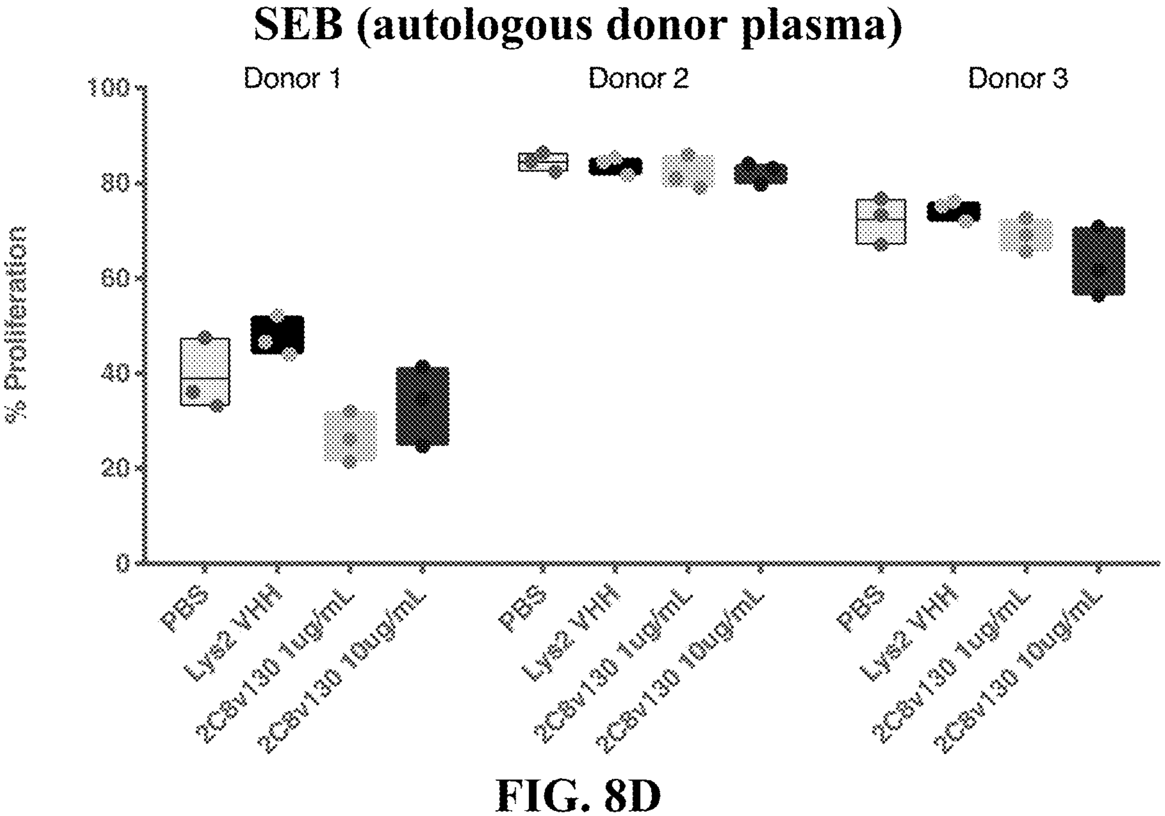
FIG. 8D provides the results of experiments that were performed to assess $CD8^+$ T cell proliferation in the presence of 2C8v130, Lys2 VHH (non-binding control) or PBS (vehicle) following SEB stimulation, in which 10% autologous donor plasma was used as culture medium.

FIGS. 8A-8D compare results of proliferation assays with 10% FBS or autologous donor plasma as the culture media. Autologous donor plasma samples were obtained before PBMC isolation and were used in the proliferation assays to mimic physiological conditions. Without stimulation, no difference was observed between experiments using 10% FBS media or autologous donor plasma for all donors (FIGS. 8A and 8B). Thus, in the presence of soluble human plasma factors, VHHs also do not induce background T cell proliferation.

Example 2: Evaluation of 2C8v144 VHH for Molecular Imaging

Labeling of 2C8 VHHs

Procedures for the production of RESCA (restrained complexing agent)-modified VHH and $^{18}F$-A1F-RESCA-modified VHH, including an $^{18}F$ control VHH and an $^{18}F$ anti-CD8 VHH, were adapted from a previously described protocol (Cleeren F. et al. Nature Protocols 13, 2330-2347 (2018)). An exemplary RESCA has the chemical structure of Formula (I). Briefly, RESCA-conjugated VHH was added to a mixture of $^{18}$F-fluoride in a reaction medium consisting of either sodium acetate or sodium acetate with methionine and N-acetyl-tryptophan. The reaction mixture was purified using a desalting column equilibrated with a formulation buffer conditioned with histidine, methionine, N-acetyl tryptophan, and sucrose, which decreases the oxidation rate on the VHH. As a control, the formulation buffer was conditioned with phosphate buffer saline. The histidine formulation buffer was carefully controlled for pH and temperature to limit the dissociation rate of $^{18}$F-A1F from RESCA. The final product was assayed for protein concentration, protein purity, and radiochemical purity by SE-HPLC, as well as target binding (immunoreactive fraction, as appropriate) by SE-HPLC and SPR.

$^{18}$F control VHH using 2C8v145 VHH and $^{18}$F anti-CD8 VHH using 2C8v144 were obtained in 40-60% radiochemical yield (non-decay corrected). The final product exhibited a specific activity range of 3.0-8.0 Ci/μmol, a radiochemical purity exceeding 95%, and for $^{18}$F anti-CD8 VHH, an immunoreactive fraction exceeding 94%.

Without being bound by any theory or hypothesis, conjugation of the anti-CD8 VHH to a radionuclide label may result in oxidation of one or more VHH residues, such as tryptophans, which leads to diminished CD8 binding capacity. Use of anti-oxidant compounds, such as methionine and/or N-acetyl tryptophan, in the conjugation reaction buffer, purification buffer, and/or formulation buffer, can reduce oxidation of the VHH residues, thereby improving yield of functional labeled anti-CD8 WM.

PET Imaging of Chimeric CD8$^+$ Tumor Xenografts in Mice

The sensitivity and dynamic range of the $^{18}$F-anti-CD8 VHH were assessed by performing PET imaging of chimeric CD8+ tumor xenografts in mice.

Briefly, HPBALL, a CD8-expressing human T-cell leukemia cell line (DSMZ, Germany) was mixed in varying ratios with Daudi, a human lymphoma cell line (DSMZ, Germany) devoid of CD8 to generate chimeric tumors of varying CD8 concentration for PET imaging using $^{18}$F-anti-CD8 WM. Briefly, female CB17.SCID.bg mice were inoculated with 10 million cells each in a 50:50 mix of HBSS: matrigel, subcutaneously into the dorsal thoracic region. Once tumors reached approximately 400 $mm^3$ in size, the animals were injected via the tail vein with $^{18}$F-anti-CD8 VHH and subject to dynamic 60 minute PET scans on an Inveon PET/computed tomography (CT) scanner (Siemens Preclinical Solutions, Inc.).

To evaluate the CD8 expression after completion of PET imaging, the chimeric tumors were excised from the mice and dissociated using the gentleMACS Octo Dissociator (Miltenyi Biotec) according to the manufacturer's protocol. The resulting cell suspension was then passed through a 70 μm cell strainer (Corning) to remove aggregates. Tumor cells were then counted and 300,000 cells were plated in round-bottom 96-well plates in the presence of 100 μL RPMI media. Cells were stained with 20 nM of ALEXA FLUOR® 647-tagged OKT8 anti-CD8 antibody (60 minutes, 4° C.) as well as Sytox orange dead cell stain (15 minutes, 4° C.) (Thermo Fisher Scientific). Cells were washed and then analyzed by a FACS Calibur flow cytometer to determine the percentage of CD8$^+$ cells in the tumor.

Figure 9:
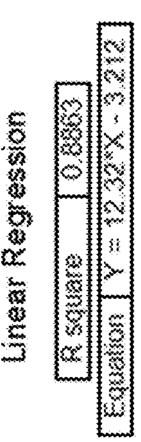
FIG. 9 shows results of experiments that were performed to assess CD8 imaging capacity by $^{18}F$-anti-CD8 VHH in chimeric HPBALL/Daudi tumor xenograft mice.

As shown in FIG. 9, the $^{18}$F-anti-CD8 VHH allowed clear visualization of CD8$^+$ tumor cells by PET imaging with as low as 10% CD8$^+$ HPBALL cells. The results also demonstrate a clear correlation between PET uptake (% ID/g) and concentration of CD8$^+$ HPBALL cells. Based on previous FACs data, it was estimated that each HPBALL cell has about 55,000-85,000 copies of CD8 molecules, while each naïve CD8$^+$ T cell has 200,000-300,000 copies of CD8 molecules. $^{18}$F-anti-CD8 VHH is a sensitive imaging agent that can detect low levels (about 1-30 nM sensitivity) of CD8 expression on tumor cells.

PET Imaging of TALL1 Tumor Xenografts in Mice $^{18}$F-anti-CD8 VHH and a $^{89}$Zr-One Armed ("OA")-anti-CD8 antibody (see, International patent application publication No. WO2019/033043A2) were used to image TALL1 tumor xenografts in mice. TALL1 is a low CD8 expressing leukemia cell line. Based on previous FACS data, it was estimated that each TALL1 cell has about 12,000-15,000 copies of CD8 molecules.

Briefly, female CB17.SCID.bg mice were inoculated subcutaneously into the right flank with 10 million TALL1 cells in a 50:50 mix of HBSS:matrigel. Animals were grouped out for PET imaging once tumors reached approximately 400 m3 in size. For imaging with the $^{89}$Zr-OA-anti-CD8 antibody, the animals were injected via the tail vein and subject to static PET scans at day 0, 1, 2 and 5. For imaging with 18F-anti-CD8 VHH, the animals were injected via the tail vein and subject to dynamic 60-minute PET scans as before.

Region of interest (ROI) measurements were made on multiple axial slices of the tissues using IRW software (Siemens Preclinical Solutions, Inc.). Decay-corrected signal intensity of organs was measured as a percentage of the injected dose per gram (% ID/g), assuming 1 cc equivalency in 1 gram of soft tissue.

Figure 10:
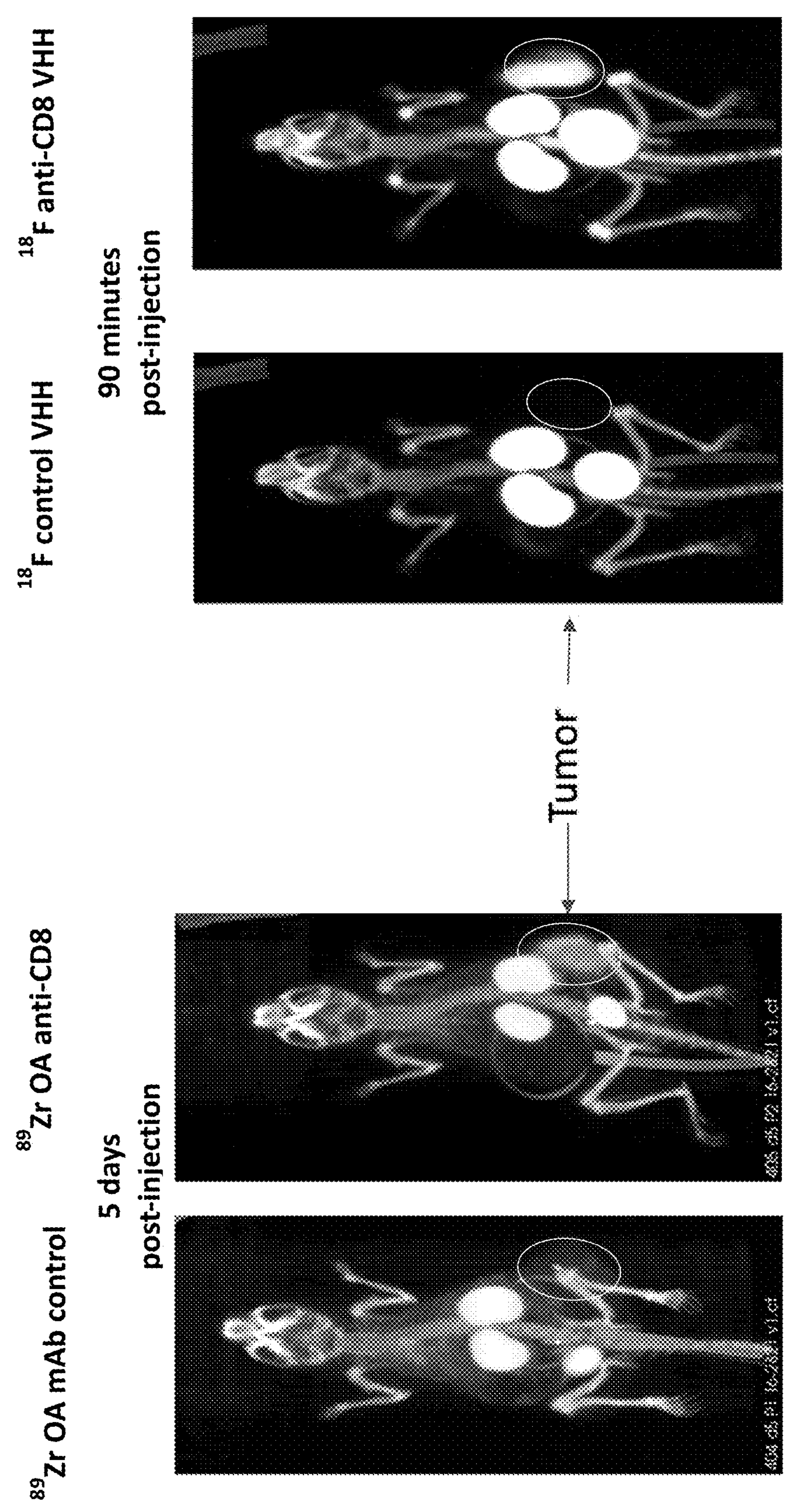
FIG. 10 shows PET MIP of a TALL1 tumor xenografted mouse on Day 5 (i.e., sixth days) after injection (Day 0) with $^{89}Zr$-OA mAb control or $^{89}Zr$-huOKT8.v1-OA (left), or after 90 minutes after injection with $^{18}F$-control VHH or $^{18}F$-anti-CD8 VHH (right).

$^{18}$F-anti-CD8 VHH allows rapid visualization of low CD8-expressing TALL1 xenograft tumors within 1 hour. As shown in FIG. 10, CD8-expressing TALL1 xenograft tumor could be clearly visualized after 90-minutes post-injection, and a high tumor-to-blood ratio of 14 was achieved. Imaging using $^{18}$F-anti-CD8 VHH could be completed within 0.5-4 hours. In comparison, the $^{89}$Zr-OA-anti-CD8 antibody is suitable for meaningful imaging at longer time points, i.e., 1 to 5 days, post injection. Because of its small size, the $^{18}$F-anti-CD8 VHH penetrates tissues very rapidly and exhibits rapid renal clearance, facilitating additional PET scans (such as FDG PET) in the same patient later in the same day, or repeated CD8 scans as soon as the next day. Compatibility with $^{18}$F labeling (or other labels such as $^{68}$Ga) affords imaging procedures with the anti-CD8 VHH that result in relatively low radiation burden to the patient, so that additional scans may be performed throughout a course of treatment within common dosimetry guidelines for human patients. For example, with $^{18}$F-anti-CD8 VHH, it would be possible to re-image the same patient up to about 5 times over a typical months- or years-long course of treatment and follow-up.

PET Imaging Studies in Rhesus Monkeys

Figure 11:
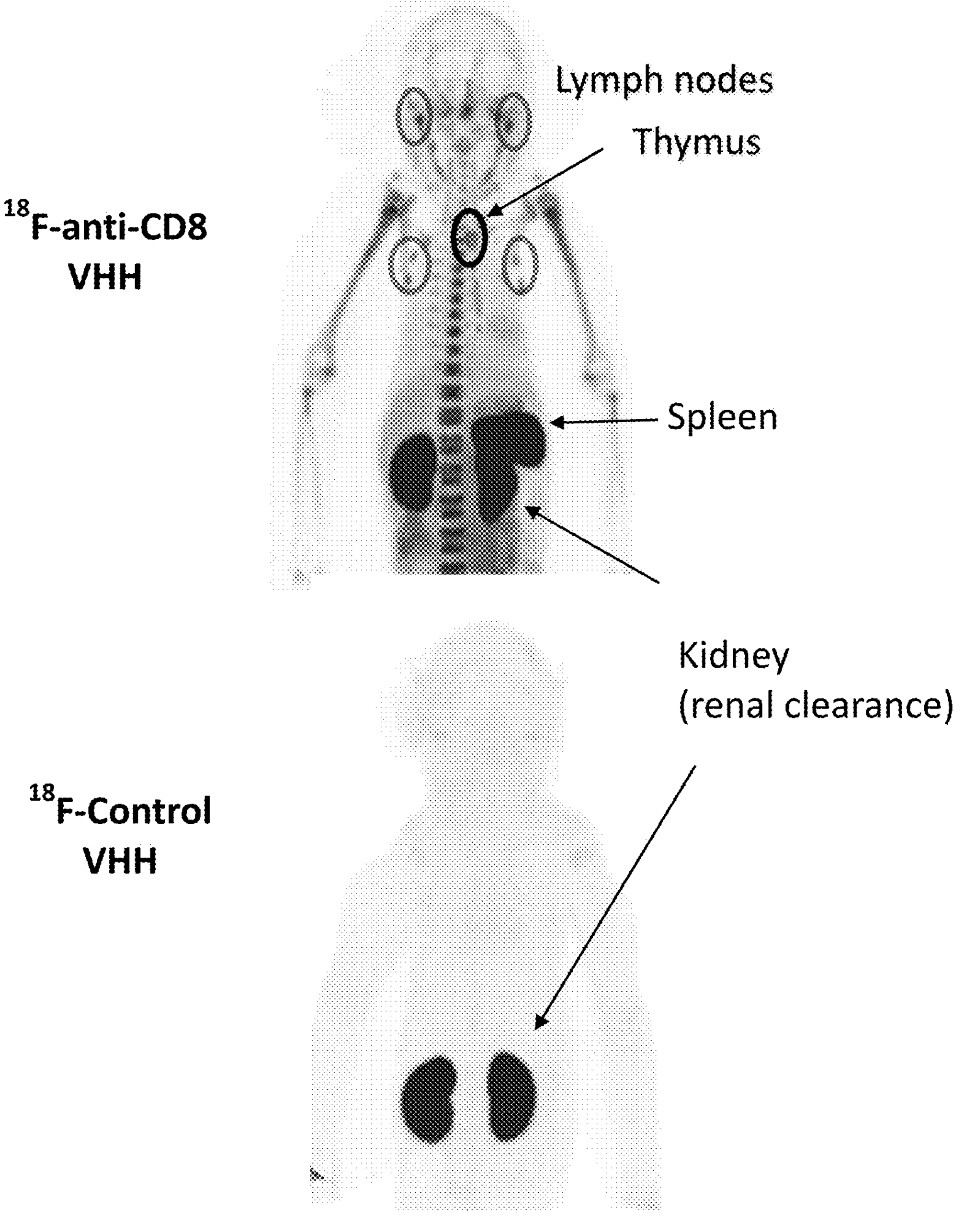
FIG. 11 shows PET MIP images of rhesus monkeys one hour post injection with $^{18}F$-anti-CD8 VHH (top) or $^{18}F$-control VHH (bottom).

Imaging experiments were performed with $^{18}$F-anti-CD8 VHH in a rhesus monkey to determine whether uptake could be detected in tissues that are normally CD8-rich. A rhesus monkey (2.5 kg) was injected with 64 micrograms $^{18}$F-anti-CD8 VHH containing a 1.2 mCi radiation dose. CD8-rich tissues, such as lymph nodes, thymus and spleen, could be imaged clearly within 1 hour of injection. For example, the top figure of FIG. 11 shows a PET MIP image one hour post injection. By contrast, CD8-rich tissues were not visible in a PET MIP image one hour following injection with $^{18}$F-control VHH (FIG. 11 bottom). Only clearance to the kidneys was conspicuous.

Example 3: Methods of Using CD8 Imaging for Determining the Efficacy of Immunotherapy for Cancer, Autoimmune Disease or Condition, Transplant Rejection or Graft-Versus-Host Disease A CD8 binding agent described herein, such as $^{18}$F-anti-CD8 VHH, is used to assess tumor and lymph node infiltration by $CD8^+$ cells. Such imaging is used to identify immune phenotypes that are predictive of patient prognosis and/or response to immunotherapy. Such imaging is used to determine the prevalence of $CD8^+$ T-cells in diseased tissues (e.g., tumors) and other lymph nodes, for example. Such imaging is used to select immunotherapy agents or combination therapy agents that include one or more immunotherapy agents for patients having cancer, an autoimmune disease or condition (such as arthritis, colitis, or celiac disease), transplant rejection, or graft-versus-host disease.

In all embodiments disclosed herein, the immunotherapy for a cancer patient is, for example, any anti-PD1 agent or anti-PDL1 agent disclosed herein, such as monoclonal antibodies to treat cancer, bi-specific antibodies that bind T cells and to a tumor associated protein, bi-specific antibodies that bind NK cells and to a tumor associated protein, cytokines, CAR-T cell therapies, non-specific cancer immunotherapies and adjuvants, and immune checkpoint inhibitors. Bispecific antibodies that bind T cells and to a tumor associated protein include, for example anti-CD3 bispecific antibodies. Bispecific antibodies that bind NK cells and to a tumor associated protein include, for example, anti-CD16 (FcgammaRIII) bispecific antibodies, anti-CD16A bispecific antibodies, anti-CD56 bispecific antibodies, anti-NKp46 bispecific antibodies, and any other NK-cell binding bispecific antibodies.

In some embodiments, the CD8 binding agent (e.g., $^{18}$F-anti-CD8 VHH) can be used for the treatment, diagnosis, prognosis, companion diagnostic, and monitoring the progression/remission of a disease such as cancer, autoimmune disease or condition, transplant rejection, or graft-versus-host disease, as described herein.

In some embodiments, the CD8 binding agent (e.g., $^{18}$F-anti-CD8 VHH) can be used for imaging a subject who has experienced treatment failure with an immunotherapeutic agent for a disease (such as cancer, autoimmune disease or condition, transplant rejection, or graft-versus-host disease), wherein the imaging results explain the mechanism(s) of treatment failure. For example, the subject may receive atezolizumab combinations, and fail to respond to the treatment. The imaging results may reveal that the subject has lost CD8+ tumor cells, or still has CD8+ tumor cells but the therapeutic agents are exhausted or no longer potent against the CD8+ tumor cells.

Example 4: Methods of Using CD8 Imaging for Microbiome Research and Immune Phenotype Identification A CD8 binding agent described herein, such as $^{18}$F-anti-CD8 VHH, can be used to assess tumor and lymph node infiltration by $CD8^+$ cells. Such imaging is used to identify immune phenotypes that underlie microbiome signatures predictive of patient prognosis and/or response to cancer immunotherapy.

Furthermore, the CD8 binding agent described herein, such as $^{18}$F-anti-CD8 VHH, can be used to identify microbiome signatures that are associated with particular whole-body patterns in the biodistribution of $CD8^+$ T-cells. Such imaging is used to determine the prevalence of $CD8^+$ T-cells in tumors and other lymph nodes, for example. Such imaging is used to select the most robust microbiome biomarkers, even when the direct associations with outcome are noisy or weak.

Resident gut bacteria may affect patient responses to cancer immunotherapy. See, e.g., Gopalakrishnan et al. (2018) *Science.* 359(6371): 97-103. Accordingly, identifying key microbial strains associated with patient responsiveness to cancer immunotherapy may be useful for identifying appropriate treatment regimens for cancer patients. The CD8 binding agent described herein, such as $^{18}$F-anti-CD8 VHH, may be used to identify the microbiome profile(s) (e.g., gut flora composition(s)) that correlate with patient responsiveness to immunotherapy (e.g., an immunotherapy discussed herein).

Briefly, gut microbiome samples (e.g., fecal samples) are acquired from cancer patients who are to undergo immunotherapy (e.g., an immunotherapy described elsewhere herein). A CD8 binding agent described herein, such as $^{18}$F-anti-CD8 VHH, is administered to each of the patients prior to their undergoing cancer immunotherapy, and tumor and lymph node infiltration by $CD8^+$ cells is assessed in each patient. Next, the patients each receive cancer immunotherapy (e.g., an immunotherapy described herein). The CD8 binding agent described herein, such as $^{18}$F-anti-CD8 VHH, is administered to the patients again following the cancer immunotherapy, and tumor and lymph node infiltration by $CD8^+$ cells is assessed a second time in each patient. The level of CD8 infiltration in the patient's tumor(s) and lymph nodes following immunotherapy is assessed, and each patient's microbiome profile (e.g., the types of microbes, as well as the abundance of each type of microbe, present in the gut microbiome sample) is determined. The key microbial strains present in the gut microbiome samples of the patients who demonstrate $CD8^+$ T cell infiltration to the tumor(s) and lymph nodes are identified.

Following the identification of key microbial strains in patients who have $CD8^+$ T cell infiltration to the lymph nodes and/or tumor, a microbiome drug comprising the key microbial strains is made from donor stool obtained from such patients. The microbiome drug is administered to patients who do not demonstrate $CD8^+$ T cell infiltration into the lymph nodes or tumor. Alternatively, a FMT (fecal microbiota transplant) procedure is performed on patients who do not demonstrate $CD8^+$ T cell infiltration into the lymph nodes and/or tumor using donor stool collected from patients who demonstrate $CD8^+$ T cell infiltration to the lymph nodes and/or tumor. In some embodiments, the FMT or microbiome drug transforms a patient who does not exhibit $CD8^+$ infiltration into the lymph nodes and/or tumor upon cancer immunotherapy into a patient who does respond to cancer immunotherapy.

In some embodiments, CD8 imaging is performed on the patient who does not exhibit $CD8^+$ infiltration into the lymph nodes and/or tumor prior to FMT or prior to administration of the microbiome drug. Following FMT or administration of the microbiome drug, the patient receives immunotherapy. Following immunotherapy, imaging is performed on the patient in order to determine if the FMT or the microbiome drug results in increased $CD8^+$ infiltration into the lymph nodes and/or tumor. In some embodiments, if increased $CD8^+$ infiltration is observed in response to the cancer immunotherapy treatment after FMT or other microbiome drug, then the FMT or other microbiome drug is considered to have been successful.

The CD8 imaging agent used in conjunction with microbiome research and discovery can be any CD8 binding agents described herein, such as $^{18}$F-anti-CD8 VHH, using wt2C8 VHH, 2C8v130 VHH, 2C8v142 VHH or 2C8v144 VHH.

In some embodiments, the cancer immunotherapy is a checkpoint inhibitor. In some embodiments, the cancer immunotherapy is a T-cell targeting therapy. In some embodiments, the T-cell targeting therapy is a T-cell bispecific, trispecific, or multispecific antibody or antigen-binding fragment thereof. In some embodiments, the cancer immunotherapy is a NK cell targeting therapy. In some embodiments, the NK cell targeting therapy is a bispecific, trispecific, or multispecific antibody or an antigen-binding fragment thereof.

In some embodiments, CD8 imaging using a CD8 binding agent described herein, such as $^{18}$F-anti-CD8 VHH, can be used to assess tumor and lymph node $CD8^+$ infiltration before, during, and after administration of a checkpoint inhibitor or an immune modulating molecule, such as a CD16 or CD3 targeting moiety. Such imaging is used to determine microbiome biomarkers that are associated with efficacy of a checkpoint inhibitor or an immune modulating molecule, such as a CD16 or CD3 targeting moiety.

The checkpoint inhibitor as used in this example can be any checkpoint inhibitor. In some embodiments, the checkpoint inhibitor is an anti-PD1 or an anti-PDL1 antibody. In some embodiments, the checkpoint inhibitor is atezolizumab (TECENTRIQ®).

The immune modulating molecules can be any molecule that affects CD8 cell proliferation and infiltration. Examples include T-cell bispecific molecules such as antibodies that bind CD3 and a tumor associated antigen and molecules that bind CD16 and a tumor associated antigen.

The Exemplary Embodiments and Examples are offered for illustrative purposes only, and are not intended to limit the scope of the present application in any way. Indeed, various modifications in addition to those shown and described herein will become apparent to those skilled in the art from the foregoing description and fall within the scope of the appended claims.

What is claimed is:

1. A CD8 binding agent comprising a variable domain of the heavy chain of a heavy chain antibody (VHH domain) wherein the VHH comprises a CDR1 comprising an amino acid sequence of SEQ ID NO:6 or SEQ ID NO:7; a CDR2 comprising an amino acid sequence of SEQ ID NO:8 or SEQ ID NO:9; and a CDR3 comprising an amino acid sequence of SEQ ID NO:10, SEQ ID NO:11, or SEQ ID NO: 12, and wherein the CD8 binding agent specifically binds a human CD8 with a $K_D$ of about 0.15 nM or less.

2. The CD8 binding agent of claim 1, wherein the VHH domain comprises:

(1) a CDR1 comprising the amino acid sequence of SEQ ID NO: 6, a CDR2 comprising the amino acid sequence of SEQ ID NO: 8, and a CDR3 comprising the amino acid sequence of SEQ ID NO: 10;

(2) a CDR1 comprising the amino acid sequence of SEQ ID NO: 6, a CDR2 comprising the amino acid sequence of SEQ ID NO: 9, and a CDR3 comprising the amino acid sequence of SEQ ID NO: 11;

(3) a CDR1 comprising the amino acid sequence of SEQ ID NO: 7, a CDR2 comprising the amino acid sequence of SEQ ID NO: 9, and a CDR3 comprising the amino acid sequence of SEQ ID NO: 11; or (4) a CDR1 comprising the amino acid sequence of SEQ ID NO: 6, a CDR2 comprising the amino acid sequence of SEQ ID NO: 9, and a CDR3 comprising the amino acid sequence of SEQ ID NO: 12.

3. The CD8 binding agent of claim 1, wherein (a) the VHH domain comprises L49A, wherein the numbering is according to Kabat numbering; and/or (b) the VHH domain comprises one or more amino acid modifications selected from the group consisting of V89T substitution, T110Q substitution, S112Q substitution and A114 addition, wherein the numbering is according to Kabat numbering; and/or (c) the agent does not comprise an Fc region.

4. The CD8 binding agent of claim 1, wherein the VHH domain comprises an amino acid sequence that has at least 80% amino acid sequence identity with the amino acid sequence of any one of SEQ ID Nos: 1-4.

5. An isolated nucleic acid encoding the CD8 binding agent of claim 1.

6. An expression vector comprising the nucleic acid of claim 5.

7. A host cell comprising the nucleic acid encoding the CD8 binding agent of claim 5 or an expression vector comprising the nucleic acid, wherein the host cell is a eukaryotic or prokaryotic cell.

8. The CD8 binding agent of claim 1, wherein the VHH domain is conjugated to a label, wherein the label is a fluorescent dye, radionuclide, or enzyme.

9. The CD8 binding agent of claim 1, wherein the VHH domain comprises an amino acid sequence that has at least 90% amino acid sequence identity with the amino acid sequence SEQ ID NO: 4 and wherein the agent does not comprise an Fc region.

10. A pharmaceutical composition comprising the CD8 binding agent of claim 1, comprising pharmaceutically acceptable excipients, further optionally comprising one or more anti-oxidant compounds.

11. The CD8 binding agent of claim 1, wherein the VHH domain comprises a CDR1 comprising the amino acid sequence of SEQ ID NO: 6, a CDR2 comprising the amino acid sequence of SEQ ID NO: 9, and a CDR3 comprising the amino acid sequence of SEQ ID NO: 12.

12. The CD8 binding agent of claim 1, wherein a chelating moiety is covalently linked to the VHH domain wherein the chelating moiety is a compound of Formula (I):

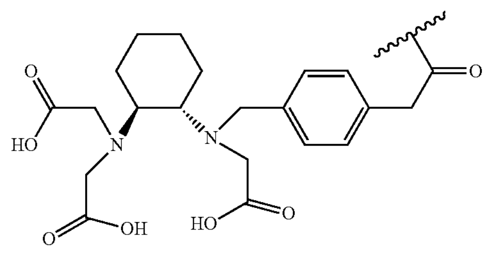 [SMILES: *C(=O)Cc1ccc(CN(CC(=O)O)[C@H]2CCCC[C@@H]2N(CC(=O)O)CC(=O)O)cc1]

and the chelating moiety is linked to the VHH domain via a lysine residue.

13. A pharmaceutical composition comprising the CD8 binding agent of claim 12, comprising pharmaceutically acceptable excipients, further optionally comprising one or more anti-oxidant compounds.

14. The CD8 binding agent of claim 1, wherein the VHH domain is conjugated to a label, wherein the label is a radionuclide.

15. The CD8 binding agent of claim 14, wherein the radionuclide is selected from $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{75}Sc$, $^{77}As$, $^{86}Y$, $^{89}Sr$, $^{89}Zr$, $^{90}Y$, $^{90}Nb$, $^{94}Tc$, $^{99}Tc$, $^{99}m$ Tc, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154\text{-}158}Gd$, $^{161}Tb$, $^{166}Dy$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$ or $^{225}Ac$.

16. The CD8 binding agent of claim 14, wherein the radionuclide is selected from $^{18}F$, $^{89}Zr$, $^{99}mTc$, $^{67}Ga$, $^{68}Ga$, $^{64}Cu$, $^{52}Mn$, $^{111}In$, or $^{124}I$.

17. The CD8 binding agent of claim 14, wherein the radionuclide is 18F.

18. The CD8 binding agent of claim 14, wherein the VHH domain is conjugated to the label via a chelating moiety, wherein the chelating moiety is a compound of Formula (I):

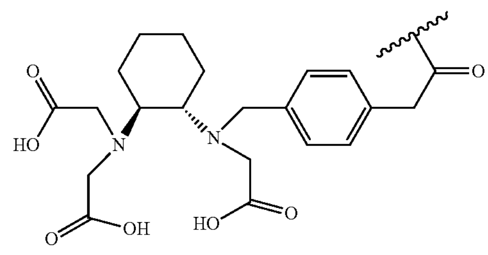 [SMILES: *C(=O)Cc1ccc(CN(CC(=O)O)[C@H]2CCCC[C@@H]2N(CC(=O)O)CC(=O)O)cc1]

and the chelating moiety is linked to the VHH domain via a lysine residue.

19. A pharmaceutical composition comprising the CD8 binding agent of claim 18, comprising pharmaceutically acceptable excipients, further optionally comprising one or more anti-oxidant compounds.

20. The CD8 binding agent of claim 18, wherein the label forms a complex with a metal and the complex is chelated by the chelating moiety.

21. The CD8 binding agent of 20, wherein the metal is aluminum and the radionuclide is $^{18}F$.

22. The CD8 binding agent of claim 21, wherein the VHH domain comprises a CDR1 comprising the amino acid sequence of SEQ ID NO: 6, a CDR2 comprising the amino acid sequence of SEQ ID NO: 9, and a CDR3 comprising the amino acid sequence of SEQ ID NO: 12.

23. The CD8 binding agent of claim 21, wherein the VHH domain comprises an amino acid sequence that has at least 90% amino acid sequence identity with the amino acid sequence SEQ ID NO: 4.

* * * * *

SEQUENCE LISTING

```
<160> NUMBER OF SEQ ID NOS: 15

<210> SEQ ID NO 1
<211> LENGTH: 124
<212> TYPE: PRT
<213> ORGANISM: Lama glama

<400> SEQUENCE: 1

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Gly Arg Glu Gly Val
        35                  40                  45

Leu Cys Ile Arg Ile Phe Asp Arg His Thr Tyr Ser Ala Asp Ser Val
    50                  55                  60

Lys Gly Arg Phe Thr Ile Ser Ser Asp Asn Ala Gln Asn Thr Val Tyr
65                  70                  75                  80

Leu His Met Asn Ser Leu Lys Pro Glu Asp Thr Ala Val Tyr Tyr Cys
                85                  90                  95

Ala Ala Gly Ser Phe Trp Ala Cys Thr Arg Pro Glu Gly Ala Met Asp
            100                 105                 110

Tyr Trp Gly Lys Gly Thr Gln Val Thr Val Ser Ser
        115                 120


<210> SEQ ID NO 2
<211> LENGTH: 125
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Glu Asp Tyr
            20                  25                  30

Ala Ile Gly Trp Phe Arg Gln Ala Pro Gly Lys Gly Arg Glu Gly Val
        35                  40                  45
```

-continued

```
Ala Cys Ile Arg Ile Phe Asp Arg His Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Ala Gly Ser Phe Phe Gly Cys Thr Arg Pro Glu Gly Asp Met Asp
            100                 105                 110

Tyr Phe Gly Gln Gly Thr Leu Val Gln Val Gln Ser Ala
        115                 120                 125


<210> SEQ ID NO 3
<211> LENGTH: 125
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Val Ile Gly Trp Phe Arg Gln Ala Pro Gly Lys Gly Arg Glu Gly Val
        35                  40                  45

Ala Cys Ile Arg Ile Phe Asp Arg His Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Ala Gly Ser Phe Phe Gly Cys Thr Arg Pro Glu Gly Asp Met Asp
            100                 105                 110

Tyr Phe Gly Gln Gly Thr Leu Val Gln Val Gln Ser Ala
        115                 120                 125


<210> SEQ ID NO 4
<211> LENGTH: 125
<212> TYPE: PRT
<213> ORGANISM: Artificial Sequence
<220> FEATURE:
<223> OTHER INFORMATION: Synthetic Construct

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Gly Arg Glu Gly Val
        35                  40                  45

Ala Cys Ile Arg Ile Phe Asp Arg His Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Ala Gly Ser Phe Trp Gly Cys Thr Arg Pro Glu Gly Asp Met Asp
            100                 105                 110
```

```
Tyr Phe Gly Gln Gly Thr Leu Val Gln Val Gln Ser Ala
        115                 120                 125


<210> SEQ ID NO 5
<211> LENGTH: 125
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Gly Arg Glu Gly Val
        35                  40                  45

Ala Cys Ile Arg Ile Phe Asp Arg His Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Ala Gly Phe Phe Ser Gly Cys Thr Arg Pro Glu Gly Asp Met Asp
            100                 105                 110

Tyr Phe Gly Gln Gly Thr Leu Val Gln Val Gln Ser Ala
        115                 120                 125


<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Asp Tyr Ala Ile Gly
1               5


<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

Asp Tyr Val Ile Gly
1               5


<210> SEQ ID NO 8
<211> LENGTH: 17
<212> TYPE: PRT
<213> ORGANISM: Artificial Sequence
<220> FEATURE:
<223> OTHER INFORMATION: Synthetic Construct

<400> SEQUENCE: 8

Cys Ile Arg Ile Phe Asp Arg His Thr Tyr Ser Ala Asp Ser Val Lys
1               5                   10                  15

Gly
```

<210> SEQ ID NO 9
<211> LENGTH: 17
<212> TYPE: PRT
<213> ORGANISM: Artificial Sequence
<220> FEATURE:
<223> OTHER INFORMATION: Synthetic Construct

<400> SEQUENCE: 9

Cys Ile Arg Ile Phe Asp Arg His Thr Tyr Tyr Ala Asp Ser Val Lys
1 5 10 15

Gly

<210> SEQ ID NO 10
<211> LENGTH: 15
<212> TYPE: PRT
<213> ORGANISM: Artificial Sequence
<220> FEATURE:
<223> OTHER INFORMATION: Synthetic Construct

<400> SEQUENCE: 10

Gly Ser Phe Trp Ala Cys Thr Arg Pro Glu Gly Ala Met Asp Tyr
1 5 10 15

<210> SEQ ID NO 11
<211> LENGTH: 15
<212> TYPE: PRT
<213> ORGANISM: Artificial Sequence
<220> FEATURE:
<223> OTHER INFORMATION: Synthetic Construct

<400> SEQUENCE: 11

Gly Ser Phe Phe Gly Cys Thr Arg Pro Glu Gly Asp Met Asp Tyr
1 5 10 15

<210> SEQ ID NO 12
<211> LENGTH: 15
<212> TYPE: PRT
<213> ORGANISM: Artificial Sequence
<220> FEATURE:
<223> OTHER INFORMATION: Synthetic Construct

<400> SEQUENCE: 12

Gly Ser Phe Trp Gly Cys Thr Arg Pro Glu Gly Asp Met Asp Tyr
1 5 10 15

<210> SEQ ID NO 13
<211> LENGTH: 234
<212> TYPE: PRT
<213> ORGANISM: Homo sapiens

<400> SEQUENCE: 13

Met Ala Leu Pro Val Thr Ala Leu Leu Leu Pro Leu Ala Leu Leu Leu
1 5 10 15

His Ala Ala Arg Pro Ser Gln Phe Arg Val Ser Pro Leu Asp Arg Thr
20 25 30

Trp Asn Leu Gly Glu Thr Val Glu Leu Lys Cys Gln Val Leu Leu Ser
35 40 45

Asn Pro Thr Ser Gly Cys Ser Trp Leu Phe Gln Pro Arg Gly Ala Ala
50 55 60

Ala Ser Pro Thr Phe Leu Leu Tyr Leu Ser Gln Asn Lys Pro Lys Ala
65 70 75 80

Ala Glu Gly Leu Asp Thr Gln Arg Phe Ser Gly Lys Arg Leu Gly Asp
85 90 95

```
Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr
225                 230
```

<210> SEQ ID NO 14
<211> LENGTH: 276
<212> TYPE: PRT
<213> ORGANISM: Macaca fascicularis

<400> SEQUENCE: 14

```
Met Arg Asn Gln Ala Pro Gly Arg Pro Lys Gly Ala Thr Ser Pro Pro
1               5                   10                  15

Pro Leu Pro Thr Gly Ser Arg Ala Pro Pro Val Ala Pro Glu Leu Arg
            20                  25                  30

Ala Glu Pro Arg Pro Gly Glu Arg Val Met Ala Pro Pro Val Thr Ala
        35                  40                  45

Leu Leu Leu Pro Leu Val Leu Leu Leu His Ala Ala Arg Pro Asn Gln
    50                  55                  60

Phe Arg Val Ser Pro Leu Gly Arg Thr Trp Asn Leu Gly Glu Thr Val
65                  70                  75                  80

Glu Leu Lys Cys Gln Val Leu Leu Ser Asn Pro Thr Ser Gly Cys Ser
                85                  90                  95

Trp Leu Phe Gln Pro Arg Gly Thr Ala Ala Arg Pro Thr Phe Leu Leu
            100                 105                 110

Tyr Leu Ser Gln Asn Lys Pro Lys Ala Ala Glu Gly Leu Asp Thr Gln
        115                 120                 125

Arg Phe Ser Gly Lys Arg Leu Gly Asp Thr Phe Val Leu Thr Leu Arg
    130                 135                 140

Asp Phe Arg Gln Glu Asn Glu Gly Tyr Tyr Phe Cys Ser Ala Leu Ser
145                 150                 155                 160

Asn Ser Ile Met Tyr Phe Ser His Phe Val Pro Val Phe Leu Pro Ala
                165                 170                 175

Lys Pro Thr Thr Thr Pro Ala Pro Arg Pro Pro Thr Pro Ala Pro Thr
            180                 185                 190

Thr Ala Ser Gln Pro Leu Ser Leu Arg Pro Glu Ala Cys Arg Pro Ala
        195                 200                 205

Ala Gly Gly Ser Val Asn Thr Arg Gly Leu Asp Phe Ala Cys Asp Ile
    210                 215                 220

Tyr Ile Trp Ala Pro Leu Ala Gly Ala Cys Gly Val Leu Leu Leu Ser
```

-continued

```
225                 230                 235                 240

Leu Val Ile Thr Leu Tyr Cys Asn His Arg Asn Arg Arg Arg Val Cys
                245                 250                 255

Lys Cys Pro Arg Pro Val Val Lys Ser Gly Gly Lys Pro Ser Leu Ser
            260                 265                 270

Asp Arg Tyr Val
        275


<210> SEQ ID NO 15
<211> LENGTH: 276
<212> TYPE: PRT
<213> ORGANISM: Macaca mulatta

<400> SEQUENCE: 15

Met Arg Asn Gln Ala Pro Gly Arg Pro Lys Gly Ala Thr Ser Pro Pro
1               5                   10                  15

Pro Leu Pro Thr Gly Ser Arg Ala Pro Pro Val Ala Pro Glu Leu Arg
            20                  25                  30

Ala Glu Pro Arg Pro Gly Glu Arg Val Met Ala Pro Pro Val Thr Ala
        35                  40                  45

Leu Leu Leu Pro Leu Val Leu Leu Leu His Ala Ala Arg Pro Asn Gln
    50                  55                  60

Phe Arg Val Ser Pro Leu Gly Arg Thr Trp Asn Leu Gly Glu Thr Val
65                  70                  75                  80

Glu Leu Lys Cys Gln Val Leu Leu Ser Asn Pro Thr Ser Gly Cys Ser
                85                  90                  95

Trp Leu Phe Gln Pro Arg Gly Thr Ala Ala Arg Pro Thr Phe Leu Leu
            100                 105                 110

Tyr Leu Ser Gln Asn Lys Pro Lys Ala Ala Glu Gly Leu Asp Thr Gln
        115                 120                 125

Arg Phe Ser Gly Lys Arg Leu Gly Asp Thr Phe Val Leu Thr Leu Arg
    130                 135                 140

Asp Phe Arg Gln Glu Asn Glu Gly Tyr Tyr Phe Cys Ser Ala Leu Ser
145                 150                 155                 160

Asn Ser Ile Met Tyr Phe Ser His Phe Val Pro Val Phe Leu Pro Ala
                165                 170                 175

Lys Pro Thr Thr Thr Pro Ala Pro Arg Ser Pro Thr Pro Ala Pro Thr
            180                 185                 190

Thr Ala Ser Gln Pro Leu Ser Leu Arg Pro Glu Ala Cys Arg Pro Ala
        195                 200                 205

Ala Gly Gly Ser Val Asn Thr Arg Gly Leu Asp Phe Ala Cys Asp Ile
    210                 215                 220

Tyr Ile Trp Ala Pro Leu Ala Gly Ala Cys Gly Val Leu Leu Leu Ser
225                 230                 235                 240

Leu Val Ile Thr Leu Tyr Cys Asn His Arg Asn Arg Arg Arg Val Cys
                245                 250                 255

Lys Cys Pro Arg Pro Val Val Lys Ser Gly Gly Lys Pro Ser Leu Ser
            260                 265                 270

Asp Arg Tyr Val
        275
```